US008969532B2

(12) United States Patent
DeFrees et al.

(10) Patent No.: US 8,969,532 B2
(45) Date of Patent: Mar. 3, 2015

(54) METHODS FOR THE PURIFICATION OF POLYPEPTIDE CONJUGATES COMPRISING POLYALKYLENE OXIDE USING HYDROPHOBIC INTERACTION CHROMATOGRAPHY

(75) Inventors: Shawn DeFrees, North Wales, PA (US); Kyle Kinealy, Plymouth Meeting, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 1064 days.

(21) Appl. No.: 11/866,969

(22) Filed: Oct. 3, 2007

(65) Prior Publication Data

US 2008/0253992 A1 Oct. 16, 2008

Related U.S. Application Data

(60) Provisional application No. 60/848,969, filed on Oct. 3, 2006, provisional application No. 60/864,117, filed on Nov. 2, 2006, provisional application No. 60/868,057, filed on Nov. 30, 2006, provisional application No. 60/887,517, filed on Jan. 31, 2007, provisional application No. 60/951,159, filed on Jul. 20, 2007, provisional application No. 60/955,001, filed on Aug. 9, 2007, provisional application No. 60/956,468, filed on Aug. 17, 2007.

(51) Int. Cl.
| | |
|---|---|
| *C07K 1/18* | (2006.01) |
| *C07K 1/36* | (2006.01) |
| *C12P 21/00* | (2006.01) |
| *A61K 47/48* | (2006.01) |
| *C07K 1/13* | (2006.01) |
| *C07K 1/20* | (2006.01) |
| *C07K 14/00* | (2006.01) |

(Continued)

(52) U.S. Cl.
CPC ......... *C12P 21/005* (2013.01); *A61K 47/48215* (2013.01); *C07K 1/13* (2013.01); *C07K 1/20* (2013.01); *C07K 14/00* (2013.01); *C07K 14/505* (2013.01); *Y10S 930/09* (2013.01)
USPC ........... 530/412; 530/402; 530/416; 530/417; 930/90

(58) Field of Classification Search
None
See application file for complete search history.

(56) References Cited

U.S. PATENT DOCUMENTS

| | | | |
|---|---|---|---|
| 4,055,635 A | 10/1977 | Green et al. | |
| 4,088,538 A | 5/1978 | Schneider | |

(Continued)

FOREIGN PATENT DOCUMENTS

| | | |
|---|---|---|
| AU | 1991/083760 A | 3/1992 |
| AU | 1992/017052 | 12/1992 |

(Continued)

OTHER PUBLICATIONS

Clark et al, 1996 (Journal of Biological Chemistry. 271(36): 21969-21977).*

(Continued)

*Primary Examiner* — Zachary Howard
(74) *Attorney, Agent, or Firm* — Leydig, Voit & Mayer, Ltd.

(57) ABSTRACT

The present invention provides processes for the manufacturing of polypeptide conjugates. In particular, the invention provides methods for the purification of polypeptide conjugates, which include at least one polymeric modifying groups, such as a poly(alkylene oxide) moiety. Exemplary poly(alkylene oxide) moieties include poly(ethylene glycol) (PEG) and poly(propylene glycol). In an exemplary process, hydrophobic interaction chromatography (HIC) is used to resolve different glycoforms of glycoPEGylated polypeptides.

65 Claims, 9 Drawing Sheets

(51) Int. Cl.
*C07K 17/08* (2006.01)
*C07K 14/505* (2006.01)

(56) References Cited

U.S. PATENT DOCUMENTS

| | | | |
|---|---|---|---|
| 4,179,337 A | 12/1979 | Davis et al. |
| 4,385,260 A | 5/1983 | Watts et al. |
| 4,412,989 A | 11/1983 | Iwashita et al. |
| 4,414,147 A | 11/1983 | Klibanov |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,704,361 A | 11/1987 | Miccoli et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |
| 5,278,299 A | 1/1994 | Wong et al. |
| 5,281,698 A | 1/1994 | Nitecki |
| 5,288,637 A | 2/1994 | Roth |
| 5,308,460 A | 5/1994 | Mazid et al. |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot |
| 5,369,017 A | 11/1994 | Wong et al. |
| 5,374,541 A | 12/1994 | Wong |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer |
| 5,409,817 A | 4/1995 | Ito et al. |
| 5,410,016 A | 4/1995 | Hubbell et al. |
| 5,432,059 A | 7/1995 | Bean |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | Defrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |

(56) References Cited

U.S. PATENT DOCUMENTS

| | | | |
|---|---|---|---|
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,008,252 B2 | 8/2011 | DeFrees et al. |
| 8,063,015 B2 | 11/2011 | DeFrees et al. |
| 8,178,108 B2 * | 5/2012 | Buechler et al. ............ 424/198.1 |
| 8,207,112 B2 | 6/2012 | Hinderer et al. |
| 8,247,381 B2 | 8/2012 | DeFrees |
| 8,268,967 B2 | 9/2012 | DeFrees et al. |
| 8,361,961 B2 | 1/2013 | DeFrees et al. |
| 8,633,157 B2 | 1/2014 | DeFrees et al. |
| 8,716,239 B2 | 5/2014 | DeFrees et al. |
| 8,716,240 B2 | 5/2014 | DeFrees et al. |
| 8,791,066 B2 | 7/2014 | DeFrees |
| 8,791,070 B2 | 7/2014 | DeFrees et al. |
| 8,841,439 B2 | 9/2014 | Felo et al. |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda et al. |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | DeFrees |
| 2006/0182714 A1 | 8/2006 | Behrens et al. |
| 2006/0183198 A1 | 8/2006 | Buechler et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | Defrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |

(56) References Cited

U.S. PATENT DOCUMENTS

| | | |
|---|---|---|
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |
| 2014/0112903 A1 | 4/2014 | DeFrees et al. |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |
| EP | 0474313 A | 3/1992 |
| EP | 0475354 A2 | 3/1992 |
| EP | 0577580 A2 | 1/1994 |
| EP | 0585109 A | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 A1 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H02-076894 A | 3/1990 |
| JP | H03-503759 A | 8/1991 |
| JP | H06-086684 A | 3/1994 |
| JP | H06-160365 A | 6/1994 |
| JP | H06-172375 A | 6/1994 |
| JP | H07-196925 A | 8/1995 |
| JP | H07-223921 A | 8/1995 |
| JP | H08-506023 A | 7/1996 |
| JP | H09-503905 A | 4/1997 |
| JP | H09-208461 A | 8/1997 |
| JP | H10-307356 A | 11/1998 |
| JP | 2000-501607 A | 2/2000 |
| JP | 2001-508783 A | 7/2001 |
| JP | 2001-519784 A | 10/2001 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 A | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 87/00056 | 1/1987 |
| WO | WO 87/05330 A1 | 9/1987 |
| WO | WO 89/06546 A | 7/1989 |
| WO | WO 89/10134 A1 | 11/1989 |
| WO | WO 90/07572 | 7/1990 |
| WO | WO 90/08164 A1 | 7/1990 |
| WO | WO 90/08823 A1 | 8/1990 |
| WO | WO 90/12090 A1 | 10/1990 |
| WO | WO 90/13540 A1 | 11/1990 |
| WO | WO 91/06635 A1 | 5/1991 |
| WO | WO 91/09122 A1 | 6/1991 |
| WO | WO 91/14697 A1 | 10/1991 |
| WO | WO 92/01055 A1 | 1/1992 |
| WO | WO 92/15686 A1 | 9/1992 |
| WO | WO 92/16555 A1 | 10/1992 |
| WO | WO 92/16640 A1 | 10/1992 |
| WO | WO 92/18135 | 10/1992 |
| WO | WO 92/22310 A1 | 12/1992 |
| WO | WO 93/08842 A1 | 5/1993 |
| WO | WO 93/13198 A1 | 7/1993 |
| WO | WO 93/15189 A1 | 8/1993 |
| WO | WO 93/18787 A1 | 9/1993 |
| WO | WO 94/04193 A1 | 3/1994 |
| WO | WO 94/05332 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/25614 A1 | 11/1994 |
| WO | WO 94/25615 A1 | 11/1994 |
| WO | WO 94/26760 A1 | 11/1994 |
| WO | WO 94/27631 A1 | 12/1994 |
| WO | WO 94/28024 A1 | 12/1994 |
| WO | WO 95/02421 A1 | 1/1995 |
| WO | WO 95/04278 A1 | 2/1995 |
| WO | WO 95/05465 A1 | 2/1995 |
| WO | WO 96/10089 A1 | 4/1996 |
| WO | WO 96/11953 A1 | 4/1996 |
| WO | WO 96/12800 A1 | 5/1996 |
| WO | WO 96/40731 | 6/1996 |
| WO | WO 96/21468 A1 | 7/1996 |
| WO | WO 96/21469 A1 | 7/1996 |
| WO | WO 96/32491 | 10/1996 |
| WO | WO 96/32492 A1 | 10/1996 |
| WO | WO 96/34015 A1 | 10/1996 |
| WO | WO 96/36357 A1 | 11/1996 |
| WO | WO 96/40881 A1 | 12/1996 |
| WO | WO 97/05330 | 2/1997 |
| WO | WO 97/21822 A2 | 6/1997 |

(56) References Cited

FOREIGN PATENT DOCUMENTS

| | | |
|---|---|---|
| WO | WO 97/47651 A1 | 12/1997 |
| WO | WO 98/05363 | 2/1998 |
| WO | WO 98/31826 | 7/1998 |
| WO | WO 98/32466 A1 | 7/1998 |
| WO | WO 98/41562 A1 | 9/1998 |
| WO | WO 98/51784 A1 | 11/1998 |
| WO | WO 98/58964 | 12/1998 |
| WO | WO 99/00150 A2 | 1/1999 |
| WO | WO 99/13063 A1 | 3/1999 |
| WO | WO 99/14259 A1 | 3/1999 |
| WO | WO 99/22764 A1 | 5/1999 |
| WO | WO 99/28491 A1 | 6/1999 |
| WO | WO 99/34833 A1 | 7/1999 |
| WO | WO 99/37779 A1 | 7/1999 |
| WO | WO 99/45964 A1 | 9/1999 |
| WO | WO 99/48515 A1 | 9/1999 |
| WO | WO 99/54342 A1 | 10/1999 |
| WO | WO 99/55376 A1 | 11/1999 |
| WO | WO 00/23114 | 4/2000 |
| WO | WO 00/26354 A1 | 5/2000 |
| WO | WO 00/29558 A1 | 5/2000 |
| WO | WO 00/29603 A2 | 5/2000 |
| WO | WO 00/44785 A1 | 8/2000 |
| WO | WO 00/46379 A1 | 8/2000 |
| WO | WO 00/65087 | 11/2000 |
| WO | WO 01/02017 A2 | 1/2001 |
| WO | WO 01/05434 A2 | 1/2001 |
| WO | WO 01/19955 A2 | 3/2001 |
| WO | WO 01/39788 A2 | 6/2001 |
| WO | WO 01/49830 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | WO 01/83725 A1 | 11/2001 |
| WO | WO 01/87329 A1 | 11/2001 |
| WO | WO 01/87925 A2 | 11/2001 |
| WO | WO 01/88117 A2 | 11/2001 |
| WO | WO 02/02597 A2 | 1/2002 |
| WO | WO 02/13843 A2 | 2/2002 |
| WO | WO 02/13873 A1 | 2/2002 |
| WO | WO 02/29025 A2 | 4/2002 |
| WO | WO 02/44196 A1 | 6/2002 |
| WO | WO 02/49673 A2 | 6/2002 |
| WO | WO 02/50099 A2 | 6/2002 |
| WO | WO 02/053580 A2 | 7/2002 |
| WO | WO 02/74806 A2 | 9/2002 |
| WO | WO 02/02764 A2 | 10/2002 |
| WO | WO 02/077218 A1 | 10/2002 |
| WO | WO 02/092619 A2 | 11/2002 |
| WO | WO 03/006501 A2 | 1/2003 |
| WO | WO 03/011879 A1 | 2/2003 |
| WO | WO 03/017949 A2 | 3/2003 |
| WO | WO 03/029291 A2 | 4/2003 |
| WO | WO 03/031464 A2 | 4/2003 |
| WO | WO 03/045980 A2 | 6/2003 |
| WO | WO 03/046150 A2 | 6/2003 |
| WO | WO 03/093448 A2 | 11/2003 |
| WO | WO 04/000366 A1 | 12/2003 |
| WO | WO 2004/009838 A2 | 1/2004 |
| WO | WO 2004/010327 A2 | 1/2004 |
| WO | WO 2004/014417 A2 | 2/2004 |
| WO | WO 2004/022004 A2 | 3/2004 |
| WO | WO 2004/029090 A1 | 4/2004 |
| WO | WO 2004/029091 A2 | 4/2004 |
| WO | WO 2004/033651 A2 | 4/2004 |
| WO | WO 2004/046222 A2 | 6/2004 |
| WO | WO 2004/047858 A1 | 6/2004 |
| WO | WO 2004/067566 A1 | 8/2004 |
| WO | WO 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/093823 A2 | 11/2004 |
| WO | WO 2004/096148 A2 | 11/2004 |
| WO | WO 2004/099231 A2 | 11/2004 |
| WO | WO 2004/101597 A2 | 11/2004 |
| WO | WO 2004/101740 A2 | 11/2004 |
| WO | WO 2004/103275 A2 | 12/2004 |
| WO | WO 2004/106373 A1 | 12/2004 |
| WO | WO 2005/001025 A2 | 1/2005 |
| WO | WO 2005/003171 A2 | 1/2005 |
| WO | WO 2005/012484 A2 | 2/2005 |
| WO | WO 2005/014024 A2 | 2/2005 |
| WO | WO 2005/014035 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/079363 A2 | 9/2005 |
| WO | WO 2005/091944 A2 | 10/2005 |
| WO | WO 2005/121331 A2 | 12/2005 |
| WO | WO 2006/005058 A2 | 1/2006 |
| WO | WO 2006/010143 A2 | 1/2006 |
| WO | WO 2006/011839 A1 | 2/2006 |
| WO | WO 2006/013202 A2 | 2/2006 |
| WO | WO 2006/014349 A2 | 2/2006 |
| WO | WO 2006/014466 A2 | 2/2006 |
| WO | WO 2006/018204 A1 | 2/2006 |
| WO | WO 2006/020372 A2 | 2/2006 |
| WO | WO 2006/031811 A2 | 3/2006 |
| WO | WO 2006/035057 A1 | 4/2006 |
| WO | WO 2006/050247 A2 | 5/2006 |
| WO | WO 2006/053299 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | WO 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | WO 2006/134173 A2 | 12/2006 |
| WO | WO 2007/022512 A2 | 2/2007 |
| WO | WO 2007/056191 A2 | 5/2007 |
| WO | WO 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

"Hydrophobic Interaction Chromatography: Principles and Methods" (published by Amersham Pharmacia Biotech in the year 2000; no author indicated; 104 pages as published.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Abuchowski et al., *J. Biol. Chem.*, 252: 3582-3586 (1977).
Boime et al., *Recent Prog. Horm. Res.*, 54: 271-289 (1999).
Copeland, Robert A., *Enzymes*, Second Edition, 146-150 (2000).
Felix et al., *J. Peptide Res.*, 63: 85-90 (2004).
Gervais et al., *Glycobiology*, 13(3): 179-189 (2003).
Gross et al., *Biochemistry*, 28: 7386-7392 (1989).
Kajihara et al., *Carbohydrate Research*, 315: 137-141 (1999).

(56) References Cited

OTHER PUBLICATIONS

Kawasaki et al., *Analytical Biochemistry*, 285: 82-91 (2000).
Katre et al., *Proc. Natl. Acad. Sci. U.S.A.*, 84: 1487-1491 (1987).
Keppler et al., *Glycobiology*, 11: 11R-18R (2001).
Min et al., *Endocr. J.*, 43:585-593 (1996).
Seely et al., *Journal of Chromatography*, 908: 235-241 (2001).
Snider et al., *Journal of Chromatography*, 599: 141-155 (1992).
Srinivasachar et al., *Biochemistry*, 28: 2501-2509 (1989).
Urdal et al, *J. Chromatog*, 296: 171-179 (1984).
Witte et al., *J. Am. Chem. Soc.* 119: 2114-2118 (1997).
Wu et al., *J. Drug targeting* 10: 239-245 (2002).
Abeijon et al., 1986, J. Biol. Chem. 261(24):11374-11377.
Abuchowski et al., 1977, J. Biol. Chem. 252:3582-3586.
Abuchowski et al., 1984, Cancer Biochem. Biophys. 7:175-186.
Abuchowski et al., 1977, J. Biol. Chem. 252:3578-3581.
Ailor et al., 2000, Glycobiology 10:837-847.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Berger et al., 1988, Blood 71:1641-1647.
Berg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bouizar et al., 1986, Eur. J. Biochem. 155:141-147.
Boyd et al., 1995, Mol. Immunol. 32:1311-1318.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. August 83:1-7.
Ginns, Dr. Edward, PEG Glucocerebrosidase, Internet page from www.gaucher.org.uk/peg2.prg, printed Jun. 21, 2002.

Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hall et al., 2001, Methods in Molecular Biology 166:139-154.
Haneda et al., Carbohydr. Res. 292:61-70.
Hang et al., 2001, J. Am. Chem. Soc. 123:1242-1243.
Harris, 1985, Macronol. Chem. Phys. C25: 325-373.
Harris et al., 2003, Nature Reviews Drug Discovery, 2:214-221.
Hayes et al., 1993, J. Biol. Chem. 268(22):16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Inoue et al., 1995, Biotechnology Annual Review 1:297-313.
Ito et al., 1993, Pure & Appl. Chem. 65(4):753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lee-Huang et al., 1984, Proc. Natl. Acad. Sci. U.S.A. 81:2708-2712.
Lee et al., 1989, Biochemistry 28:1856-1861.
Leung, S., 1995, J. Immunology, 154:5919-5926.
Li et al., 2002, Trends in Pharmacological Sciences 23:206-209.
Li et al., 2002, Medicinal Research Reviews 22:225-250.
Liu et al., 2002, 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Molecular cloning and enzymatic characterization of a *Trichoderma reesei* , 2α-D-mannosidase, 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
NCBI—Accession No. NCAA26095 (2 pgs.).
NCBI—Accession No. NP_999299 (2 pgs.).
NCBI—Accession No. NP_058697 (3 pgs.).
NCBI Database hits for erythropoietin protein sequences (3 pgs.).
Nilsson et al., 1984, Methods Enzymol. 104:56-69.
O'Connell et al., 1992, J. Biol. Chem. 267:25010-25018.
Oetke, et al., 2002, J. Biol. Chem 277(8):6688-6695.
Olson et al., 1999, J. Biol. Chem. 274:29889-29896.
Palacpac et al., 1999, PNAS USA 96:4692-4697.
Park et al., 1986, J. Biol Chem. 261:205-210.

(56) References Cited

OTHER PUBLICATIONS

Paulson et al., 1997, J. Biol. Chem. 252:8624-8628.
Plummer et al., 1995, J. Biol. Chem. 270(22):13192-13196.
PNGase-F Amidase Sequence from *F. meningosepticum* (Registry Nos. 128688-70-0).
PNGase-F Amidase Sequence from *F. meningosepticum* (Registry Nos. 128688-71-1).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Rosenthal, et al., 1994, Methods Enzymol. 235:253-285.
Sadler et al., 1982, Methods in Enzymology 83:458-514.
Saneyoshi et al., 2001, Biology of Reproduction 65:1686-1690.
Saxon et al., 2000, Science 287:2007-2010.
Schwientek et al., 1994, Gene 145:299-303.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Song et al., 2002, J. Pharmacol. Exp. Ther. 301:605-610.
Srinivasachar et al., 1989, Biochemistry 28:2501-2509.
Stephens et al., 1983, European J. of Biochem., 135(3):519-27.
Stephens et al., 1983, European J. of Biochem., 133(3):481-9.
Stephens et al., 1983, European J. of Biochem., 133(1):155-62.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog. 296:171-179.
Van Berkel et al., 1996, Biochem J. 319:117-122.
Veronese et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly (ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.
Adelhorst et al., *J. Biol. Chem.*, 269(9): 6275-6278 (1994).
Alam et al., *J. Biotechnol.*, 65(2-3): 183-190 (1998).
Barrios et al., *J. Mol. Recognit.*, 17(4):332-338 (2004).
Bedard et al., *Cytotechnology*, 15(1-3):129-138 (1994).
Bennett et al., *J. Biol. Chem.*, 273(46): 30472-30481 (1998).
Bennett et al., *FEBS Lett.*, 460(2): 226-230 (1999).
Bijsterbosch et al., *Eur. J. Biochem.*, 237(2): 344-349 (1996).
Bork et al., *Trends Genet.*, 12(10): 425-427 (1996).
Brockhausen et al., *Acta Anatomica*, 161: 36-78 (1998).
Brockhausen et al., *Glycoconj. J.*, 15: 595-603 (1998).
Cohn et al., *J. Biomed. Mater. Res,.* 22(11): 993-1009 (1988).
Culajay et al., *Biochem.*, 39: 7153-7158 (2000).
Edge et al., *Anal. Biochem.*, 118(1): 131-137 (1981).
Feldman et al., *Proc. Natl. Acad. Sci. USA*, 102(8): 3016-3021 (2005).
Fritz et al., *Proc. Natl. Acad. Sci. USA*, 101(43): 15307-15312 (2004).
Fritz et al., *J. Biol. Chem.*, 281(13): 8613-8619 (2006).
Ge et al., *J. Biol. Chem.*, 272(34): 21357-21363 (1997).
Gilbert et al., *Cytotechnology*, 22(1-3): 211-216 (1996).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Grabenhorst et al., *J. Biol. Chem.*, 274(51): 36107-36116 (1999).
Hagen et al., *J. Biol. Chem.*, 274(10): 6797-6803 (1999).
Hagen et al., *J. Biol. Chem.*, 276(20): 17395-17404 (2001).
Harris et al., Abstracts of Papers of the American Chemical Society, V 201, APR, P 64-POLY, pp. 154-155 (1991).
Harris (ed.), "Poly(Ethylene Glycol) Chemistry: Biotechnical and Biomedical Applications", Plenum Press, New York (1992) (Title Pages).
Harris et al. (eds.), "Poly(ethylene glycol): Chemistry and Biological Applications," ACS Symposium Series, vol. 680, American Chemical Society (1997) (Title Pages).
Hassan et al., *J. Biol. Chem.*, 275(49): 38197-38205 (2000).
Hassan et al., *Carbohydrates in Chemistry and Biology*, Part II, 3: 273-292 (2000).
Herscovics et al., *FASEB J.*, 7(6): 540-550 (1993).
Hink et al., *Biotechnol. Prog.*, 7(1): 9-14 (1991).
Höglund, *Med. Oncol.*, 15(4): 229-233 (1998).
Ikonomou et al., *In Vitro Cell. Dev. Biol. Anim.*, 37(9): 549-559 (2001).
Inlow et al., *J. Tissue Cult. Methods*, 12(1): 13-16 (1989).
Keana et al., *J. Org. Chem.*, 55(11): 3640-3647 (1990).
Keene et al., *J. Biol. Chem.*, 264(9): 4769-4775 (1989).
Kobayashi et al., *Eur. J. Nucl. Med.*, 27(9):1334-1339 (2000).
Kornfeld et al., *Ann. Rev. Biochem.*, 54: 631-664 (1985).
Kukuruzinska et al., *Proc. Natl. Acad. Sci. USA*, 84(8): 2145-2149 (1987).
Langer, *Science*, 249(4976): 1527-1533 (1990).
Lau et al., *J. Biotechnol.*, 75(2-3): 105-115 (1999).
Legault et al., *J. Biol. Chem.*, 270(36): 20987-20996 (1995).
Licari et al., *Biotechnol. Bioeng.*, 39(4): 432-441 (1992).
Licari et al., *Biotechnol. Bioeng.*, 39(9): 932-944 (1992).
Lin et al., *Proc. Natl. Acad. Sci. USA*, 82: 7580-7584 (1985).
Meynial-Salles et al., *J. Biotechnol.*, 46(1): 1-14 (1996).
Monaco et al., *Gene*, 180: 145-150 (1996).
Muller et al., *J. Biol. Chem.*, 272(40): 24780-24793 (1997).
Muller et al., *J. Biol. Chem.*, 274(26): 18165-18172 (1999).
Nagata et al., *EMBO J.*, 5(3): 575-581 (1986).
Oh-Eda et al., *J. Biol. Chem.*, 265: 11432-11435 (1990).
Orlean, "vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Prati et al., *Biotech and Bioeng.*, 79(5): 580-585 (2002).
Rotondaro et al., *Mol. Biotech.*, 11: 117-128 (1999).
Rudikoff et al., *Proc. Natl. Acad. Sci. USA*, 79(6):1979-1983 (1982).
Sandberg et al., *Semin. Hematol.*, 38(2 Suppl. 4): 4-12 (2001).
Sasaki et al., *J. Biol. Chem.*, 262(25): 12059-12076 (1987).
Sasaki et al., *J.Biol. Chem.*, 269: 14730-14737 (1994).
Schlaeger, *Cytotechnology*, 20(1-3): 57-70 (1996).
Schwientek et al., *J. Biol. Chem.*, 277(25): 22623-22638 (2002).
Seitz, *Chembiochem.*, 1(4): 214-246 (2000).

(56) References Cited

OTHER PUBLICATIONS

Shen et al., *Biochem. Biophys. Res. Commun.*, 102(3): 1048-1054 (1981).
Shinkai et al., *Prot. Exp. Purif.*, 10: 379-385 (1997).
Smith et al., *Nat. Biotechnol.*, 15(12): 1222-1223 (1997).
Sojar et al., *Arch. Biochem. Biophys.*, 259(1): 52-57 (1987).
Stemmer, *Nature*, 370(6488): 389-391 (1994).
Stemmer, *Proc. Natl. Acad. Sci. USA*, 91(22): 10747-10751 (1994).
Strausberg et al., *Proc Natl Acad Sci USA*, 99(26): 16899-16903 (2002).
Taniguchi et al., *Proteomics*, 1(2): 239-247 (2001).
Ten Hagen et al., *J. Biol. Chem.*, 274(39): 27867-27874 (1999).
Tenno et al., *J. Biol. Chem.*, 277(49): 47088-47096 (2002).
Tsunoda et al., *J. Pharmacol. Exp. Ther.*, 209(1): 368-372 (1999).
Van Reis et al., *Biotechnol. Bioeng.*, 38(4): 413-422 (1991).
Vitetta et al., *Science*, 313: 308-309 (2006).
White et al., *J. Biol. Chem.*, 270(41): 24156-24165 (1995).
Witte et al., *Cancer and Metastasis Rev.*, 17: 155-161 (1998).
Wong et al., *J. Org. Chem.*, 47(27): 5416-5418 (1982).
Yamada et al., *Biochemistry*, 20(17): 4836-4842 (1981).
Younes et al., *J. Biomed. Mater. Res.*, 21(11): 1301-1316 (1987).
Zarling et al., *J. Immunol.*, 124(2): 913-920 (1980).
Arslan et al., *Transf. Apher. Sci.*, 37: 179-185 (2007).
Broxmeyer et al., *J. Exp. Med.*, 201(8): 1307-1318 (2005).
Brumeanu et al., *J. Immunol. Meth.*, 183: 185-197 (1995).
Cantin et al., *Am. J. Respir. Cell Mol. Biol.*, 27(6): 659-665 (2002).
Capoccia et al., *Blood*, 108(7): 2438-2445 (2006).
Cashen et al., *Bone Marrow Trans.*, 39: 577-588 (2007).
Flomenberg et al., *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Gross et al., *Eur. J. Biochem,.* 177(3): 583-589 (1988).
Hällgren et al., *J. Carb. Chem.*, 14(4-5): 453-464 (1995).
Haneda et al., *Carbohydr. Res.*, 292: 61-70 (1996).
Hill et al., *Biol. Blood Marrow Trans.*, 12: 603-607 (2006).
Hübel et al., *Ann. Hematol.*, 82: 207-213 (2003).
Kennedy, "Hydrophobic-Interaction Chromatography," in *Current Protocols in Protein Science*, pp. 8.4.1-8.4.21, Wiley (1995).
Kroschinsky et al., *Trans. Apher. Sci.*, 38: 237-244 (2008).
Liles et al., *Transfusion*, 45: 295-300 (2005).
Liu et al., *Chem. Eur. J.*, 2(11): 1359-1362 (1996).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
O'Shannessy et al., *J. Appl. Biochem.*, 7: 347-355 (1985).
Perrin et al., "Common Physical Techniques Used in Purification," in *Purification of Laboratory Chemicals*, pp. 30-31, Pergamon (1980).
PNGase-F Amidase Sequence from *F. meningosepticum* (RN 128688-70-0) (2007).
PNGase-F Amidase Sequence from *F. meningosepticum* (RN 128688-71-1) (2007).
Song et al., *Mar. Drugs*, 1: 34-45 (2003).
Uptima, Detergents: Solubilization of Biomolecules, Internet page from www.interchim.com/interchim/bio/produits_uptima/product_line/p1p_detergents.htm, 2001, printed Nov. 14, 2011.
Yin et al., *Pharm. Res.*, 21(12): 2377-2383 (2004).
Zhang et al., "Stable Expression of Human Alpha-2,6-Sialyltransferase in Chinese Hamster Ovary Cells: Functional Consequences for Human Erythropoietin Expression and Bioactivity," *Biochim. Biophys. Acta*, 1425: 441-452 (1998).
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Office Action dated Oct. 23, 2012 in U.S. Appl. No. 12/811,963.
Office Action dated Nov. 9, 2012 in U.S. Appl. No. 12/663,056.
Office Action dated Nov. 26, 2012 in U.S. Appl. No. 13/215,439.
Office Action dated Dec. 21, 2012 in U.S. Appl. No. 13/246,512.
Office Action dated Jan. 17, 2013 in U.S. Appl. No. 13/541,185.
Broun et al., *Science*, 282(5392): 1315-1317 (1998).
Costa et al., *J. Biol. Chem.*, 272(17): 11613-11621 (1997).
Deacon, *Diabetes*, 54: 2181-2189 (2004).
De Vries et al, *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Elhalabi et al., *Curr. Med. Chem.*, 6(2): 93-116 (1999).
Espuelas et al., *Bioorg. Med. Chem. Lett.*, 13(15): 2557-2560 (2003).
Fairhall et al., *Endocrinology*, 131(4): 1963-1969 (1992).
Francis et al., *Intl. J. Hematol.*, 68(1): 1-18 (1998).
Guo et al., *Appl. Biochem. Biotechnol.*, 68(1-2): 1-20 (1997).
Hansen et al., *Biochem J.*, 308: 801-813 (1995).
Haro et al., *Biochem. Biophys. Res. Comm.*, 228(2): 549-556 (1996).
Hu et al., *Mol. Cell. Biol.*, 18(10): 6063-6074 (1998).
Jezek et al., *J. Peptide Sci.*, 5: 46-55 (1999).
Kaneko et al., *Cytogenet. Cell Genet.*, 86(3-4): 329-330 (1999).
Kaneko et al., *FEBS Lett.*, 452(3): 237-242 (1999).
Kimura et al., *Proc. Natl. Acad. Sci. USA*, 96(8): 4530-4535 (1999).
Kisselev, *Structure*, 10(1): 8-9 (2002).
Krystal et al., *Blood*, 67(1): 71-99 (1986).
Kukowska-Latallo et al., *Genes Dev.*, 4(8): 1288-1303 (1990).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lönnberg, *Curr. Org. Synth.*, 6(4): 400-425 (2009).
Malissard et al., *Biochem. Biophys. Res. Commun.*, 267(1): 169-173 (2000).
Mollicone et al., *Eur. J. Biochem.*, 191(1): 169-176 (1990).
Natsuka et al., *J. Biol. Chem.*, 269(24): 16789-16794 (1994).
Nunez et al., *Can. J. Chem.*, 59(14): 2086-2095 (1981).
Orskov et al., *J. Biol. Chem.*, 264(22): 12826-12829 (1989).
Palcic et al., *Carbohydr. Res.*, 190(1): 1-11 (1989).
Prieels et al., *J. Biol. Chem.*, 256(20): 10456-10463 (1981).
Quelle et al., *Blood*, 74(2): 652-657 (1989).
Rasko et al., *J. Biol. Chem.*, 275(7): 4988-4994 (2000).
R & D Systems, Fibroblast Growth Factors (FGFs), Internet page from www.rndsystems.com/mini_review_detail_objectname_MR01_FGFs.aspx, 2001, printed Mar. 10, 2011.
Rathnam et al., *Biochim. Biophys. Acta*, 624(2): 436-442 (1980).
Saxon et al., *J. Am. Chem. Soc.*, 124(50): 14893-14902 (2002).
Schwarz et al., *Nucl. Med. Biol.*, 26(4):383-388 (1999).
Seffernick et al., *J. Bacteriol.*, 183(8): 2405-2410 (2001).
Sinclair et al., *J. Pharm. Sci.*, 94: 1626-1635 (2005).
Srivastava et al., *J. Biol. Chem.*, 267(31): 22356-22361 (1992).
Staudacher, *Trends Glycosci. Glycotechnol.*, 8(44): 391-408 (1996).
Tom et al., *AAPS Journal*, 9(2): E227-E234 (2007).
Trottein et al., *Mol. Biochem. Parasitol.*, 107(2): 279-287 (2000).
Van Tetering et al., *FEBS Lett.*, 461(3): 311-314 (1999).
Veronese, *Biomaterials*, 22(5): 405-417 (2001).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(6): 4152-4160 (1992).
Weston et al., *J. Biol. Chem.*, 267(34): 24575-24584 (1992).
Wishart et al., *J. Biol. Chem.*, 270(45): 26782-26785 (1995).
Witkowski et al., *Biochemistry*, 38(36): 11643-11650 (1999).
Office Action dated Sep. 20, 1994 in U.S. Appl. No. 08/215,727.
Office Action dated May 4, 1995 in U.S. Appl. No. 08/102,385.

(56) References Cited

OTHER PUBLICATIONS

Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.

(56) References Cited

OTHER PUBLICATIONS

Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.

(56) References Cited

OTHER PUBLICATIONS

Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).
Brinkman-Van Der Linden et al., *J. Biol. Chem.*, 271(24): 14492-14495 (1996).
Broquet et al., *Eur. J. Biochem.* 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al, *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett* 1999, (9): 1495-1507 (1999).
De Rosa et al., *Phytochemistry*, 42(4): 1031-1034 (1996).
DeAngelis et al., *Biochemistry*, 33(31): 9033-9039 (1994).
DeLuca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Drucker et al., "Glucagon Gene Expression in Vertebrate Brain," *J. Biol. Chem.*, 263(27): 13475-13478 (1988).
Dudas et al., *Infect. Immun.*, 56(2): 499-504 (1988).
Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia, pp. 568-575 (1988).
EMBL Accession No. M80599 and M86935, pp. 1-6 (Jan. 23, 1992).
EMBL Accession No. S56361, pp. 1-4 (May 4, 1993).
EMBL Accession No. U00039, pp. 1-137 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare, Instructions 28-9064-05 AA, pp. 1-32 (2006).
GE Healthcare, Instructions 28-9064-05 AC, pp. 1-40 (2006).
Genbank Accession No. AAA98726, "Factor IX," pp. 1-3 (Apr. 14, 2009).
Genbank Accession No. CAA01607, "Factor IX of *Homo sapiens*," pp. 1-2 (Apr. 14, 2009).
Genbank Accession No. D49915, pp. 1-3 (Sep. 1, 1995).
Genbank Accession No. U02304, p. 1 (Mar. 8, 1994).
Genbank Accession No. U18918, p. 1 (Oct. 1, 1995).
Gibson et al., *J. Bacteriol.*, 175(9): 2702-2712 (1993).
Gilbert, "Methods in Enzymology" Packer (ed.), 2(251): 8-28, Biothiols Part A, Elsevier (1995).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Gillespie et al., *FASEB Journal*, 4(7): A2068 [Abstract No. 2173] (1990).
Gillespie et al., *J. Biol. Chem.*, 267(29): 21004-21010 (1992).
Goodson et al., *Biotechnology (N.Y.)*, 8(4): 343-346 (1990).
Greenwell et al., *Blood Group A Synthesising Activity of the Blood Group B Gene Specified .alpha.-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Helling et al., *Cancer Res.*, 54(1): 197-203 (1994).
Higa et al., *J. Biol. Chem.*, 260(15): 8838-8849 (1985).
Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990).
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).
Koeller et al., "Complex Carbohydrate Synthesis Tools for Glycobiologists: Enzyme-Based Approach and Programmable One-Pot Strategies," *Glycobiology*, 10(11): 1157-1169 (2000).

(56) References Cited

OTHER PUBLICATIONS

Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta.*, 1437(2): 101-118 (1999).
MacKenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).
Manfioletti et al., "The Protein Encoded by a Growth Arrest-Specific Gene (*gas6*) Is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Monfardini et al., "A Branched Monomethoxypoly (ethylene glycol) for Protein Modification," *Bioconjug. Chem.*, 6(1): 62-69 (1995).
Moscatelli et al., "Enzymatic Properties of a β-Glucanase from *Bacillus subtilis*," *J. Biol. Chem.*, 236(11): 2858-2862 (1961).
Muramatsu et al., *Comprehensive Research on Clinical Organ Xenotransplantation by Genetic Regulation*, p. 10-12. (1997).
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Raju et al., "Glycoengineering of Therapeutic Glycoproteins: In Vitro Galactosylation and Sialylation of Glycoproteins with Terminal *N*-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbiol.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).

Sandlin et al., *J. Bacteriol.*, 176(10): 2930-2937 (1994).
Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).
Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
Swiss-Prot Accession No. P19817, p. 1 (Feb. 1, 1991).
Swiss-Prot Accession No. P25740, pp. 1-6 (May 1, 1992).
Swiss-Prot Accession No. P27129, pp. 1-5 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl Le$^x$ but Not 6-Sulfo Sialyl Le$^x$ Expressed on the Cell Surface Supports L-selectin-mediated Adhesion," *J. Biol. Chem.*, 271(44): 27213-27216 (1996).
Tsuji, "Molecular Cloning and Functional Analysis of Sialyltransferases," *J. Biochemistry*, 120: 1-13 (1996).
Tsujihara et al., *Chem. Pharm. Bull.*, (Tokyo) 29(11): 3262-3273 (1981).
Van Den Eijnden et al., *J. Biol. Chem.*, 256(7): 3159-3162 (1981).
Van Den Eijnden et al., *J. Biol. Chem.*, 258(6): 3435-3437 (1983).
Van Putten et al., *EMBO J.*, 12(11): 4043-4051 (1993).
Van Roey et al., *Biochemistry*, 33(47): 13989-13996 (1994).
Vann et al., *J Biol Chem.*, 262(36): 17556-17562 (1987).
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Webster et al., *J. Biol. Chem.*, 258(17): 10637-10641 (1983).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia, Image:Ceramide.svg, http://en.wikipedia.org/wiki/Ceramide, pp. 1-2 (2007).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).
Yamasaki et al., *J. Bacteriol.*, 175(14): 4565-4568 (1993).
Yoshikawa et al., *Phytochemistry*, 34(5): 1431-1433 (1993).
Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).

\* cited by examiner

Det 168-214nm
Results

| Name | Retention Time | Area | Area Percent |
|---|---|---|---|
| mono-PEG-EPO | 8.9 | 511907 | 1.8 |
| di-PEG-EPO | 10.2 | 4896915 | 17.0 |
| tri-PEG-EPO | 10.8 | 22813052 | 79.3 |
| | 11.6 | 378882 | 1.3 |
| tetra-PEG-EPO | 12.0 | 185275 | 0.6 |

30 kDa

US 8,969,532 B2

METHODS FOR THE PURIFICATION OF POLYPEPTIDE CONJUGATES COMPRISING POLYALKYLENE OXIDE USING HYDROPHOBIC INTERACTION CHROMATOGRAPHY

CROSS-REFERENCES TO RELATED APPLICATIONS

The present application claims priority to U.S. Provisional Patent Application No. 60/848,969, filed on Oct. 3, 2006, U.S. Provisional Patent Application No. 60/864,117, filed on Nov. 2, 2006; U.S. Provisional Patent Application No. 60/868,057, filed on Nov. 30, 2006; U.S. Provisional Patent Application No. 60/887,517, filed on Jan. 31, 2007; U.S. Provisional Patent Application No. 60/951,159, filed on Jul. 20, 2007; U.S. Provisional Patent Application No. 60/955,001, filed on Aug. 9, 2007; and U.S. Provisional Patent Application No. 60/956,468, filed Aug. 17, 2007, each of which is incorporated herein by reference in their entirety for all purposes.

FIELD OF THE INVENTION

The invention pertains to the field of polypeptide manufacturing. In particular, the invention relates to processes for the purification of polypeptide conjugates, especially those conjugates including poly(alkylene oxide)-based modification groups.

BACKGROUND OF THE INVENTION

The current literature contains a wealth of information directed to polypeptide purification methodologies, which primarily involve chromatographic approaches as well as membrane filtration techniques. However, effective methods for the purification of modified polypeptides (e.g., PEGylated polypeptides) are not well known. The modification of polypeptides with polymeric moieties causes a significant shift in the chemical and physical properties of those polypeptides. Methods, which are useful for the purification of non-modified polypeptides are not necessarily effective in capturing their modified versions.

When a glycosylated or non-glycosylated polypeptide is subjected to a chemical modification reaction, side-products may be formed in addition to the desired modified polypeptide. In order to isolate a desired product from a reaction mixture, the process must not only be suitable to remove chemical reagents, but must also be capable of removing unwanted side-products. This is especially important when the polypeptide is to be used as a therapeutic agent. Polypeptide modification technologies, which rely on the specificity of enzymes, may result in a reaction product that is characterized by improved homogeneity when compared to other chemical methods. However, expression of a recombinant polypeptide in a cell (e.g., bacterial, insect, yeast or mammalian cell) typically results in a polypeptide population that, at leas to some extend, is characterized by a variety of glycan structures. Subsequent modification of the polypeptide, e.g., via those glycans, results in a heterogenous product. Although remodeling glycan structures prior to chemical or enzymatic modification of the polypeptide can significantly improve the quality of the product, a certain degree of heterogeneity remains. Hence, a need exists for production processes designed to isolate a desired polypeptide conjugate from a reaction mixture that may not only contain chemical reagents (e.g., those derived from unreacted modifying groups) and/or catalytic enzymes, but may also include polypeptide conjugate by-products. The present invention addresses these and other needs.

SUMMARY OF THE INVENTION

The present invention provides processes for the isolation (e.g., large-scale purification) of polypeptide conjugates. The polypeptide conjugates of the present invention include a polypeptide that is modified with a modifying group, such as a polymer. Exemplary polymers include water-soluble polymers. The methods of the invention are particularly useful for the isolation of polypeptide conjugates that include poly (alkylene oxide)-based polymers, such as poly(ethylene glycol) and poly(propylene glycol). While reverse-phase (RP) chromatography can be used to purify polypeptides that are derivatized with such highly polar, water-soluble polymers, the technique is not desirable because it requires the use of water-soluble organic solvents, such as acetonitrile. Organic solvents, especially in large-scale processes are not only associated with environmental concerns, but can also effect the chemical stability of the purified polypeptide conjugate. Therefore, process steps that rely on aqueous solutions are generally preferred. Hence, in one embodiment, the current invention provides methods that allow for the isolation of polypeptide conjugates essentially without the use of organic solvents.

An exemplary method of the invention involves at least one chromatographic procedure that is effective in separating polypeptide conjugates having at least one poly(alkylene oxide) moiety from other components of a mixture. The methods of the invention can be used to isolate such polypeptide conjugate from any mixture. In one example, the mixture is a reaction mixture (e.g., the product of a chemical PEGylation reaction or an ezymatically catalyzed PEGylation reaction, e.g., glycoPEGylation reaction) and may optionally include other polypeptide conjugates. Preferred methods of the invention utilize hydrophobic interaction chromatography (HIC) media. In one embodiment, HIC is used in conjunction with at least one additional chromatography step selected from anion exchange chromatography, mixed-mode chromatography, cation exchange chromatography and hydroxyapatite or fluoroapatite chromatography. In another embodiment, HIC is used in conjunction with at least one of anion exchange chromatography, mixed-mode chromatography and cation exchange chromatography. The inventors have discovered that HIC in conjunction with cation chromatography represents an efficient method for the resolution of polypeptide conjugates that include at least one poly(alkylene oxide moiety). In particular, it was discovered that HIC, followed by cation exchange can resolve EPO-PEG$_3$ species from EPO-PEG$_2$ species. In one example, HIC in conjunction with cation exchange provided a composition of purified EPO-[PEG(10 kDa)]$_3$ having a very low residual concentration of EPO-[PEG(10 kDa)]$_2$.

An exemplary method of the invention that includes anion exchange and cation exchange chromatography in addition to HIC is outlined in FIG. 1. In one embodiment, the methods of the invention are useful for the separation of different glycoforms of a polypeptide conjugate, especially those glycoforms distinguished by the number of poly(alkylene oxide) moieties that are linked to the polypeptide. Unwanted glycoforms may be formed as by-products under the reaction conditions used to form the desired polypeptide conjugate.

Hence, in a first aspect, the invention provides a method of making a composition that includes a first polypeptide conjugate, the first polypeptide conjugate having a first number of poly(alkylene oxide) moieties covalently linked to the first polypeptide. The method includes: (a) contacting a mixture containing the first polypeptide conjugate with a hydrophobic interaction chromatography (HIC) medium; and (b) eluting the first polypeptide conjugate from the HIC medium. In one example according to this aspect, the mixture includes a second polypeptide conjugate, wherein the second polypeptide conjugate has a second number of poly(alkylene oxide) moieties covalently linked to the second polypeptide, wherein the first number and the second number are different. For example, the first polypeptide conjugate includes 3 poly(alkylene oxide) moieties, while the second polypeptide conjugate includes either 0, 1, 2 or 4 poly(alkylene oxide) moieties. In one example, the poly(alkylene oxide) is poly(ethylene glycol) (PEG).

In a second aspect, the invention provides a method of isolating a first polypeptide conjugate including a first number of poly(alkylene oxide) moieties covalently linked to a first polypeptide, from a second polypeptide conjugate that includes a second number of poly(alkylene oxide) moieties covalently linked to a second polypeptide, wherein the first number is selected from 1 to 20 and the second number is selected from 0-20, the first number and the second number being different. The method includes: (a) contacting a mixture containing the first polypeptide conjugate and the second polypeptide conjugate with a hydrophobic interaction chromatography (HIC) medium; and (b) eluting the first polypeptide conjugate from said hydrophobic interaction chromatography medium. In one example according to this aspect, the first polypeptide conjugate includes 3 poly(alkylene oxide) moieties, while the second polypeptide conjugate includes 0, 1, 2, 4, 5, 6 or 7 poly(alkylene oxide) moieties.

In one example according to any of the above embodiments, the first polypeptide and the second polypeptide have the same amino acid sequence. In another example according to any of the above embodiments, both the first and the second polypeptide are EPO.

In a third aspect, the invention provides a method of forming a composition that contains a first erythropoietin (EPO) conjugate, wherein the first EPO conjugate includes a first number of poly(alkylene oxide) moieties covalently linked to an EPO polypeptide. The method includes: (a) contacting a mixture containing the first EPO conjugate with an anion exchange medium; (b) eluting the first EPO conjugate from the anion exchange medium, forming a first eluate including the first EPO conjugate; (c) contacting the first eluate with a hydrophobic interaction chromatography (HIC) medium; and (d) eluting the first EPO conjugate from the hydrophobic interaction chromatography medium. The method may further include (e.g., after step d): (e) eluting the first EPO conjugate from a cation exchange chromatography medium.

In one embodiment, the method further includes forming the polypeptide conjugate either chemically or through enzymatically catalyzed glycomodification (e.g., glycoPEGylation using a glycosyltransferase and an appropriate glycosyl donor molecule, such as a modified sugar nucleotide). GlycoPEGylation methods are art-recognized; see for example, WO 03/031464 to DeFrees et al. or WO 04/99231, the disclosures of which are incorporated herein by reference in their entirety.

The invention further provides compositions, which are made by the methods of the invention as well as pharmaceutical formulations including the composition of the invention. In addition, the invention provides methods of treatment utilizing the compositions of the invention.

Other objects and advantages of the invention will be apparent to those of skill in the art from the detailed description that follows.

DESCRIPTION OF THE DRAWINGS

FIG. 3A also includes an exemplary reaction scheme, which can be used to synthesize the EPO conjugate. The substrate for the enzymatically catalyzed conversions is an EPO polypeptide, which includes at least one glycan residue having a trimannosyl moiety. In a first step, an N-acetyl glucosamine transferase (GnT-1) is used, which adds a GlcNAc moiety to only one of the terminal mannose moieties. In the second step, a Gal moiety is linked to the newly added GlcNAc moiety using a galactosyl transferase (GalT-1) forming a terminal -GlcNAc-Gal moiety. The first and the second step maybe performed in the same reaction vessel. In the third step, a sialic acid moiety that is modified with a PEG moiety is linked to the terminal Gal moiety using a sialyl transferase (ST3Gal3).

DETAILED DESCRIPTION OF THE INVENTION

Abbreviations

Figure 1:
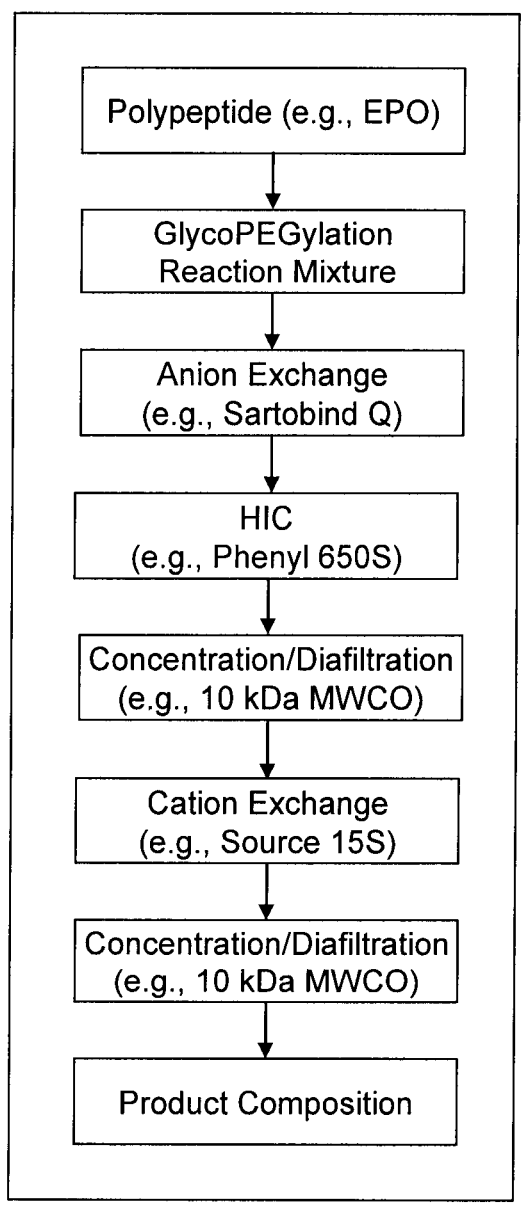
FIG. 1 is an overall view of an exemplary polypeptide conjugate purification process according to a method of the invention. The diafiltration/ultrafiltration step following hydrophobic interaction chromatography (HIC) is optional.

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; and NeuAc, sialyl (N-acetylneuraminyl); M6P, mannose-6-phosphate; BEVS, baculovirus expression vector system; CV, column volume; NTU, nominal turbidity units; vvm, volume/volume/min.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl" by itself or as part of another substituent, means, unless otherwise stated, a straight or branched chain, or cyclic (i.e., cycloalkyl)hydrocarbon radical, or combination thereof, which may be fully saturated, mono- or polyunsaturated and can include di- (e.g., alkylene) and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O) NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "acyl" describes a substituent containing a carbonyl residue, C(O)R. Exemplary species for R include H, halogen, alkoxy, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

The symbol "R" is a general abbreviation that represents a substituent group. Exemplary substituent groups include substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.) VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

As used herein, "pharmaceutically acceptable carrier" includes any material, which when combined with the conjugate retains the conjugates' activity and is non-reactive with the subject's immune systems. "Pharmaceutically acceptable carrier" includes solids and liquids, such as vehicles, diluents and solvents. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in a subject (e.g., human) that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any gramatically equivalent term means the amount that, when administered to an animal or human for treating a disease, is sufficient to effect treatment for that disease.

The term "insect cell culture" refers to the in vitro growth and culturing of cell derived from organisms of the Class Insecta. "Insect cell culture" also refers to a cell culture comprising cells of the Class Insecta which have been grown and cultured in vitro.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983). The term peptide includes molecules that are commonly referred to as proteins or polypeptides.

A "glycopeptide" as the term is used herein refers to a peptide having at least one carbohydrate moiety covalently linked thereto. It is understood that a glycopeptide may be a "therapeutic glycopeptide". The term "glycopeptide" is used interchangeably herein with the terms "glycopolypeptide" and "glycoprotein."

The term "peptide conjugate" refers to species of the invention in which a peptide is conjugated with a modified sugar as set forth herein.

As used herein, the term "modified sugar" refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "glycoconjugation" as used herein, refers to the enzymatically mediated conjugation of a modified sugar species to an amino acid or glycosyl residue of a polypeptide, e.g., an erythropoietin peptide prepared by the method of the present invention. A subgenus of "glycoconjugation" is "glyco-PEGylation," in which the modifying group of the modified sugar is poly(ethylene glycol), an alkyl derivative (e.g., m-PEG) or reactive derivative (e.g., $H_2N$-PEG, HOOC-PEG) thereof.

The terms "large-scale" and "industrial-scale" are used interchangeably and refer to a reaction cycle or process that produces at least about 250 mg, preferably at least about 500 mg, and more preferably at least about 1 gram of peptide at the completion of a single cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated polypeptide, thereby linking the modifying group to an amino acid and/or glycosyl residue of the polypeptide. A "glycosyl linking group" is generally derived from a "modified sugar" by the enzymatic attachment of the "modified sugar" to an amino acid and/or glycosyl residue of the polypeptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure. A "glycosyl linking group" may include a glycosyl-mimetic moiety. For example, the glycosyl transferase (e.g., sialyl transferase), which is used to add the modified sugar to a glycosylated polypeptide, exhibits tolerance for a glycosyl-mimetic substrate (e.g., a modified sugar in which the sugar moiety is a glycosyl-mimetic moiety—e.g., sialyl-mimetic moiety). The transfer of the modified glycosyl-mimetic sugar results in a conjugate having a glycosyl linking group that is a glycosyl-mimetic moiety.

The term "glycosyl-mimetic moiety," as used herein refers to a moiety, which structurally resembles a glycosyl moiety (e.g., a hexose or a pentose). Examples of "glycosyl-mimetic moiety" include those moieties, wherein the glycosidic oxygen or the ring oxygen of a glycosyl moiety, or both, has been replaced with a bond or another atom (e.g., sufur), or another moiety, such as a carbon- (e.g., $CH_2$), or nitrogen-containing group (e.g., NH). Examples include substituted or unsubstituted cyclohexyl derivatives, cyclic thioethers, cyclic secondary amines, moieties including a thioglycosidic bond, and the like. In one example, the "glycosyl-mimetic moiety" is transferred in an enzymatically catalyzed reaction onto an amino acid residue of a polypeptide or a glycosyl moiety of a glycopeptide. This can, for instance, be accomplished by activating the "glycosyl-mimetic moiety" with a leaving group, such as a halogen.

Figure 3A:
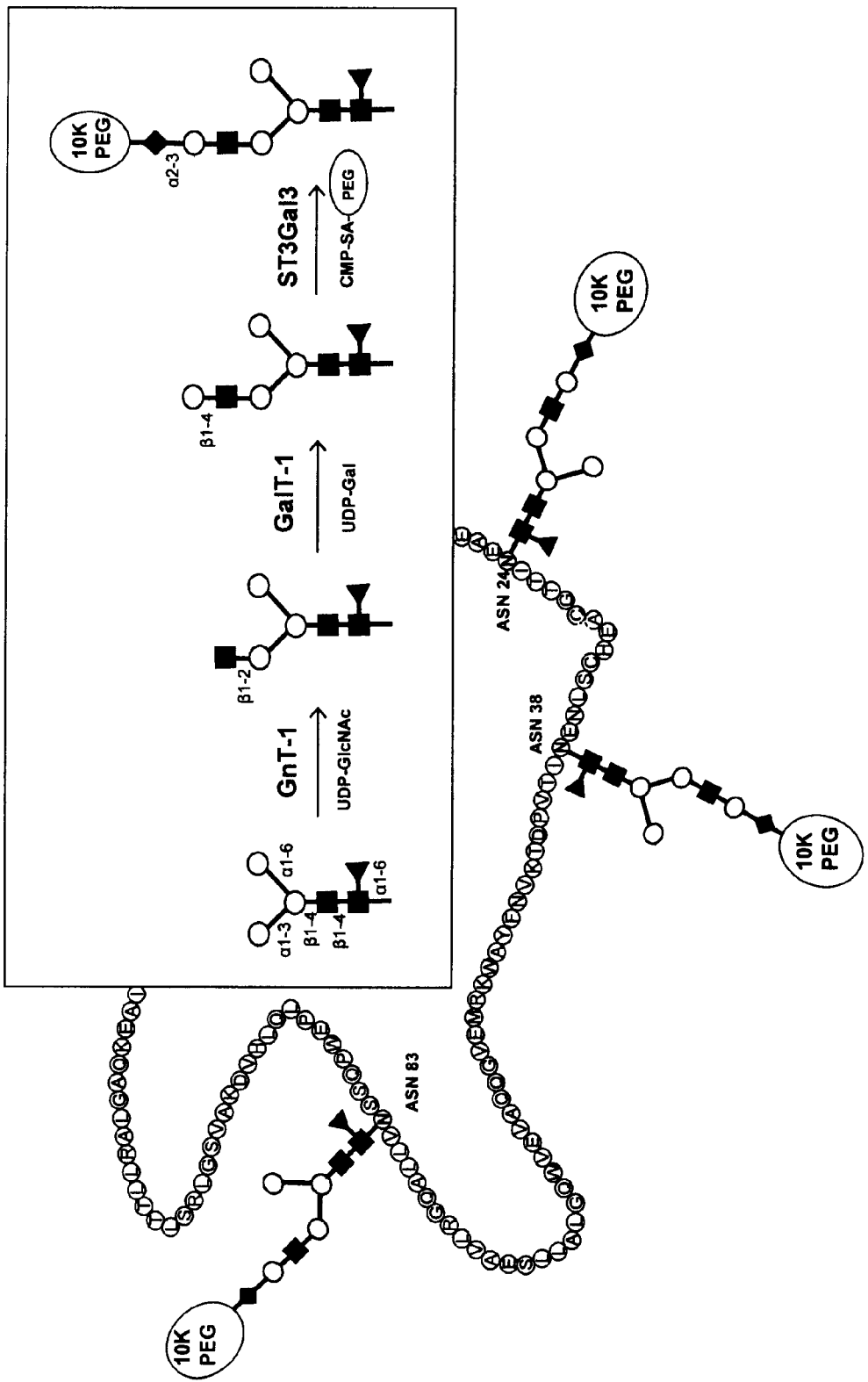
FIG. 3A is a scheme of an exemplary EPO polypeptide conjugate of the invention having an insect-specific glycosylation pattern that includes three N-linked, monoantennary glycan residues covalently linked to amino acid residues N24, N38 and N83. Each glycan residue is covalently linked to a 10 kDa PEG moiety via a terminal galactose (Gal) moiety.
Figure 3B:
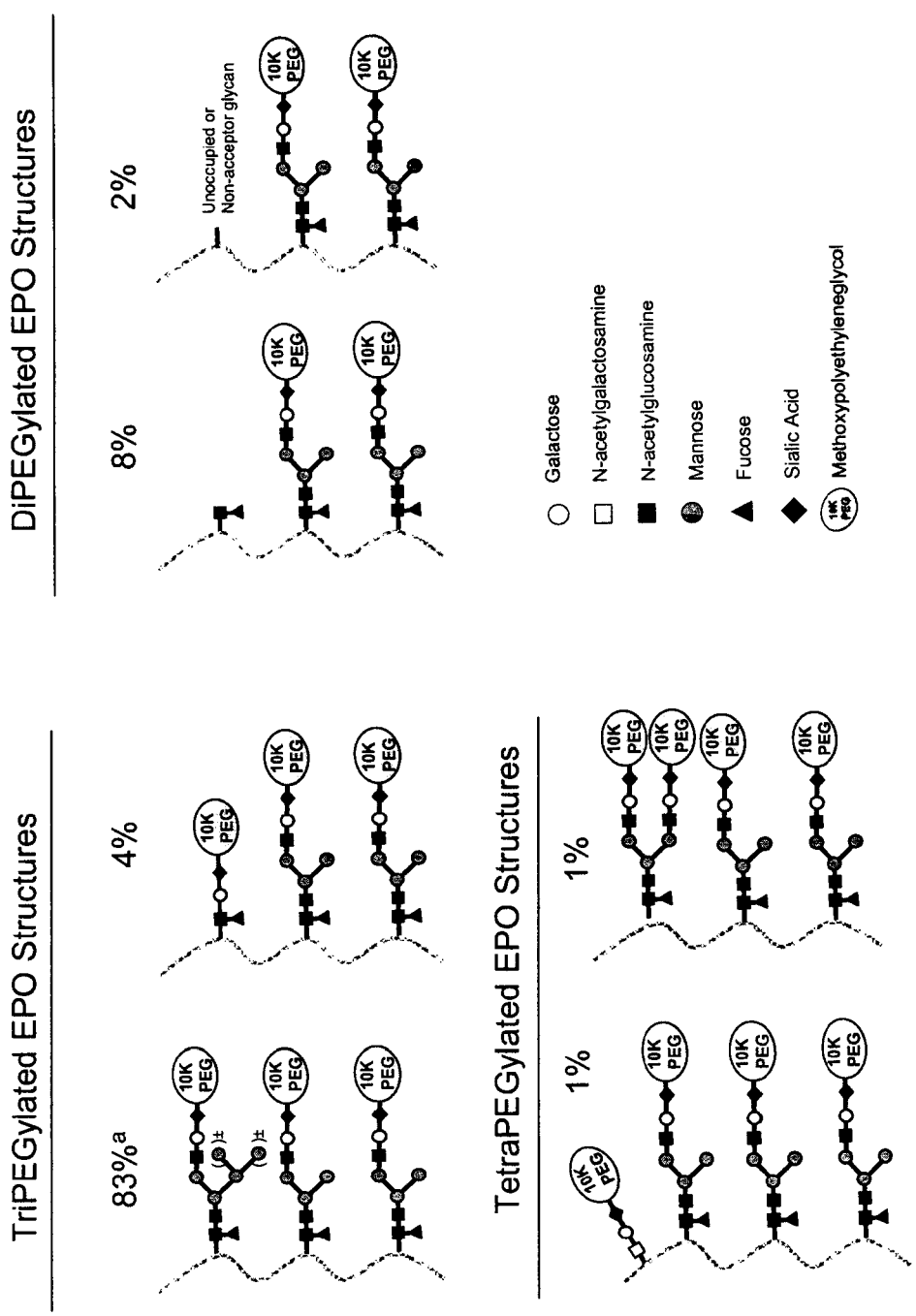
FIG. 3B is a representation of an exemplary composition of the invention that includes various glycoforms of an exemplary polypeptide conjugate (e.g., EPO conjugate). Each glycoform is distinguished from other glycoforms by the number of PEG moieties that are covalently linked to the polypeptide, or by the structure of the glycans through which the PEG moieties are linked to the polypeptide. Shown percentage values are exemplary.
Figure 5A:
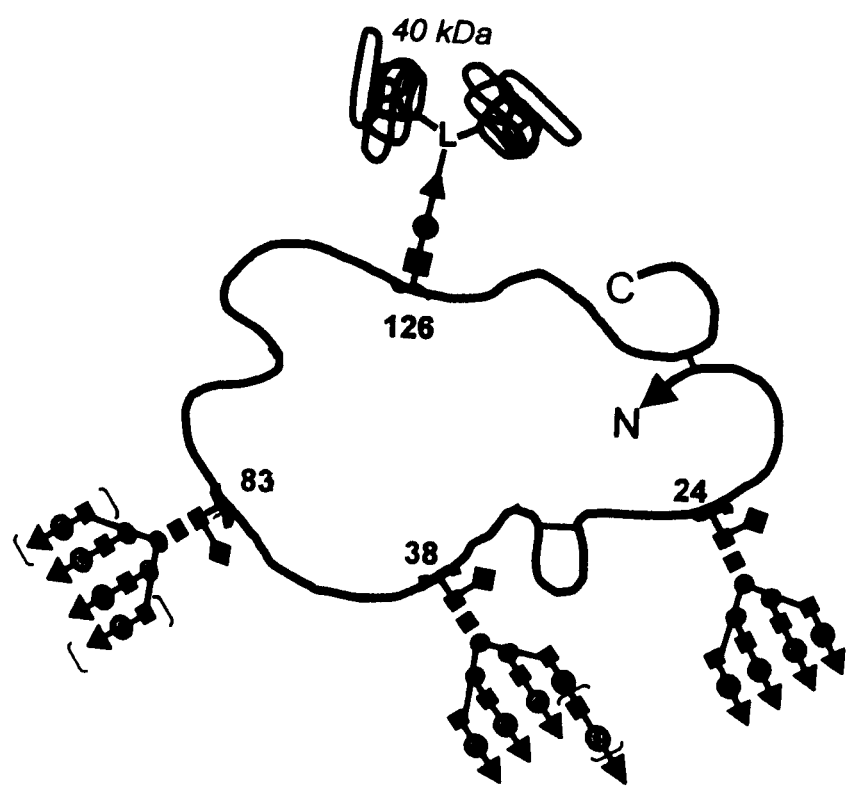
FIG. 5 is a schematic representation of exemplary glycopegylated EPO isoforms isolated from Chinese Hamster Ovary cells. A. An exemplary 40 kilodaton O-linked pegylated glycoform. B: One of several 30 kilodalton N-linked pegylated glycoforms. The modified sialic acid moiety comprising the PEG molecule may occur on any one or more of any of the branches of the N-linked glycosyl residue. Furthermore the illustration is exemplary in that any glycosylated EPO molecule may comprise any mixture of mono-, bi- tri-, or tetra-antennary N-linked glycosyl residues and any one or more of the branches may further comprise a modified sialic acid moiety.
Figure 5B:
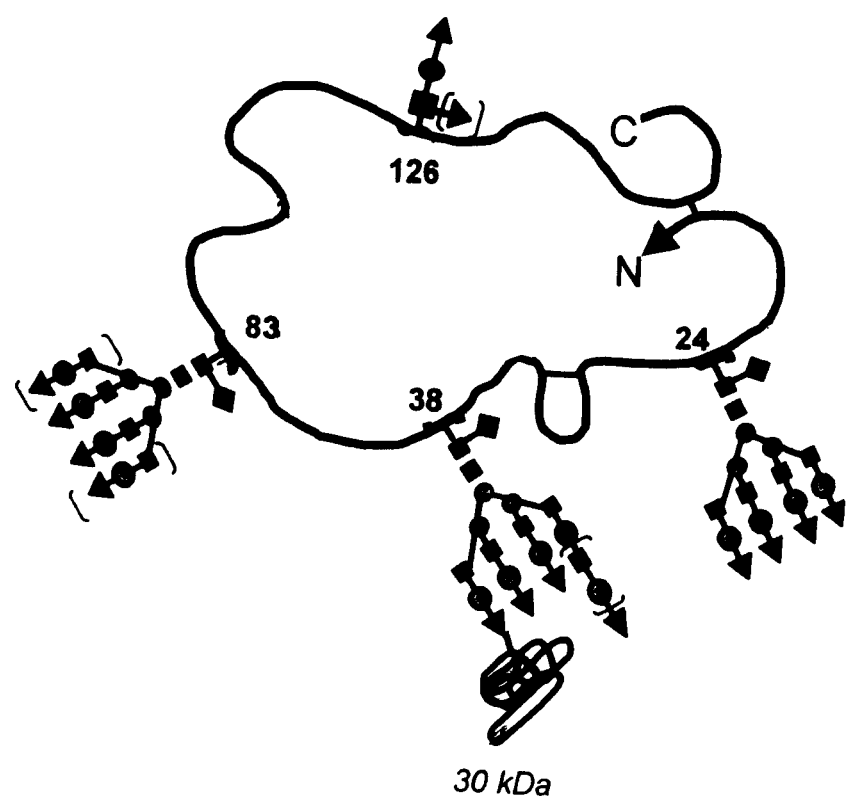

The term, "polypeptide glycoform" or "glycoform" as used herein refers to two polypeptide conjugates having the same amino acid sequence, but having a different glycosylation pattern with respect to the glycan residues to which the modifying group(s), e.g., poly(alkylene oxide) moieties, are covalently linked. Two polypeptide conjugates having a different number of modifying groups (e.g., poly(alkylene oxide) moieties) also referred to as glycoforms. FIG. 3B shows exemplary glycoforms of an EPO polypeptide conjugate. Illustrated are tri-PEGylated, di-PEGylated and tetra-PEGylated glycoforms of an EPO-PEG conjugate, wherein the EPO includes an insect-specific glycosylation pattern. Other exemplary EPO-PEG glycoforms may be derived from EPO expressed in CHO cells, as depicted in FIG. 5. Additional EPO-PEG glycoforms, which may be isolated according to the methods of the invention are disclosed in U.S. patent application Ser. No. 10/997,405 filed Nov. 24, 2004 and U.S. patent application Ser. No. 11/144,223 filed Jun. 2, 2005, the disclosures of which are disclosed herein in their entirety. EPO-PEG conjugates discussed in the Examples, below, are alternatively referred to as EPO-PEG "species", "forms" or "states".

The term "isolated" refers to a material that is essentially free from components, which are used to produce the material. For peptide conjugates of the invention, the term "isolated" refers to a material that is essentially free from components which normally accompany the material in the mixture used to prepare the peptide conjugate. The terms "isolated" and "pure" are used interchangeably. Typically, isolated peptide conjugates of the invention have a level of purity expressed as a range. For example, the lower end of the range is about 50%, about 55%, about 60%, about 65%, about 70%, about 75% or about 80% and the upper end of the range is about 55%, about 60%, about 65%, about 70%, about 75%, about 80%, about 85%, about 90%, about 95% or more than about 95%.

When the peptide conjugates are more than about 90% pure, their purities are preferably expressed as a range. For example, the lower end of the range being about 90%, about 92%, about 94%, about 96% or about 98% and the upper end of the range being about 92%, about 94%, about 96%, about 98% or about 100%.

Methods for the determination of purity are known to those of skill in the art. Purity of a polypeptide conjugate may be determined by any suitable, art-recognized method of analysis (e.g., band intensity on a silver stained gel, polyacrylamide gel electrophoresis, ELISA, HPLC and the like). An exemplary method is size-exclusion chromatography (SEC) HPLC, described herein below. Purity may be determined using relative "area under the curve" (AUC) values, which can typically be obtained for peaks in a chromatogram, such as an HPLC chromatogram. Optionally, purities are determined by chromatographic or other means using a standard curve generated using a reference material of known purity. Purity may also be determined on a weight-by-weight basis.

Methods that are useful for the determination of "purity" (e.g., those described above) are also useful for the determination of the "concentration" of a particular component in a mixture (e.g., a composition of the invention) or relative concentration of one component with respect to one or more other components. For example, SEC HPLC may be used to determine the ratio between different glycoforms or to determine the concentration of a specific glycoform in a composition of the invention.

"Essentially each member of the population" as used herein, speaks to the "homogeneity" of the sites on the peptide and to a population of peptide that share a common structure, e.g., a common glycosylation pattern/glycosyl structure.

"Homogeneity" refers to the structural consistency across a population of polypeptides. Thus, in a glycopeptide of the invention, in which each glycan residue has the same structure, the glycopeptide is said to be about 100% homogeneous. Similarly, when a in a population of glycopeptides, each glycopeptide has glycan residues of the same structure, such that each peptide of the population is essentially of the same molecular species, the population is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100%. The homogeneity of the peptide conjugates is typically determined by one or more methods known to those of skill in the art, e.g., gel electrophoresis, liquid chromatography-mass spectrometry (LC-MS), matrix assisted laser desorption mass time of flight spectrometry (MALDI-TOF), capillary electrophoresis, and the like.

"Substantially uniform glycosylation pattern," when referring to a glycopeptide species of the invention, refers to the percentage of glycosylation sites on the polypeptide that have a glycan residue of the same structure. For example a polypeptide that includes multiple N-linked or O-linked glycosylation sites may have a glycosyl residue of the same structure present at all comparable glycosylation sites, at about 90% of all comparable sites, about 80% or about 75% of all comparable glycosylation sites. In these instances the polypeptide would be said to have a "substantially uniform glycosylation pattern". Alternatively, when a population of glycopeptides share a common glycosylation pattern, the population may be said to have a "substantially uniform glycosylation pattern" when a majority of the peptides in the population represent essentially a single molecular species.

For instance, when a population of glycosylated polypeptides are isolated from a cell, without further modification, the members of the population may include a range of variations in the precise structure of their glycan residues. However, in an exemplary embodiment, peptides isolated from insect cells have a substantially uniform insect-specific glycosylation pattern. This refers to the fact that the majority of polypeptides, or substantially all of the polypeptides, in the preparation represent one distinct molecular species.

The term "substantially" in the above definitions of "substantially uniform" generally means at least about 40%, at least about 45%, at least about 50%, at least about 55%, at least about 60%, at least about 65%, at least about 70%, 71%, 72%, 73%, 74%, 75%, 76%, 77%, 78%, 79%, at least about 80%, 81%, 82%, 83%, 84%, 85%, 86%, 87%, 88%, 89%, at least about 90%, 91%, 92%, 93%, 94%, 95%, 96%, 97%, 98%, 99%, or even 100% of the acceptor moieties are glycosylated with the expected insect cell specific glycosylation pattern.

The term "insect specific glycosylation pattern" refers to the glycosylation pattern found on mature glycopeptides produced by insect cells. Typically, insect cells generate simple N-linked oligosaccharides terminating in mannose (for review, see e.g., *Essentials of Glycobiology* A. Varki et al. eds, CSHL Press (1999) pgs: 32-33). Typically, N-linked glycans produced by insect cell lines produce glycoproteins that (at maturity) include a $Man_3GlcNAc_2$ structure. Fucose units may also be found on the GlcNAc residue that is directly linked to the peptide. A mature peptide emerging from a cell with an "insect specific glycosylation pattern" thus includes one or more glycans having a trimannosyl ($Man_3$) or $Man_3GlcNAc_2$ structure. "Insect specific glycosylation pattern" also refers to polypeptide populations, in which essentially all of the polypeptides have glycan structures terminating with a common motiv (e.g., the $Man_3$ or $Man_3GlcNAc_2$ motiv) and are not degraded, e.g., to expose one of the two GlcNAc residues directly bound to the polypeptide.

The term "loading buffer" refers to the buffer, in which the polypeptide conjugate being purified is applied to a purification device, e.g. a chromatography column or a filter cartridge. Typically, the loading buffer is selected so that separation of the peptide conjugate of interest from unwanted impurities can be accomplished. For instance, when purifying the polypeptide conjugate on a hydroxyapatite (HA) or fluoroapatite column the pH of the loading buffer and the salt concentration in the loading buffer may be selected so that the polypeptide conjugate is initially retained on the column while certain impurities are found in the flow through. In other example, the loading buffer is selected to retain impurities while the desired polypeptide conjugate is found in the flow-through.

The term "elution buffer" refers to the buffer, which is typically used to remove (elute) the polypeptide conjugate from the purification device (e.g. a chromatographic column or filter cartridge) to which it was applied earlier. Typically, the elution buffer is selected so that separation of the polypeptide conjugate of interest from unwanted impurities can be accomplished. Often, the concentration of a particular ingredient, such as a particular salt (e.g. NaCl) in the elution buffer is varied during the elution procedure (gradient). The gradient may be continuous or stepwise (interrupted by hold periods).

The term "controlled room temperature" refers to a temperature of at least about 10° C., at least about 15° C., at least about 20° C. or at least about 25° C. Typically, controlled room temperature is between about 20° C. and about 25° C.

I. The Methods

The present invention provides processes for the isolation (e.g., large-scale isolation) of polypeptide conjugates from a mixture. The polypeptide conjugates isolated by the methods of the invention include at least one modifying group. Exemplary modifying groups include polymers, such as poly(alkylene oxide) moieties (e.g., poly(ethylene glycol) or poly(propylene glycol)). Exemplary modifying groups are described herein, below.

In one embodiment, the polypeptide conjugate is isolated from a reaction mixture. In one example, the reaction mixture is the product of a chemical reaction, such as a chemical PEGylation reaction. In one example according to this embodiment, the reaction mixture may contain chemicals, such as unreacted polymeric reagents and/or hydrolysis products thereof. In another example, the reaction mixture is the product of an enzymatically catalyzed reaction, such as an enzymatically catalyzed glycoPEGylation reaction. In this instance, the reaction mixture may include enzymes, and may further include reagents, such as unreacted enzyme substrates (e.g., nucleotide sugars and the like). In one example, the methods of the invention are suitable for the isolation of a polypeptide conjugate from the above listed reaction mixture components.

In another embodiment, the methods of the invention are useful to isolate a desired polypeptide conjugate from a mixture that includes other polypeptide conjugates, which are sought to be separated from the desired polypeptide conjugate. Such "unwanted" polypeptide conjugates or side-products may be generated during the same reaction that leads to the formation of the desired polypeptide conjugate. For example, a recombinant polypeptide is subjected to a chemical PEGylation reaction. The reaction product includes different polypeptide conjugates, in which each type of polypeptide conjugate includes a different number of PEG moieties, e.g., the majority of the polypeptide conjugates includes three PEG moieties, while a small percentage of the polypeptide conjugates in the reaction mixture is covalently linked to only one or two PEG moieties. In another example, a recombinantly produced polypeptide is subjected to an enzymatically catalyzed glycoPEGylation reaction. Due to a heterogenous glycosylation pattern of the polypeptide population used in the reaction, the reaction mixture includes different polypeptide conjugates, in which each type of polypeptide conjugate has a different structure with respect to the number of PEG moieties covalently linked to the polypeptide and/or the structure of the glycan residues, to which each PEG moiety is attached to the polypeptide. The mixture may also contain unreacted polypeptide.

The inventors have discovered that hydrophobic interaction chromatography (HIC) resins, such as butyl and phenyl resins (e.g., Phenyl 650S) are particularly useful for the isolation of polypeptides modified with at least one poly(alkylene oxide) moiety. In particular, it has become apparent that HIC is superior in separating different glycoforms of a polypeptide conjugate, especially glycoforms that are distinguished by the number of poly(alkylene oxide) moieties that are linked to the polypeptide.

For example, HIC is efficient in separating an erythropoietin (EPO) conjugate that includes three poly(ethylene glycol) (PEG) moieties from other EPO conjugates that include 0, 1, 2, 4, 5, 6 or 7 PEG moieties. In addition, HIC can be used to separate polypeptide conjugates that include the same number of poly(alkylene oxide) moieties, but wherein the polypeptide conjugates have a different glycosylation pattern.

In addition to hydrophobic interaction chromatography, the methods of the invention may further employ additional chromatographic steps. In one embodiment, the method includes anion exchange or mixed-mode chromatography in addition to HIC. In another embodiment, the method includes cation exchange chromatography in addition to HIC. In yet another embodiment, the method includes both, anion exchange or mixed-mode chromatography and cation exchange chromatography in addition to HIC. In a further embodiment, the method includes hydroxyapatite or fluoroapatite chromatography in addition to HIC. The chromatographic steps employed in the methods of the invention can be performed in any desired order. In one embodiment, anion exchange or mixed-mode chromatography is performed prior to hydrophobic interaction chromatography. In another embodiment, anion exchange or mixed-mode chromatography is performed after hydrophobic interaction chromatography. In yet another embodiment, cation exchange chromatography is performed prior to hydrophobic interaction chromatography. In a further embodiment, cation exchange chromatography is performed after hydrophobic interaction chromatography. In one embodiment, hydroxyapatite or fluoroapatite chromatography is performed prior to HIC. In another embodiment, hydroxyapatite or fluoroapatite chromatography is performed after HIC.

Hence, in a first aspect, the invention provides a method of making a composition that includes a first polypeptide conjugate, wherein the first polypeptide conjugate includes a first number of poly(alkylene oxide) moieties covalently linked to a first polypeptide. The method includes: (a) contacting a mixture containing the first polypeptide conjugate with a hydrophobic interaction chromatography (HIC) medium; and (b) eluting the first polypeptide conjugate from the HIC medium. The method may further include: (c) eluting the first polypeptide conjugate from an anion exchange or mixed-mode chromatography medium. In one embodiment, step (c) is performed prior to step (a). In another embodiment, step (c) is performed after step (b). The method may further include: (d) eluting the first polypeptide conjugate from a cation exchange chromatography medium. In one embodiment, step (d) is performed prior to step (a). In another embodiment, step (d) is performed after step (b).

In one embodiment according to this aspect, the mixture includes additional polypeptide conjugates, from which the first polypeptide conjugate is isolated. In an exemplary embodiment, the mixture includes a second polypeptide conjugate, wherein the second polypeptide conjugate has a second number of poly(alkylene oxide) moieties covalently linked to a second polypeptide. In one example, the first polypeptide and the second polypeptide have the same amino acid sequence. In another example, the first polypeptide and the second polypeptide have a different amino acid sequence. In one example, the first number and the second number are different, which means that the first polypeptide conjugate and the second polypeptide conjugate are distinguished by the number of poly(alkylene oxide) moieties that are linked to each polypeptide. For example, the first polypeptide conjugate includes 3 poly(alkylene oxide) moieties, while the second polypeptide conjugate includes either 0, 1, 2 or 4 poly(alkylene oxide) moieties. In one particular example, the first polypeptide and the second polypeptide have the same amino acid sequence and the first polypeptide conjugate and the second polypeptide conjugate are distinguished by a different number of poly(alkylene oxide) moieties (first number and second number are different).

In one example, according to any of the above embodiments, the method of the invention is useful to provide a composition including a first polypeptide conjugate, wherein the concentration of the second polypeptide conjugate in this composition is less than about 30%, less than about 25%, less than about 20%, less than about 15% and preferably less than about 10%, less than about 9%, less than about 8%, less than about 7%, less than about 6%, less than about 5%, less than about 4%, less than about 3%, less than about 2% or less than about 1%. In another embodiment, the mixture includes more than one glycoform of the first polypeptide conjugate and the method provides a composition, in which the combined concentration of all glycoforms having a structure distinct from the first polypeptide conjugate is less than about 30%, less than about 25%, less than about 20%, less than about 15% and preferably less than about 10%, less than about 9%, less than about 8%, less than about 7%, less than about 6%, less than about 5%, less than about 4%, less than about 3%, less than about 2% or less than about 1%.

In one example according to any of the above embodiments, the first polypeptide is a glycopeptide and comprises a first glycosylation pattern that includes at least one glycan residue covalently linked to the first polypeptide. Each glycan residue can be linked to at least one polymeric modifying group, such as a poly(alkylene oxide) moiety. In another example according to the above embodiments, the first polypeptide includes a first number of poly(alkylene oxide) moieties, each of which is covalently linked to the first polypeptide via an N-linked or O-linked glycan.

In yet another embodiment, the method of the invention is useful to separate two polypeptide glycoforms that may include the same number of modifying groups, but that have different glycosylation patterns. Hence, in one example, the mixture from which the first polypeptide is isolated, includes a third polypeptide conjugate that includes a third number of poly(alkylene oxide) moieties. In one example, the third polypeptide conjugate and the first polypeptide conjugate include the same number of poly(alkylene oxide) moieties, but the third polypeptide has a glycosylation pattern that differs from the glycosylation pattern of the first polypeptide conjugate by at least one glycosyl moiety. For example, the third polypeptide conjugate includes a glycan residue that is not present in the first polypeptide conjugate. In an exemplary embodiment, the third polypeptide includes an O-linked glycan, while the first polypeptide includes only N-linked glycans (see, e.g., FIG. 3B, tri-PEGylated EPO structures). In another exemplary embodiment, the third polypeptide includes a truncated glycan residue, while the corresponding glycan residue of the first polypeptide conjugate is intact (i.e., includes a larger number of glycosyl moieties).

In a second aspect, the invention provides a method of isolating a first polypeptide conjugate including a first number of poly(alkylene oxide) moieties covalently linked to a first polypeptide, from a second polypeptide conjugate that includes a second number of poly(alkylene oxide) moieties covalently linked to a second polypeptide. The method includes: (a) contacting a mixture containing the first polypeptide conjugate and the second polypeptide conjugate with a hydrophobic interaction chromatography (HIC) medium; and (b) eluting the first polypeptide conjugate from said hydrophobic interaction chromatography medium. The method may further include: (c) eluting the first polypeptide conjugate from an anion exchange chromatography medium. In one embodiment step (c) is performed prior to step (a). In another embodiment, step (c) is performed after step (b). The method may further include: (d) eluting the first polypeptide conjugate from a cation exchange chromatography medium. In one embodiment, step (d) is performed prior to step (a). In another embodiment, step (d) is performed after step (b).

In one example according to any of the above embodiments, the first number of poly(alkylene oxide) moieties that are linked to the first polypeptide is selected from 1 to about 40. In another example, the first number is selected from 1 to about 30. In yet another example, the first number is selected from 1 to about 20. In a further example, the first number is selected from 1, 2, 3, 4, 5, 6, 7, 8, 9 and about 10. In another example, the first polypeptide conjugate includes exactly three poly(alkylene oxide) moieties.

In one example according to any of the above embodiments, the second number of poly(alkylene oxide) moieties that are linked to the second polypeptide is selected from 0 to about 40. In another example, the second number is selected from 0 to about 30. In yet another example, the second number is selected from 0 to about 20. In a further example, the second number is selected from 0, 1, 2, 3, 4, 5, 6, 7, 8, 9 and about 10. In another example, the first number and the second number are different. For example, the first polypeptide conjugate includes 3 poly(alkylene oxide) moieties, while the second polypeptide conjugate includes either 0, 1, 2 or 4 poly(alkylene oxide) moieties. One of skill will understand that a polypeptide that is not linked to a poly(alkylene oxide) moiety (second number=0), represents unreacted polypeptide and is not technically a conjugate unless it contains other modifying groups.

In one example according to any of the above embodiments, the first polypeptide and the second polypeptide have the same amino acid sequence. In another example according to any of the above embodiments, the first polypeptide is a therapeutic polypeptide. Exemplary therapeutic polypeptides are described herein, below. In yet another example according to any of the above embodiments, the first polypeptide is EPO. In another example according to any of the above embodiments, both the first polypeptide and the second polypeptide are EPO. In yet another example, both the first polypeptide and the third polypeptide are EPO.

In one embodiment of the invention, the first polypeptide conjugate is formed by an enzymatically catalyzed glycomodification reaction, during which a modified glycosyl moiety [e.g., a glycosyl moiety modified with at least one poly(alkylene oxide) moiety] is covalently linked to the first polypeptide. Hence, in one example according to any of the above embodiments, the method of the invention may further include: contacting the first polypeptide and a modified glycosyl donor species (e.g., a modified sugar nucleotide) having a glycosyl moiety covalently linked to a polymer (e.g., a poly(alkylene oxide) moiety), in the presence of an enzyme (e.g., a glycosyltransferase), for which the modified glycosyl donor species is a substrate, under conditions sufficient for the enzyme to catalyze the formation of a covalent bond between the glycosyl moiety that is linked to the polymer and the first polypeptide. In one example, the modified glycosyl moiety is a sialic acid (SA) moiety. In one example, the enzyme is a sialyltransferase. In another example, the polymer is PEG (e.g., m-PEG). GlycoPEGylation methods are art-recognized; see for example, WO 03/031464 to DeFrees et al. or WO 04/99231, the disclosures of which are incorporated herein by reference in their entirety.

In one example according to any of the above embodiments, the method of the invention may further include: recombinantly expressing the first polypeptide in a host cell, such as an insect cell, a mammalian cell (e.g., a CHO cell) or a fungal cell (e.g., yeast cell). In one example, the first polypeptide is expressed in an insect cell line (e.g., a *Spodoptera frugiperda* cell, e.g., Sf9).

The first polypeptide may be further modified (e.g., through glycan remodeling) to include a substantially uniform (e.g., insect-specific) glycosylation pattern. The glycosylation pattern of the peptides can be elaborated, trimmed back or otherwise modified by methods utilizing enzymes. The methods of remodeling peptides using enzymes that transfer a sugar donor to an acceptor are discussed in detail in WO 03/031464 to De Frees et al. (published Apr. 17, 2003); U.S. Patent Application 20040137557 (filed Nov. 5, 2002); U.S. Patent Application 20050143292 (filed Nov. 24, 2004) and WO 05/051327 (filed Nov. 24, 2004), each of which is incorporated herein by reference in its entirety.

Hence, in one embodiment, the method of the invention may further include: contacting the first polypeptide and a glycosyl donor molecule (e.g., a nucleotide sugar) in the presence of an enzyme for which the glycosyl donor molecule is a substrate, under conditions sufficient for the enzyme to form a covalent bond between a glycosyl moiety of the glycosyl donor molecule and the first polypeptide. The polypeptide used as a substrate in this reaction may be glycosylated or non-glycosylated. The enzyme may be a glycosyltransferase, such as a GlcNAc-transferase, a GalNAc-transferase, a Gal-transferase or a sialyltransferase.

Thus, in one example, the method of the invention includes: contacting a glycosylated or non-glycosylated first polypeptide and a nucleotide-N-acetylglucosamine (GlcNAc) or a nucleotide-N-acetylgalactosamine (GalNAc) molecule in the presence of a N-acetylglucosamine transferase (e.g., GnT1 or GnT2) or a N-acetylgalactosamine transferase, respectively. The reaction mixture may further include a nucleotide galactose (Gal) molecule, and a galactosyl transferase (e.g., GalT1). The components of the reaction mixture are contacted (e.g., in a single reaction vessel or sequentially) under conditions sufficient for the N-acetylglucosamine transferase and the galactosyl transferase to form a glycosylated first polypeptide having at least one glycan residue with a terminal -GlcNAc-Gal moiety or a -GalNAc-Gal moiety. That glycan residue is preferably mono-antennary with respect to the newly added -GlcNAc-Gal or -GalNAc-Gal moiety. In one embodiment, the -GlcNAc-Gal moiety is added to a mannose residue, which is part of a tri-mannosyl motif. In another embodiment, the -GalNAc-Gal moiety is added to a serine or threonine residue of the first polypeptide.

In a third aspect, the invention provides a method of making a composition that contains a first erythropoietin (EPO) conjugate, wherein the first EPO conjugate includes a first number of poly(alkylene oxide) moieties covalently linked to an EPO polypeptide. The method includes: (a) contacting a mixture containing the first EPO conjugate with an anion exchange medium; (b) eluting the first EPO conjugate from the anion exchange medium, forming a first eluate including the first EPO conjugate; (c) contacting the first eluate with a hydrophobic interaction chromatography (HIC) medium; and (d) eluting the first EPO conjugate from the hydrophobic interaction chromatography medium. The method may further include: (e) eluting the first EPO conjugate from a cation exchange chromatography medium. In one example, step (e) is performed after step (d). In another example, step (e) is performed prior to step (c). The method may further include one or more dilution or diafiltration steps. In one example, diafiltration is used to concentrate and/or exchange the buffer in order to condition the sample for the next process step. For example, the eluate from the HIC step is concentrated and diafiltered into a new buffer system in order to prepare the sample for cation exchange chromatography.

In one embodiment according to this aspect, the mixture includes additional EPO conjugates, from which the first EPO conjugate is isolated. In an exemplary embodiment, the mixture includes a second EPO conjugate having a second number of poly(alkylene oxide) moieties covalently linked to an EPO polypeptide. In one embodiment, the first number and the second number are different, which means that the first EPO conjugate and the second EPO conjugate are glycoforms distinguished by the number of poly(alkylene oxide) moieties that are linked to each EPO polypeptide. For example, the first EPO conjugate includes 3 poly(alkylene oxide) moieties, while the second EPO conjugate may include 0, 1, 2 or 4 poly(alkylene oxide) moieties. In one example, the method is useful to provide a composition including a first EPO conjugate, wherein the concentration of the second EPO conjugate in this composition is less than about 30%, less than about 25%, less than about 20%, less than about 15% and preferably less than about 10%, less than about 9%, less than about 8%, less than about 7%, less than about 6%, less than about 5%, less than about 4%, less than about 3%, less than about 2% or less than about 1%. In another embodiment, the mixture includes more than one glycoform of the first EPO conjugate and the method provides a composition, in which the combined concentration of all glycoforms having a structure distinct from the structure of the first EPO conjugate is less than about 30%, less than about 25%, less than about 20%, less than about 15% and preferably less than about 10%, less than about 9%, less than about 8%, less than about 7%, less than about 6%, less than about 5%, less than about 4%, less than about 3%, less than about 2% or less than about 1%.

An exemplary EPO sequence useful in conjunction with any of the above embodiments, is represented by SEQ ID NO:1, which may include at least one mutation (eg., $Arg^{139}$ to $Ala^{139}$, $Arg^{143}$ to $Ala^{143}$ and $Lys^{154}$ to $Ala^{154}$) In another exemplary embodiment, the EPO conjugates of the invention may include at least one N-linked glycan residue. In one example, the N-linked glycan residue is covalently linked to an amino acid residue selected from $Asn^{24}$, $Asn^{38}$ and $Asn^{83}$ of SEQ ID NO:1. The EPO conjugate may further include an O-linked glycan residue. In one example, the O-linked glycan residue is covalently linked to a serine (e.g., Ser 126) residue of SEQ ID NO:1. Any of the above described glycan residues can optionally be linked to a poly(alkylene oxide) moiety. In one example according to any of the above embodiments, EPO is covalently linked to three poly(alkylene oxide) moieties (e.g., three PEG moieties). In another example according to any of the above embodiments, EPO is covalently linked to three poly(alkylene oxide) moieties (e.g., PEG), wherein at least two of the three poly(alkylene oxide) moieties are covalently linked to the EPO polypeptide via N-linked glycans. In one example, at least one N-linked glycan is mono-antennary. In another example, all three N-linked glycans are mono-antennary (e.g., as shown in FIG. 3A). Exemplary tri-PEGylated EPO conjugates are shown in FIG. 3B.

In one embodiment, the EPO conjugate is formed by an enzymatically catalyzed glycomodification reaction, wherein a modified glycosyl moiety (e.g., a glycosyl moiety modified with at least one poly(alkylene oxide) moiety) is attached to the EPO polypeptide. Hence, in one example according to any of the above embodiments, the method of the invention may further include: contacting an EPO polypeptide and a modified glycosyl donor species (e.g., a modified sugar nucleotide) having a glycosyl moiety covalently linked to a polymer (e.g., a poly(alkylene oxide) moiety), in the presence of an enzyme (e.g., a glycosyltransferase), for which the modified glycosyl donor species is a substrate, under conditions sufficient for the enzyme to catalyze the formation of a covalent bond between the glycosyl moiety that is linked to the polymer and the EPO polypeptide. In one example, the modified glycosyl moiety is a sialic acid (SA) moiety. In another example, the enzyme is a sialyltransferase. The method may further include: recombinantly expressing the EPO polypeptide in a host cell, such as a bacterial (e.g., *E. coli*), an insect cell, a mammalian cell (e.g., CHO) cell or a fungal cell. In one example, the EPO polypeptide is expressed in an insect cell line (e.g., Sf9) and is optionally purified from insect cell culture, e.g., according to the methods outlined in WO 06/105426 to Kang et al.

The EPO peptide may be further modified through glycan remodeling to include a substantially uniform (e.g., insect-specific) glycosylation pattern. Hence, in one embodiment, the method of the invention may further include: contacting (e.g., in a single reaction vessel) a glycosylated EPO polypeptide with a nucleotide-N-acetylglucosamine (GlcNAc) molecule and a nucleotide galactose (Gal) molecule in the presence of a N-acetylglucosamine transferase (e.g., GnT1 or GnT2), and a galactosyl transferase (e.g., GalT1), under conditions sufficient for said N-acetylglucosamine transferase and said galactosyl transferase to form a glycosylated EPO polypeptide having at least one glycan residue with a terminal -GlcNAc-Gal moiety. That glycan residue is preferably mono-antennary with respect to the newly added -GlcNAc-Gal moiety. In one embodiment, the -GlcNAc-Gal moiety is added to a mannose residue, which is part of a tri-mannosyl motive.

In one example according to any of the above embodiments, each poly(alkylene oxide) moiety is a member independently selected from poly(ethylene glycol) (e.g., m-PEG) and poly(propylene glycol) (e.g., m-PPG). Exemplary poly(ethylene glycol) moieties are described herein, below. In another example according to any of the above embodiments, each poly(alkylene oxide) moiety has an independently selected molecular weight between about 1 kDa and about 200 kDa. Additional molecular weight ranges for poly(alkylene oxide) moieties are given herein, below.

In one example according to any of the above embodiments, the first polypeptide conjugate includes at least one poly(alkylene oxide) moiety that is covalently linked to the first polypeptide via a glycosyl linking group. In one example, the glycosyl linking group is covalently linked to an amino acid residue of the first polypeptide. In another example, the glycosyl linking group is covalently linked to a glycosyl moiety of said first polypeptide. In yet another example, the glycosyl linking group is an intact glycosyl linking group. Exemplary glycosyl linking groups are described herein and, for example, in WO 03/031464 to DeFrees et al., WO 04/99231, and PCT/US07/74139 filed Jul. 23, 2007, the disclosures of which are incorporated herein by reference in their entirety. Exemplary intact glycosyl linking groups include sialic acid moieties, GlcNH and GlcNAc moieties, as well as Gal, GalNH and GalNAc moieties.

Exemplary HIC media that are useful in any of the above described embodiments, include butyl and phenyl resins, such as Phenyl 650S (e.g., ToyoPearl). Hydrophobic interaction chromatography and suitable HIC media are described herein below and, for example in *Process Scale Bioseparations for the Biopharmaceutical Industry*, Ed. Shukla A A, Etzel M R, Gadam S, CRC Press Taylor & Francis Group (2007), pages 197-206, the disclosure of which is incorporated herein by reference.

Those of skill in the art will appreciate that the methods of the invention can be practiced for polypeptide conjugates based on a wide variety of polypeptides. The methods are not limited to a particular polypeptide. Hence, any of the above described embodiments of the invention can be practiced with any of the below described polypeptide conjugates.

I.a) Polypeptide Conjugates

The polypeptide conjugates isolated by the methods of the invention include a polypeptide and at least one modifying group covalently linked to the polypeptide, e.g., via a glycosyl linking group. Exemplary polypeptide conjugates are discussed herein below and, for example WO 03/031464 to DeFrees et al., WO 04/99231 to DeFrees et al., and WO 04/33651 to DeFrees et al., the disclosures of which are incorporated herein by reference in their entirety.

Polypeptides

The polypeptide that is part of polypeptide conjugates of the invention can be any glycosylated or non-glycosylated polypeptide. In one embodiment, the polypeptide is a recombinant polypeptide. In one example according to this embodiment, the polypeptide is expressed in a host cell selected from bacterial cells (e.g., *E. coli*), insect cells (e.g., *Spodoptera frugiperda* cells), fungal cells (e.g., yeast cells), mammalian cells (e.g., CHO cells) and bacterial cells (e.g., *E. coli* cells). Methods for the expression of polypeptides in insect cell lines are discussed herein below. In another embodiment, the polypeptide is chemically synthesized and optionally includes non-natural amino acids.

The polypeptide can have any number of amino acids. In one embodiment, the peptide or glycopeptide has a molecular weight of about 5 kDa to about 500 kDa. In another embodiment, the peptide or glycopeptide has a molecular weight of about 10 kDa to about 100 kDa. In yet another embodiment, the polypeptide has a molecular weight of about 10 kDa to about 30 kDa. In a further embodiment, the polypeptide has a molecular weight of about 20 kDa to about 25 kDa.

Exemplary polypeptides include wild-type polypeptides and fragments thereof as well as polypeptides, which are modified from their naturally occurring counterpart (e.g., by mutation or truncation). A polypeptide may also be a fusion protein. Exemplary fusion proteins include those, in which the polypeptide is fused to a fluorescent protein (e.g., GFP), a therapeutic polypeptide, an antibody, a receptor ligand, a proteinaceous toxin, MBP, a Histag and the like.

In one embodiment, the polypeptide is a therapeutic polypeptide (i.e., authorized drug), such as those currently used as pharmaceutical agents. A non-limiting selection of polypeptides is shown in FIG. 28 of U.S. patent application Ser. No. 10/552,896 filed Jun. 8, 2006, which is incorporated herein by reference.

Exemplary polypeptides include growth factors, such as fibroblast growth factors (e.g., FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22 and FGF-23), blood coagulation factors (e.g., Factor V, Factor VII, Factor VIII, B-domain deleted Factor VIII, partial B-domain deleted Factor VIII, vWF-Factor VIII fusion (e.g., with full-length or B-domain deleted Factor VIII), Factor IX, Factor X and Factor XIII), hormones, such as human growth hormone (hGH) and follicle stimulating hormone (FSH), as well as cytokines, such as interleukins (e.g., IL-1, IL-2, IL-12) and interferons (e.g., INF-alpha, INF-beta, INF-gamma).

Other exemplary polypeptides include enzymes, such as glucocerebrosidase, alpha-galactosidase (e.g., Fabrazyme™), acid-alpha-glucosidase (acid maltase), alpha-L-iduronidase (e.g., Aldurazyme™), thyroid peroxidase (TPO), beta-glucosidase (see e.g., enzymes described in U.S. patent application Ser. No. 10/411,044), and alpha-galactosidase A (see e.g., enzymes described in U.S. Pat. No. 7,125,843).

Other exemplary parent polypeptides include bone morphogenetic proteins (e.g., BMP-1, BMP-2, BMP-3, BMP-4, BMP-5, BMP-6, BMP-7, BMP-8, BMP-9, BMP-10, BMP-11, BMP-12, BMP-13, BMP-14, BMP-15), neurotrophins (e.g., NT-3, NT-4, NT-5), erythropoietins (EPO), growth differentiation factors (e.g., GDF-5), glial cell line-derived neurotrophic factor (GDNF), brain derived neurotrophic factor (BDNF), nerve growth factor (NGF), von Willebrand factor (vWF), vWF protease, granulocyte colony stimulating factor (G-CSF), granulocyte-macrophage colony stimulating factor (GM-CSF), $\alpha_1$-antitrypsin (ATT, or $\alpha$-1 protease inhibitor), tissue-type plasminogen activator (TPA), hirudin, leptin, urokinase, human DNase, insulin, hepatitis B surface protein (HbsAg), human chorionic gonadotropin (hCG), chimeric diphtheria toxin-IL-2, glucagon-like peptides (e.g., GLP-1 and GLP-2), anti-thrombin III (AT-III), prokinetisin, CD4, $\alpha$-CD20, tumor necrosis factor receptor (TNF-R), P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein and extendin-4. Exemplary amino acid sequences for some of the above listed polypeptides are described in U.S. Pat. No. 7,214,660, all of which are incorporated herein by reference.

In an exemplary embodiment, the polypeptide is EPO comprising the amino acid sequence of (SEQ ID NO:1), which is shown below:

Ala Pro Pro Arg Leu Ile Cys Asp Ser Arg Val Leu

Glu Arg Tyr Leu Leu Glu Ala Lys Glu Ala Glu Asn$^{24}$

Ile Thr Thr Gly Cys Ala Glu His Cys Ser Leu Asn

Glu Asn$^{38}$ Ile Thr Val Pro Asp Thr Lys Val Asn Phe

Tyr Ala Trp Lys Arg Met Glu Val Gly Gln Gln Ala

Val Glu Val Trp Gln Gly Leu Ala Leu Leu Ser Glu

Ala Val Leu Arg Gly Gln Ala Leu Leu Val Asn$^{83}$ Ser

Ser Gln Pro Trp Glu Pro Leu Gln Leu His Val Asp

Lys Ala Val Ser Gly Leu Arg Ser Leu Thr Thr Leu

Leu Arg Ala Leu Gly Ala Gln Lys Glu Ala Ile Ser

Pro Pro Asp Ala Ala Ser$^{126}$ Ala Ala Pro Leu Arg Thr

Ile Thr Ala Asp Thr Phe Arg Lys Leu Phe Arg Val

Tyr Ser Asn Phe Leu Arg Gly Lys Leu Lys Leu Tyr

Thr Gly Glu Ala Cys Arg Thr Gly Asp

Also within the scope of the invention are polypeptides that are antibodies. The term antibody is meant to include antibody fragments (e.g., Fc domains), single chain antibodies, Lama antibodies, nano-bodies and the like. Also included in the term are antibody-fusion proteins, such as Ig chimeras. Preferred antibodies include humanized, monoclonal antibodies or fragments thereof. All known isotypes of such antibodies are within the scope of the invention. Exemplary antibodies include those to growth factors, such as endothelial growth factor (EGF), vascular endothelial growth factors (e.g., monoclonal antibody to VEGF-A, such as ranibizumab (Lucentis™)) and fibroblast growth factors, such as FGF-7, FGF-21 and FGF-23) and antibodies to their respective receptors. Other exemplary antibodies include anti-TNF-alpha monoclonal antibodies (see e.g., U.S. patent application Ser. No. 10/411,043), TNF receptor-IgG Fc region fusion protein (e.g., Enbrel™), anti-HER2 monoclonal antibodies (e.g., Herceptin™), monoclonal antibodies to protein F of respiratory syncytial virus (e.g., Synagis™), monoclonal antibodies to TNF-α (e.g., Remicade™), monoclonal antibodies to glycoproteins, such as IIb/IIIa (e.g., Reopro™), monoclonal antibodies to CD20 (e.g., Rituxan™), CD4 and alpha-CD3, monoclonal antibodies to PSGL-1 and CEA. Any modified (e.g., mutated) version of any of the above listed polypeptides is also within the scope of the invention.

Polypeptides Expressed in Insect Cells

In one embodiment, the polypeptide is expressed in insect cells. Insect cells suitable for use in the present invention are from any order of the class Insecta which can be hosts to recombinant viruses (e.g. baculovirus) or wild-type viruses, and which can grow and produce recombinant peptide products upon infection with the virus in a medium composition of the invention. In an exemplary embodiment, the cells are from the Diptera or Lepidoptera orders. Preferred are insect cell lines that can be used to produce polypeptides having a substantially uniform, insect-specific glycosylation pattern. In one embodiment, the polypeptide is expressed by a stably transfected cell.

About 300 insect species have been reported to have nuclear polyhedrosis virus (NPV) diseases, the majority (243) of which were isolated from Lepidoptera (see e.g., Weiss et al., Cell Culture Methods for Large-Scale Propagation of Baculoviruses, In Granados et al. (eds.), *The Biology of Baculoviruses*: Vol. II Practical Application for Insect Control, pp. 63-87 at p. 64 (1986)). Insect cell lines derived from the following insects are exemplary: *Carpocapsa pomonella* (preferably cell line CP-128); *Trichoplusia ni* (preferably cell line TN-368); *Autographa californica; Spodoptera frugiperda* (preferably cell line Sf9); *Lymantria dispar; Mamestra brassicae; Aedes albopictus; Orgyia pseudotsugata; Neodiprion sertifer; Aedes aegypti; Antheraea eucalypti; Gnorimoschema opercullela; Galleria mellonella; Spodoptera littoralis; Drosophila melanogaster, Heliothis zea; Spodoptera exigua; Rachiplusia ou; Plodia interpunctella; Amsacta moorei; Agrotis c-nitrum, Adoxophyes orana, Agrotis segetum, Bombyx mori, Hyponomeuta malinellus, Colias eurytheme, Anticarsia gemmetalis, Apanteles melanoscelus, Arctia caja*, and *Lymantria dispar.*

In an exemplary embodiment, the insect cells are from *Spodoptera frugiperda*, and in another exemplary embodiment, the cell line is Sf9 (ATCC CRL 1711). Sf9, Sf21, and High-Five insect cells are commonly used for baculovirus expression. Sf9 and Sf21 are ovarian cell lines from *Spodoptera frugiperda*. High-Five cells are egg cells from *Trichoplusia ni*. Sf9, Sf21 and High-Five cell lines may be grown at room temperature (e.g. 25 to 27° C.), and do not require $CO_2$ incubators. Their doubling time is between about 18 and 24 hours. The insect cell lines cultured to produce the peptides and glycopeptides of the invention are preferably those suitable for the reproduction of numerous insect-pathogenic viruses such as picornaviruses, parvoviruses, entomopox viruses, baculoviruses and rhabdoviruses. In an exemplary embodiment, nucleopolyhedrosis viruses (NPV) and granulosis viruses (GV) from the group of baculoviruses are preferred.

Baculoviruses are characterized by rod-shaped virus particles which are generally occluded in occlusion bodies (also called polyhedra). The family Baculoviridae can be divided in two subfamilies: the Eubaculovirinae comprising two genera of occluded viruses; nuclear polyhedrosis virus (NPV) and granulosis virus (GV), and the subfamily Nudobaculovirinae comprising the nonoccluded viruses.

Methods of preparing and using virus expression systems are generally known in the art. For example, with respect to baculovirus systems, representative references include U.S. Pat. No. 5,194,376, U.S. Pat. No. 5,147,788, U.S. Pat. No. 4,879,236 and Bedard C. et al (1994) *Cytotechnology* 15:129-138; Hink W T et al., (1991) *Biotechnology Progress* 7:9-14; Licari P. et al., (1992) *Biotechnology and Bioengineering* 39:614-618, each of which is incorporated herein by reference in its entirety. The incorporation of a desired nucleic acid into a baculovirus expression vector may be accomplished using techniques that are well known in the art. For example, such techniques are described in, Sambrook et al. (Third Edition, 2001, Molecular Cloning: A Laboratory Manual, Cold Spring Harbor Laboratory, New York), and in Ausubel et al. (1997), Current Protocols in Molecular Biology, John Wiley & Sons, New York).

In one embodiment, the polypeptide expressed in any suitable expression system, is isolated from cell culture before the polypeptide is modified with a modifying group. In one example, the polypeptide is first removed from the cell culture medium, cellular debris and other particles and is then further purified to remove contaminants, such as viral particles and unwanted proteins, using a variety of filtration and chromatographic purification devices. Polypeptide purification techniques are known. See, e.g., *Protein Purification Methods, A Practical Approach*, Ed. Harris E L V, Angal S, IRL Press Oxford, England (1989), *Protein Purification*, Ed. Janson J C, Ryden L, VCH-Verlag, Weinheim, Germany (1989), *Process Scale Bioseparations for the Biopharmaceutical Industry*, Ed. Shukla A A, Etzel M R, Gadam S, CRC Press Taylor & Francis Group (2007), and *Protein Purification, Principles, High Resolution Methods and Applications* ($2^{nd}$ Edition 1998), Ed. Janson J-C and Ryden L. Exemplary methods for the isolation of polypeptides expressed in insect cells are also disclosed in WO 06/105426 to Kang et al.

Modifying Group

The modifying group of the invention can be any chemical moiety. Exemplary modifying groups are discussed below.

Polymeric Modifying Groups

In one embodiment, the modifying group is a linear or branched polymeric modifying group (polymer). A polymeric modifying group includes at least one polymeric moiety, wherein each polymeric moiety is independently selected. In another embodiment, the polymeric modifying group is water-soluble. A water-soluble polymeric modifying group includes at least one polar group. Exemplary polar groups, include polyether groups, hydroxyl groups and carboxylic acid groups.

Many water-soluble polymers are known to those of skill in the art and are useful in practicing the present invention. The term water-soluble polymer encompasses species such as saccharides (e.g., dextran, amylose, hyaluronic acid, poly (sialic acid), heparans, heparins, etc.); poly(amino acids), e.g., poly(aspartic acid) and poly(glutamic acid); nucleic acids; synthetic polymers (e.g., poly(acrylic acid), poly(alkylene oxides), peptides, proteins, and the like. In a preferred embodiment, the polymer is a poly(alkylene oxide), such as a poly(ethylene glycol) or a polypropylene glycol.

In one example, the water-soluble polymer is polyethylene glycol (PEG) or a PEG analog, e.g., methoxy-poly(ethylene glycol) (m-PEG). In another example, the water-soluble polymer is polypropylene glycol (PPG), e.g., methoxy-polypropylene glycol (m-PPG). PEG is frequently used to modify the properties of polypeptides, such as therapeutic proteins. For example, the in vivo half-life of therapeutic glycopeptides can be enhanced with PEG moieties. Chemical modification of polypeptides with PEG (PEGylation) increases their molecular size and typically decreases surface- and functional group-accessibility, each of which are dependent on the number and size of the PEG moieties attached to the polypeptide. Frequently, this modification results in an improvement of plasma half-live and in proteolytic-stability, as well as a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). For example, PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)). Thus, in another embodiment, the in vivo half-life of a polypeptide derivatized with a PEG moiety by a method of the invention is increased relative to the in vivo half-life of the non-derivatized parent polypeptide.

The poly(ethylene glycol) or poly(propylene glycol) is not restricted to any particular form or molecular weight range. The size of these modifying groups may, for example, depend on the nature and size of the polypeptide to which they are attached and the properties desired for the modified polypeptide. For unbranched poly(ethylene glycol) or poly(propylene glycol) molecules the molecular weight is preferably between about 0.5 kDa and about 500 kDa. Branched polymers may be larger than 500 kDa. In one embodiment, branched poly (ethylene glycol) or poly(propylene glycol) have a molecular weight from about 0.5 kDa to about 1000 kDa.

In an exemplary embodiment, the PEG or PPG molecule of use in the invention (branched or unbranched) has a molecular weight selected from about 0.5 kDa, 1 kDa, about 2 kDa, about 5 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 105 kDa, about 110 kDa, about 115 kDa, about 120 kDa, about 125 kDa, about 130 kDa, about 135 kDa, about 140 kDa, about 145 kDa, about 150 kDa, about 155 kDa, about 160 kDa, about 165 kDa, about 170 kDa, about 175 kDa, about 180 kDa, about 185 kDa, about 190 kDa, about 195 kDa and about 400 kDa.

In one embodiment, the polypeptide is EPO. In another embodiment, the EPO peptide has at least two, and preferably three poly(ethylene glycol) moieties covalently linked thereto. In one example according to this embodiment, each PEG molecule linked to the EPO peptide has a molecular weight from about 2 kDa to about 80 kDa, preferably from about 5 kDa to about 60 kDa and more preferably from about 10 kDa to about 40 kDa.

Exemplary water-soluble polymers are those in which a substantial proportion of the polymer molecules in a sample of the polymer are of approximately the same molecular weight; such polymers are "homodisperse."

The following discussion of polymers including PEG moieties is for clarity of illustration. Those of skill will appreciate that the focus in the sections that follow and the various motifs set forth using PEG as an exemplary polymer are equally applicable to species in which a polymer other than PEG (e.g., another poly(alkylene oxide)) is utilized.

Exemplary poly(ethylene glycol) molecules of use in the invention include, but are not limited to, those having the formula:

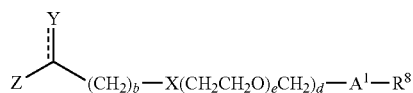

in which $R^8$ is H, OH, NH$_2$, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, H$_2$N—(CH$_2$)$_q$—, HS—(CH$_2$)$_q$, or —(CH$_2$)$_q$C(Y)Z$^1$. The index "e" represents an integer from 1 to 2500. The indices b, d, and q independently represent integers from 0 to 20. The symbols Z and Z$^1$ independently represent OH, NH$_2$, leaving groups, e.g., imidazole, p-nitrophenyl, HOBT, tetrazole, halide, S—R$^9$, the alcohol portion of activated esters; —(CH$_2$)$_p$C(Y$^1$)V, or —(CH$_2$)$_p$U(CH$_2$)$_s$C(Y$^1$)$_v$. The symbol Y represents H(2), =O, =S, =N—R$^{10}$. The symbols X, Y, Y$^1$, A$^1$, and U independently represent the moieties O, S, N—R$^{11}$. The symbol V represents OH, NH$_2$, halogen, S—R$^{12}$, the alcohol component of activated esters, the amine component of activated amides, sugar-nucleotides, and proteins. The indices p, q, s and v are members independently selected from the integers from 0 to 20. The symbols R$^9$, R$^{10}$, R$^{11}$ and R$^{12}$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

The poly(ethylene glycol) useful in forming the conjugate of the invention is either linear or branched. Branched poly (ethylene glycol) molecules suitable for use in the invention include, but are not limited to those described by the following formula:

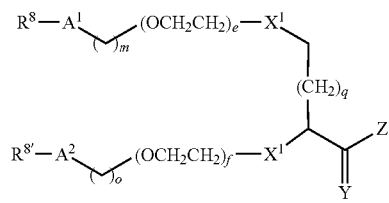

in which R$^8$ and R$^{8'}$ are members independently selected from the groups defined for R$^8$, above. A$^1$ and A$^2$ are members independently selected from the groups defined for A$^1$, above. The indices e, f, o, and q are as described above. Z and Y are as described above. X$^1$ and X$^{1'}$ are members independently selected from S, SC(O)NH, HNC(O)S, SC(O)O, O, NH, NHC(O), (O)CNH and NHC(O)O, OC(O)NH.

In other exemplary embodiments, the branched PEG is based upon a cysteine, serine or di-lysine core. In another exemplary embodiments, the poly(ethylene glycol) molecule is selected from the following structures:

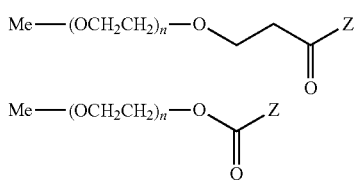

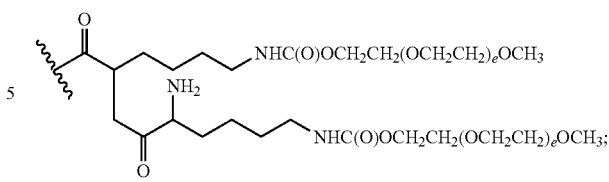

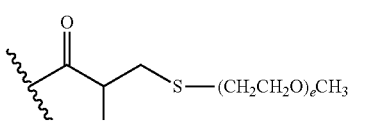

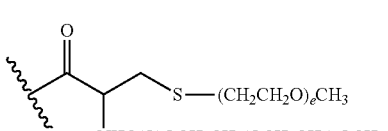

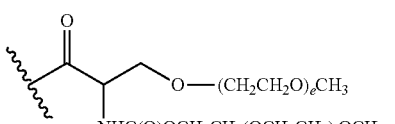

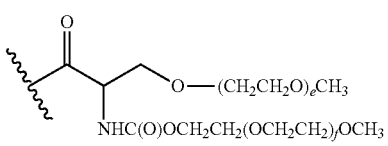

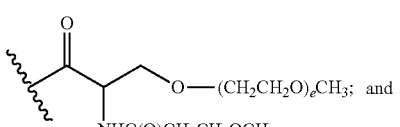

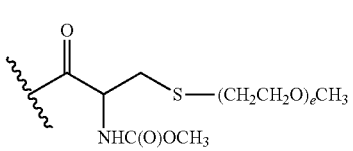

In a further embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is less than or equal to 40,000 daltons.

Representative polymeric modifying moieties include structures that are based on side chain-containing amino acids, e.g., serine, cysteine, lysine, and small peptides, e.g., lys-lys. Exemplary structures include:

Those of skill will appreciate that the free amine in the di-lysine structures can also be pegylated through an amide or urethane bond with a PEG moiety.

In yet another embodiment, the polymeric modifying moiety is a branched PEG moiety that is based upon a tri-lysine peptide. The tri-lysine can be mono-, di-, tri-, or tetra-PEG-ylated. Exemplary species according to this embodiment have the formulae:

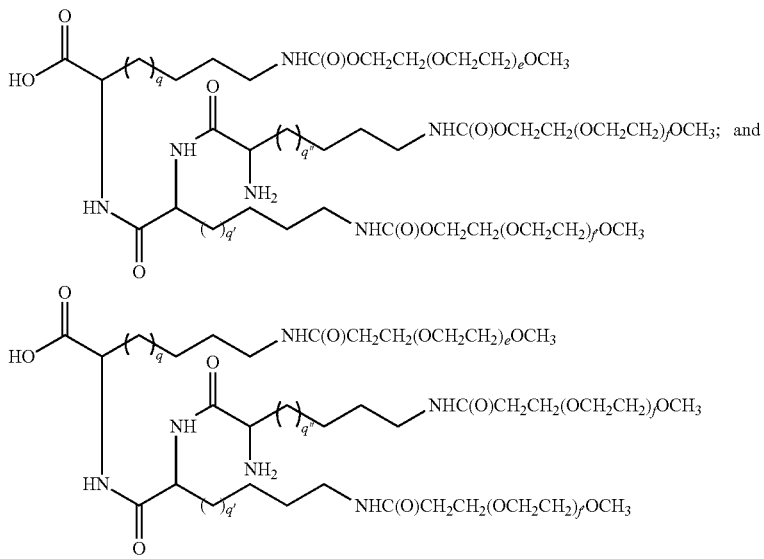

in which the indices e, f and f' are independently selected integers from 1 to 2500; and the indices q, q' and q" are independently selected integers from 1 to 20.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

An exemplary branched modifying group including one or more polymeric moieties (e.g., PEG moieties) includes the formula:

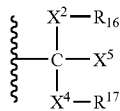

In one embodiment, the branched polymer species according to this formula are essentially pure water-soluble polymers. C is carbon. $X^5$ is a non-reactive group. In one embodiment, $X^5$ is selected from H, OH and $C_1$-$C_6$ alkyl (e.g., $CH_3$, $—CH_2CH_3$) optionally substituted with OH. $R^{16}$ and $R^{17}$ are independently selected from non-reactive groups (e.g., H, unsubstituted alkyl, unsubstituted heteroalkyl) and polymeric arms (e.g., PEG). $X^2$ and $X^4$ are linkage fragments that are preferably essentially non-reactive under physiological conditions. $X^2$ and $X^4$ are independently selected. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join the polymeric arms $R^{16}$ and $R^{17}$ to C. Exemplary linkage fragments including $X^2$ and $X^4$ are independently selected and include S, SC(O)NH, HNC(O)S, SC(O)O, O, NH, NHC(O), (O)CNH and NHC(O)O, and OC(O)NH, $CH_2$S, $CH_2$O, $CH_2CH_2$O, $CH_2CH_2$S, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, the modifying group is derived from a natural or unnatural amino acid, amino acid analog or amino acid mimetic, or a small peptide formed from one or more such species. For example, certain branched polymers found in the polypeptide conjugates of the invention have the formula, wherein La is a linker moiety that links the modifying group to the remainder of the polypeptide conjugate.

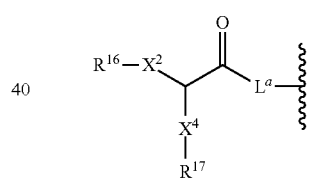

In an exemplary embodiment, $L^a$ is a linking moiety having the structure:

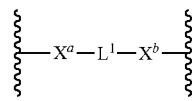

in which $X^a$ and $X^b$ are independently selected linkage fragments and $L^1$ is selected from a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (e.g., Lys-Lys-Lys) in which the alpha-amine moiety(ies) and/or side chain heteroatom(s) are modified with a polymeric modifying moiety.

In other exemplary embodiments, the polypeptide conjugate includes a moiety selected from the group:

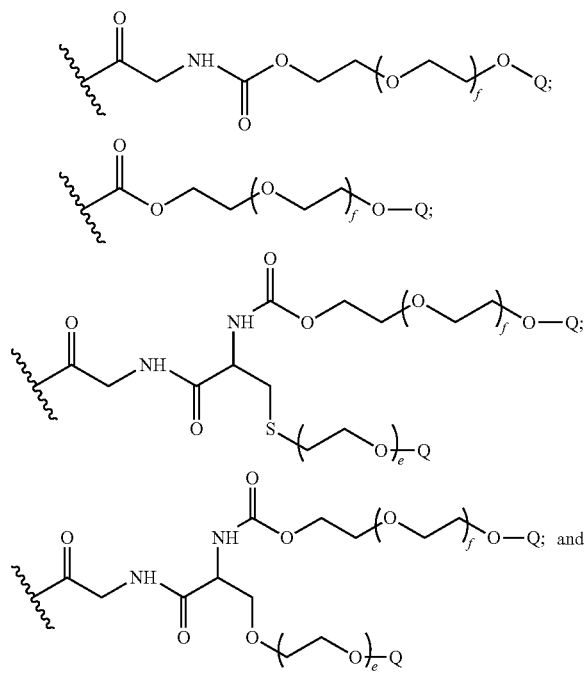

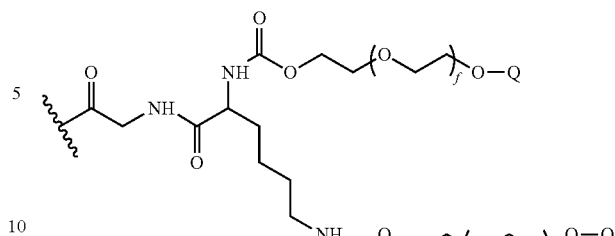

In each of the formulae above, the indices e and f are independently selected from the integers from 1 to 2500. In further exemplary embodiments, e and f are selected to provide a PEG moiety that is about 1 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa and 80 kDa. The symbol Q represents substituted or unsubstituted alkyl (e.g., $C_1$-$C_6$ alkyl, e.g., methyl), substituted or unsubstituted heteroalkyl or H.

Other branched polymers have structures based on di-lysine (Lys-Lys) peptides, e.g.:

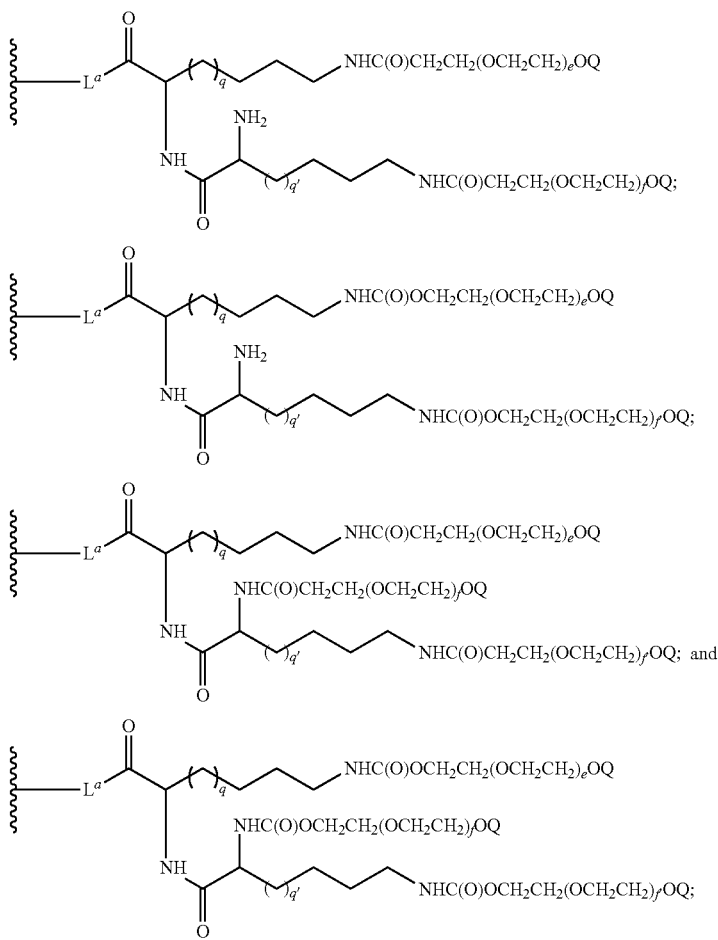

and tri-lysine peptides (Lys-Lys-Lys), e.g.:

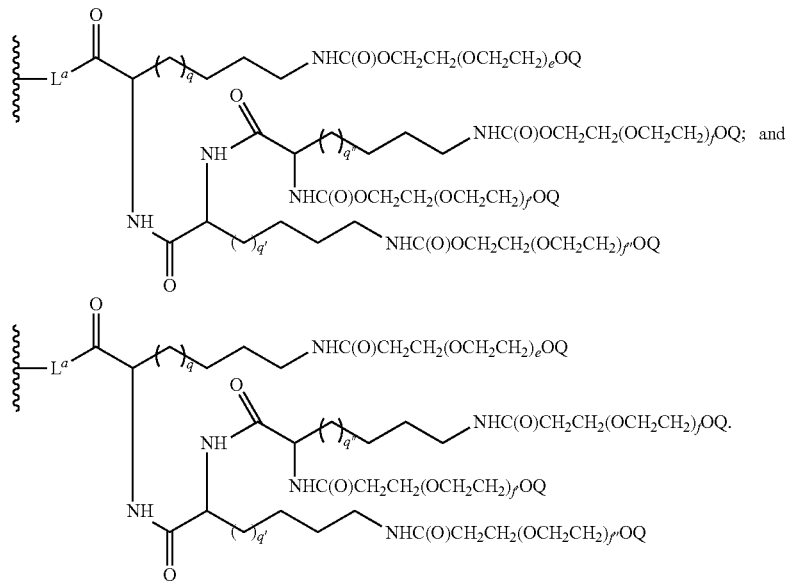

In each of the figures above, the indices e, f, f' and f" represent integers independently selected from 1 to 2500. The indices q, q' and q" represent integers independently selected from 1 to 20.

In another exemplary embodiment, the conjugates of the invention include a formula which is a member selected from:

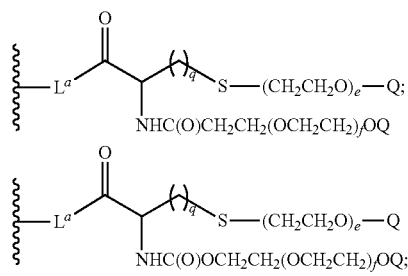

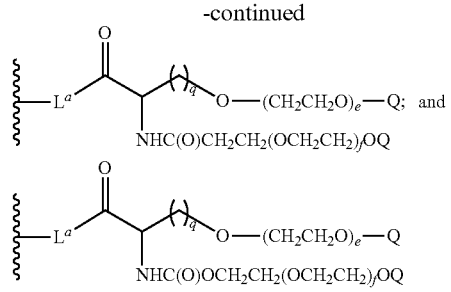

wherein Q is a member selected from H and substituted or unsubstituted $C_1$-$C_6$ alkyl. The indices e and f are integers independently selected from 1 to 2500, and the index q is an integer selected from 0 to 20.

In another exemplary embodiment, the conjugates of the invention include a formula which is a member selected from:

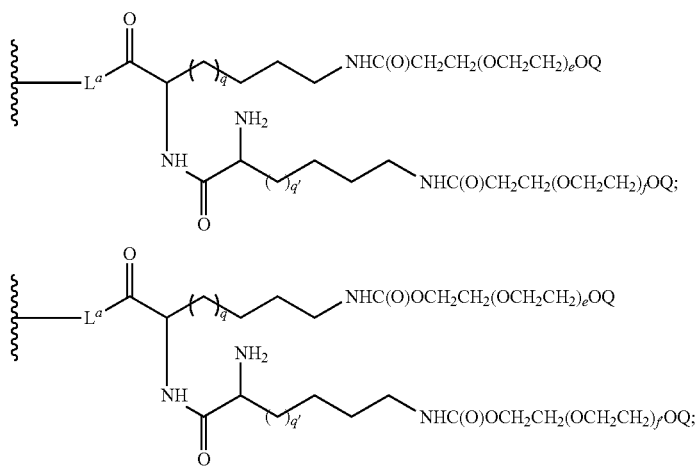

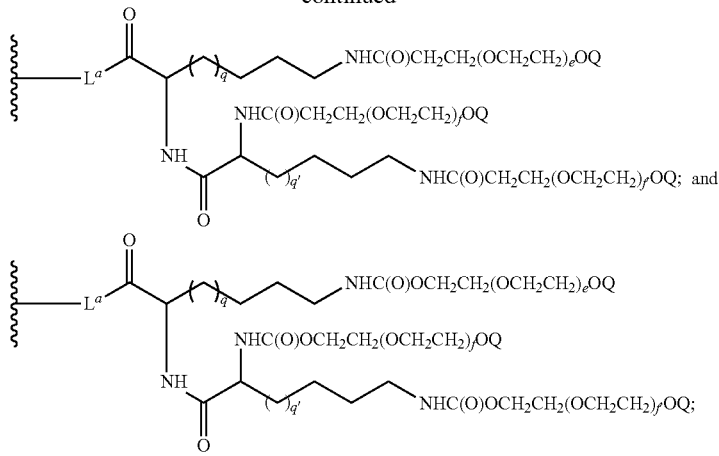

wherein Q is a member selected from H and substituted or unsubstituted $C_1$-$C_6$ alkyl, preferably Me. The indices e, f and f' are integers independently selected from 1 to 2500, and q and q' are integers independently selected from 1 to 20.

In another exemplary embodiment, the conjugate of the invention includes a structure according to the following formula:

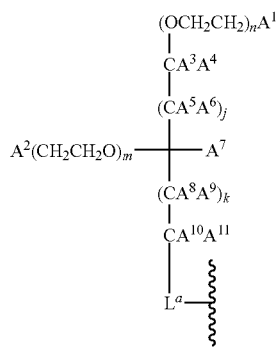

wherein the indices m and n are integers independently selected from 0 to 5000. The indices j and k are integers independently selected from 0 to 20. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted aryl, substituted or unsubstituted cycloalkyl, substituted or unsubstituted heterocycloalkyl, substituted or unsubstituted heteroaryl, —$NA^{12}A^{13}$, —$OA^{12}$ and —$SiA^{12}A^{13}$ $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In one embodiment according to the formula above, the branched polymer has a structure according to the following formula:

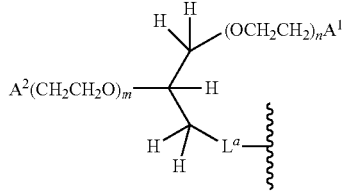

In an exemplary embodiment, $A^1$ and $A^2$ are members independently selected from —$OCH_3$ and OH.

In another exemplary embodiment, the linker $L^a$ is a member selected from aminoglycine derivatives. Exemplary polymeric modifying groups according to this embodiment have a structure according to the following formulae:

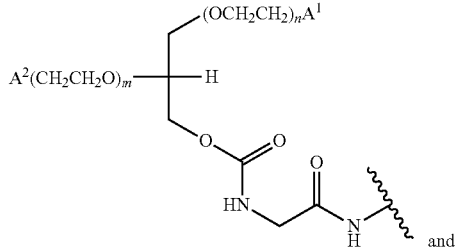

In one example, $A^1$ and $A^2$ are members independently selected from $OCH_3$ and OH. Exemplary polymeric modifying groups according to this example include:

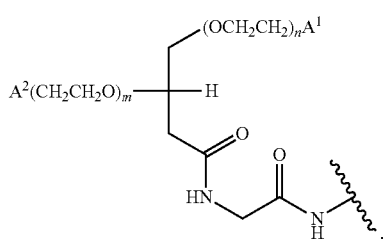

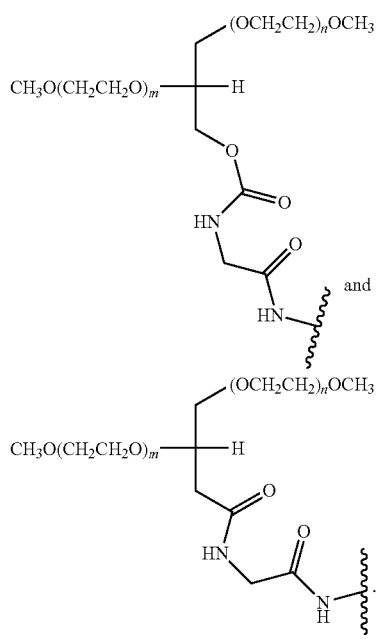

In each of the above embodiment, wherein the modifying group includes a stereocenter, for example those including an amino acid linker or a glycerol-based linker, the stereocenter can be either racemic or defined. In one embodiment, in which such stereocenter is defined, it has (S) configuration. In another embodiment, the stereocenter has (R) configuration.

Those of skill in the art will appreciate that one or more of the m-PEG arms of the branched polymer can be replaced by a PEG moiety with a different terminus, e.g., OH, COOH, $NH_2$, $C_2$-$C_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

The linear and branched PEG conjugates set forth herein may be prepared using art-recognized methods. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al, *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S. Pat. No. 5,672,662, U.S. Pat. No. 6,376,604, WO 99/45964, WO 96/21469, U.S. Pat. No. 5,932,462, U.S. Pat. No. 5,446,090, WO 99/34833, WO 99/14259, U.S. Pat. No. 6,348,558.

The art-recognized methods of polymer activation set forth above are of use in the context of the present invention in the formation of the branched polymers set forth herein.

Glycosyl Linking Group

In one embodiment, the modifying group is covalently linked to the polypeptide via a glycosyl linking group. The saccharide component of the modified sugar, when interposed between the polypeptide and a modifying group, becomes a "glycosyl linking group." In an exemplary embodiment, the glycosyl linking group is formed from a mono- or oligosaccharide that, after modification with a modifying group, is a substrate for an appropriate enzyme, such as a glycosyltransferase. In another exemplary embodiment, the glycosyl linking group is formed from a glycosyl-mimetic moiety. The polypeptide conjugates of the invention can include glycosyl linking groups that are mono- or multivalent (e.g., antennary structures). Thus, conjugates of the invention include both species in which a modifying group is attached to a polypeptide via a monovalent glycosyl linking group. Also included within the invention are conjugates in which more than one modifying group is attached to a polypeptide via a multivalent linking group. Exemplary linking groups are disclosed in PCT/US07/74139 filed Jul. 23, 2007, the disclosure of which is incorporated by reference herein in its entirety.

In an exemplary embodiment, the invention provides a method for the isolation of a glycopeptide that is conjugated to a polymeric modifying moiety through an intact glycosyl linking group having a formula that is selected from:

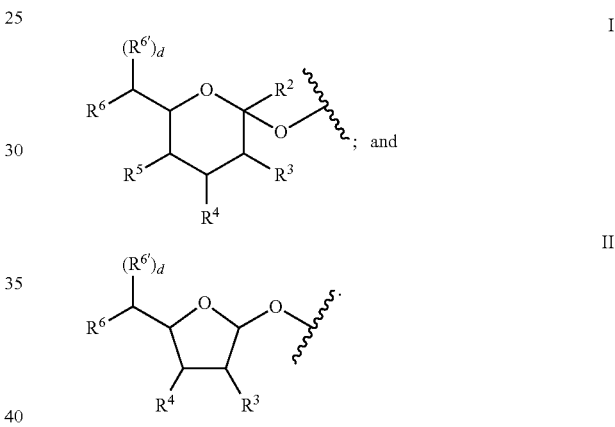

In Formulae I, $R^2$ is H, $CH_2OR^7$, $COOR^1$ or $OR^7$, in which $R^7$ represents H, substituted or unsubstituted alkyl or substituted or unsubstituted heteroalkyl. When $COOR^7$ is a carboxylic acid or carboxylate, both forms are represented by the designation of the single structure $COO^-$ or COOH. In Formulae I and II, the symbols $R^3$, $R^4$, $R^5$, $R^6$ and $R^{6'}$ independently represent H, substituted or unsubstituted alkyl, $OR^8$, NHC(O) $R^9$. The index d is 0 or 1. $R^5$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes the polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, this side chain is functionalized with the polymeric modifying moiety. In another exemplary embodiment, $R^6$ and $R^{6'}$, together with the carbon to which they are attached are components of the side chain of sialic acid and the polymeric modifying moiety is a component of $R^5$.

In a further exemplary embodiment, the polymeric modifying moiety is bound to the sugar core, generally through a heteroatom, e.g, nitrogen, on the core through a linker, L, as shown below:

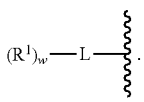

R[1] is the polymeric moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety.

An exemplary compound according to the invention has a structure according to Formulae I or II, in which at least one of $R^2$, $R^3$, $R^4$, $R^5$, $R^6$ or $R^{6'}$ has the formula:

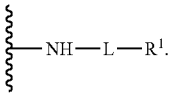

In another example according to this embodiment at least one of $R^2$, $R^3$, $R^4$, $R^5$, $R^6$ or $R^{6'}$ has the formula:

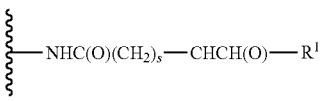

in which s is an integer from 0 to 20 and R[1] is a linear polymeric modifying moiety.

In an exemplary embodiment, the polymeric modifying moiety-linker construct is a branched structure that includes two or more polymeric chains attached to central moiety. In this embodiment, the construct has the formula:

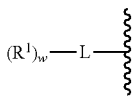

in which R[1] and L are as discussed above and w' is an integer from 2 to 6, preferably from 2 to 4 and more preferably from 2 to 3.

When L is a bond it is formed between a reactive functional group on a precursor of R[1] and a reactive functional group of complementary reactivity on the saccharyl core. When L is a non-zero order linker, a precursor of L can be in place on the glycosyl moiety prior to reaction with the R[1] precursor. Alternatively, the precursors of R[1] and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, R[5] includes the polymeric modifying moiety. In another exemplary embodiment, R[5] includes both the polymeric modifying moiety and a linker, L, joining the modifying moiety to the remainder of the molecule. As discussed above, L can be a linear or branched structure. Similarly, the polymeric modifying can be branched or linear.

In one embodiment, the present invention provides methods for the isolation of an erythropoietin peptide conjugate comprising the moiety:

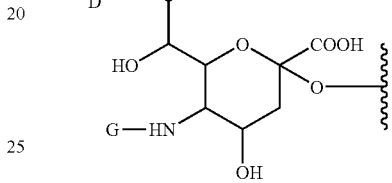

wherein D is a member selected from —OH and R[1]-L-HN—; G is a member selected from H and R[1]-L- and —C(O)(C[1]-C[6])alkyl; R[1] is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is R[1]-L-, and when G is —C(O)(C[1]-C[6])alkyl, D is R[1]-L-NH—.

In another exemplary embodiment, the invention provides a conjugate formed between a modified sugar of the invention and a substrate EPO peptide. In this embodiment, the sugar moiety of the modified sugar becomes a glycosyl linking group interposed between the peptide substrate and the modifying group. An exemplary glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. Exemplary modifying group-intact glycosyl linking group cassettes according to this motif are based on a sialic acid structure, such as those having the formulae:

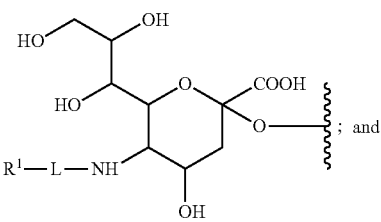

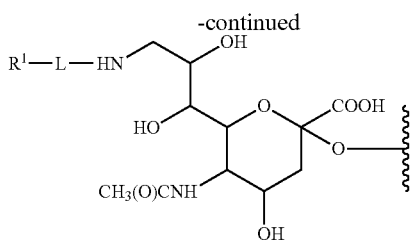

In the formulae above, R¹ and L are as described above. Further detail about the structure of exemplary R¹ groups is provided below.

In still a further exemplary embodiment, the conjugate is formed between a substrate EPO and a saccharyl moiety in which the modifying group is attached through a linker at the 6-carbon position of the saccharyl moiety. Thus, illustrative conjugates according to this embodiment have the formula:

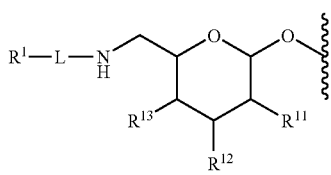

in which the radicals are as discussed above. Such saccharyl moieties include, without limitation, glucose, glucosamine, N-acetyl-glucosamine, galactose, galactosamine, N-acetyl-galactosamine, mannose, mannosamine, N-acetyl-mannosamine, and the like.

Due to the versatility of the methods available for modifying glycosyl residues on a therapeutic peptide such as EPO, the glycosyl structures on the peptide conjugates of the invention can have substantially any structure. Moreover, the glycans can be O-linked or N-linked. As exemplified in the discussion below, each of the pyranose and furanose derivatives discussed above can be a component of a glycosyl moiety of a peptide.

The invention provides a modified EPO peptide that includes a glycosyl group having the formula:

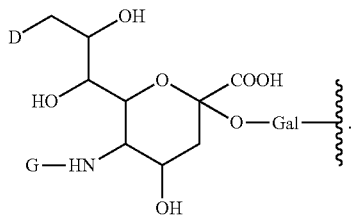

In other embodiments, the group has the formula:

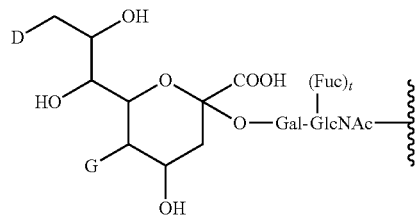

in which the index t is 0 or 1.

In a still further exemplary embodiment, the group has the formula:

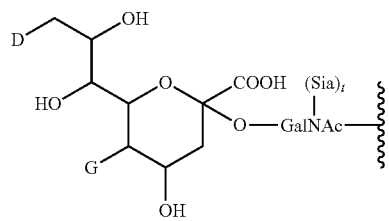

in which the index t is 0 or 1.

In yet another embodiment, the group has the formula:

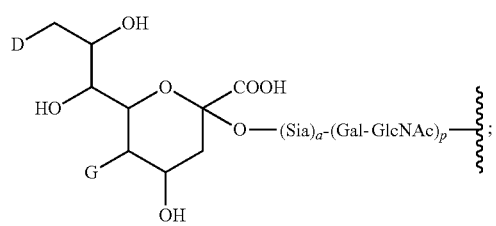

in which the index p represents and integer from 1 to 10; and a is either 0 or 1.

In an exemplary embodiment, a glycoPEGylated EPO peptide of the invention includes at least one N-linked glycosyl residue selected from the glycosyl residues set forth below:

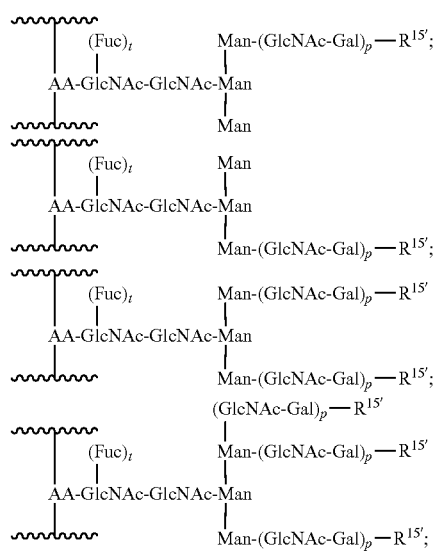

-continued

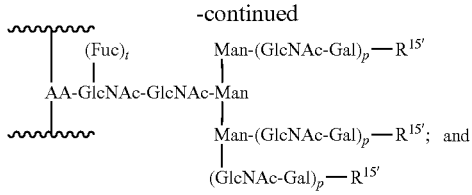

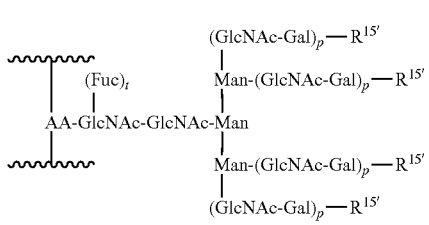

In the formulae above, the index t is 0 or 1 and the index p is an integer from 1 to 10. The symbol $R^{15'}$ represents H, OH (e.g., Gal-OH), a sialyl moiety, a polymer modified sialyl moiety (i.e., glycosyl linking group-polymeric modifying moiety (Sia-L-$R^1$)) or a sialyl moiety to which is bound a polymer modified sialyl moiety (e.g., Sia-Sia-L-$R^1$) ("Sia-$Sia^p$"). An exemplary EPO peptide of the invention will include at least one glycan having a $R^{15'}$. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3- to the galactose residue. In another exemplary embodiment, the sialic acid is linked α2,6- to the galactose residue.

The modified glycan is bound to one or more position selected from Asn 24, Asn 38, Asn 83 and/or Ser 126. In an exemplary embodiment, the EPO is derived from mammalian cells and the modifying group is only on the glycan at Asn 24. In one embodiment according to this motif, the glycosyl linking moiety is linked to a Sia residue through another Sia residue, e.g.:

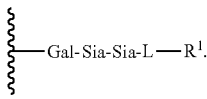

An exemplary species according to this motif is prepared by conjugating Sia-L-$R^1$ to a terminal sialic acid of the glycan at $Asn^{24}$ using an enzyme that forms Sia-Sia bonds, e.g., CST-II, ST8Sia-II, ST8Sia-III and ST8Sia-IV.

In another exemplary embodiment, the glycans have a formula that is selected from the group:

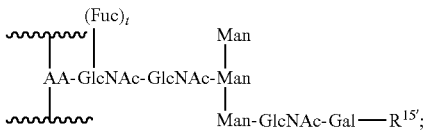

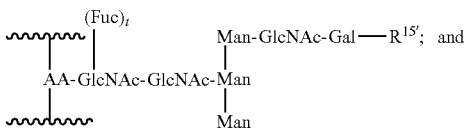

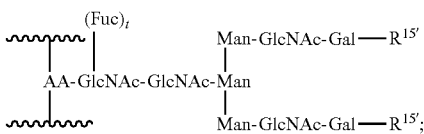

and a combination thereof.

The glycans of this group generally correspond to those found on an EPO peptide that is produced by insect cells (e.g., Sf9), followed by remodeling of the glycan and glycoPEGylation according to the methods set forth herein. For example, insect-derived EPO that is expressed with a tri-mannosyl core is subsequently contacted with a GlcNAc donor and a GlcNAc transferase and a Gal donor and a Gal transferase. Appending GlcNAc and Gal to the tri-mannosyl core is accomplished in either two steps or a single step. A modified sialic acid is added to at least one branch of the glycosyl moiety as discussed herein. Those Gal moieties that are not functionalized with the modified sialic acid are optionally "capped" by reaction with a sialic acid donor in the presence of a sialyl transferase.

In an exemplary embodiment, at least 60% of terminal Gal moieties in a population of peptides is capped with sialic acid, preferably at least 70%, more preferably, at least 80%, still more preferably at least 90% and even more preferably at least 95%, 96%, 97%, 98% or 99% are capped with sialic acid.

In each of the formulae above, $R^{15'}$ is as discussed above. Moreover, an exemplary modified EPO peptide of the invention will include at least one glycan with an $R^{15'}$ moiety having a structure according to Formulae I or II.

In another exemplary embodiment, the EPO is derived from insect cells, which are remodeled by adding GlcNAc and Gal to the mannose core. The remodeled peptide is glycopegylated using a sialic acid bearing a linear PEG moiety, affording an EPO peptide that comprises at least one moiety having the formula:

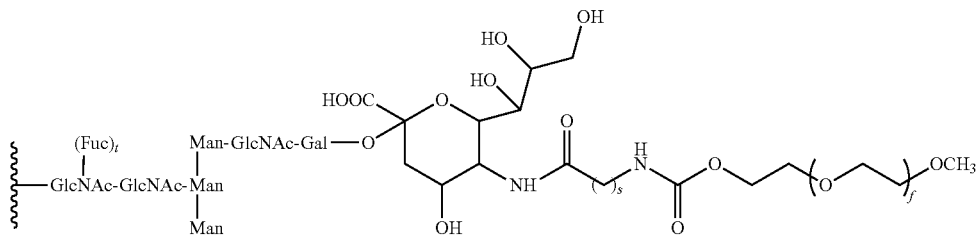

in which s represents and integer from 1 to 10; and f represents and integer from 1 to 2500.

In certain embodiments, the EPO peptide includes three such moieties, one attached at each of Asn 24, Asn 38 and Asn 83. In another embodiment, the peptide includes two such moieties attached at a combination of two of these Asn moieties. There is also provided a composition that is a mixture of these two species (i.e., $PEG_3$ and $PEG_2$). The mixture preferably includes at least 75%, preferably at least 80%, more preferably at least 85%, still more preferably 90% and even more preferably 95%, 96%, 97% or 98% of the species that includes the three modified glycosyl residues. Unmodified terminal Gal residues are optionally capped with Sia as discussed above. In an exemplary embodiment, the peptide is expressed in insect cells, remodeled and glycopegylated.

The indices e and q are as discussed above. In an exemplary embodiment, e for each of the modified glycosyl moieties is an integer that provides as PEG moiety having a molecular weight of approximately 10 kDa.

I.b) Isolation of Polypeptide Conjugates

The membrane filtration and chromatographic techniques described below are useful steps within the methods of the invention and apply to the isolation of polypeptide conjugates, in which a polypeptide is linked to at least one modifying group, such as a poly(alkylene oxide) moiety. It is to be understood that unless the order of steps is explicitly recited, the exemplary steps can be performed in any desired order.

Membrane Filtration

In one embodiment, the methods of the invention includes one or more membrane filtration steps. Membrane filtration is a separation technique widely used for clarifying, concentrating, and purifying polypeptides.

Ultrafiltration/Diafiltration

Ultrafiltration Using a Membrane with a Small MWCO

In one exemplary embodiment, the polypeptide purification process of the present invention includes at least one diafiltration/ultrafiltration step, e.g., as the final process step to generate a composition suitable for storage. In one example, diafiltration/ultrafiltration is performed to condition a mixture for a chromatographic process step. For example, the eluate from a hydrophobic interaction chromatography step is concentrated and the buffer is exchanged to prepare the sample for the next purification step (e.g., cation exchange chromatography).

In an exemplary embodiment, the diafiltration step is employed to concentrate the sample. In another exemplary embodiment the diafiltration step is employed to alter the buffer. In yet another exemplary embodiment, the new buffer is suitable for storage of the purified polypeptide conjugate. The diafiltration/ultrafiltration membrane can have any molecular weight cutoff (MWCO) specification.

In an exemplary embodiment, the feed is passed through an ultrafiltration membrane with a MWCO suitable to concentrate the purified polypeptide conjugate. The selected MWCO will depend on the combined size of the polypeptide and the modifying group, such as the size of a poly(alkylene oxide) moiety covalently linked to the polypeptide. To concentrate a sample, the membrane is chosen to have a MWCO that is substantially lower than the molecular weight of the purified peptide conjugate. In one example, the ultrafiltration membrane is selected to have a MWCO that is 3 to 6 times lower than the molecular weight of the peptide conjugate to be retained by the membrane. If the flow rate or the processing time is of major consideration, selection of a membrane with a MWCO toward the lower end of this range (e.g. 3×) will yield higher flow rates. If recovery of peptide conjugate is the primary concern, a tighter membrane (e.g. 6×) is selected (typically with a slower flow rate).

In one exemplary embodiment, the diafiltration membrane has a MWCO of about 2 kDa to about 500 kDa. In another exemplary embodiment, the diafiltration membrane has a MWCO of about 5 kDa to about 400 kDa, about 5 kDa to about 300 kDa or about 5 kDa to about 200 kDa. In yet another exemplary embodiment, the diafiltration membrane has a MWCO of about 5 kDa to about 180 kDa, 5 kDa to about 160 kDa, 5 kDa to about 140 kDa, 5 kDa to about 130 kDa, 5 kDa to about 120 kDa, 5 kDa to about 110 kDa, or 5 kDa to 100 kDa. When the polypeptide conjugate is EPO-PEG, the diafiltration membrane has a MWCO of about 5 kDa to about 80 kDa, 5 kDa to about 60 kDa, 5 kDa to about 40 kDa or 5 kDa to about 20 kDa. In one embodiment, when the polypeptide conjugate is EPO-[PEG-10 kDa]$_3$, the diafiltration membrane has a MWCO of about 8 kDa to about 12 kDa and preferably about 10 kDa.

In another exemplary embodiment, filtration is effected using a transmembrane pressure between about 1 and about 30 psi and a filter membrane with a MWCO of between about 5 kDa to about 15 kDa, and preferably 10 kDa. The filtration step produces a retentate stream and a permeate stream. The retentate may be recycled to a reservoir for the peptide solution feed under conditions of essentially constant peptide concentration in the feed by adding a buffer solution to the retentate.

The surface area of the filtration membrane used will generally depend on the amount of peptide conjugate to be purified. The membrane may be made of a low-binding material to minimize adsorptive losses and is preferably durable, cleanable, and chemically compatible with the buffers to be used. A number of suitable membranes are commercially available. In an exemplary embodiment, the ultrafiltration/diafiltration membrane is a member selected from cellulose acetate, regenerated cellulose and polyethersulfone. Suitable membranes include those, in which the membrane polymer is chemically modified. In a preferred embodiment, the membrane is regenerated cellulose.

In one embodiment, the flow rate is adjusted to maintain a constant transmembrane pressure. Generally, filtration will proceed faster with higher pressures and higher flow rates, but higher flow rates may also result in damage to the peptide or loss of peptide due to passage through the membrane. In addition, various devices may have certain pressure limitations on their operation, and the pressure is adjusted according to the manufacturer's specification. In an exemplary embodiment, the pressure is between about 1 to about 30 psi, and in another exemplary embodiment the pressure is between about 8 psi to about 15 psi. Typically, the circulation pump is a peristaltic pump or diaphragm pump in the feed channel and the pressure is controlled by adjusting the retentate valve.

Subsequent to a filtration step, the retentate is collected. Water or an aqueous buffer (e.g. diafiltration buffer) may be used to wash the membrane filter and recover any peptide retained by the membrane. The wash liquid may be combined with the original retentate containing the concentrated peptide. The retentate is optionally dialyzed against another buffer, such as TRIS or HEPES.

The purified product is stored at a low temperature. In an exemplary embodiment the product is stored at about −20° C. at a polypeptide concentration of about 1 mg to about 10 mg of peptide conjugate per mL storage buffer. Before storage the product solution maybe sterile filtered, e.g., using a membrane filter having a pore size of about 2 μM (e.g., cellulose acetate filter).

Chromatographic Isolation of Polypeptide Conjugates

A variety of recognized chromatographic techniques, such as size exclusion chromatography (gel filtration), ion exchange chromatography, hydrophobic interaction chromatography (HIC), affinity chromatography, mixed-mode chromatography, hydroxyapatite and fluoroapatite chromatography are used for the isolation of polypeptides and proteins. These technologies can also be used to isolate polypeptide conjugates. In an exemplary embodiment, methods of the invention employ a combination of several chromatographic techniques. The order in which these steps are performed is dependent on the nature of the polypeptide conjugate being purified and the nature of the contaminants to be removed.

Suitable techniques for the practice of the invention separate the polypeptide conjugate of interest from a variety of contaminants on the basis of charge, degree of hydrophobicity, and/or size. Different chromatographic resins and membranes are available for each of these techniques, allowing accurate tailoring of the purification scheme.

In one chromatographic technique, the components in a mixture interact differently with the column material and move at different rates along the column length, achieving a physical separation that increases as the components pass through the column. In another chromatographic technique, components of the mixture, including the peptide conjugate of interest, adhere selectively to the separation medium, while other components are found in the flow-through. The initially retained components are then eluted differentially by varying the composition of the solvent or buffer system. In another approach, the desired components are found in the flow-through while impurities are retained on the column and thus removed from the mixture.

Ion Exchange Chromatography

In one embodiment, the methods of the invention employ at least one ion exchange chromatography step. Anion and cation exchange chromatography are known in the art. Ion exchange chromatography separates compounds based on their net charge. Ionic molecules are classified as either anions (having a negative charge) or cations (having a positive charge). Some molecules (e.g., proteins) may have both anionic and cationic groups. A positively charged support (anion exchanger) will bind a compound with an overall negative charge. Conversely, a negatively charged support (cation exchanger) will bind a compound with an overall positive charge. Ion exchange matrices can be further categorized as either strong or weak exchangers. Strong ion exchange matrices are charged (ionized) across a wide range of pH levels. Weak ion exchange matrices are ionized within a narrow pH range. The ionic groups of exchange columns are covalently bound to the gel matrix and are compensated by small concentrations of counter ions, which are present in the buffer. The most common ion exchange chemistries include: quaternary ammonium residues (Q) for strong anion exchange, diethylaminoethyl residues (DEAE) for weak anion exchange, sulfopropyl (SP) resins and sulfonic acid (S) resins for strong cation exchange and carboxymethyl residues (CM) for weak cation exchange.

When adding a sample to the column, an exchange with the weakly bound counter ions takes place. The size of the sample volume in ion exchange chromatography is of secondary importance as long as the initial solvent is of low eluting strength, to not allow the sample components to proceed through the column. Under such conditions, the sample components are preferably collected at the top of the column. When the gradient is begun with the addition of a stronger eluting mobile phase, the sample components begin their separation. If poor separation is observed, it might be improved by a change in the gradient slope. If the polypeptide conjugate does not bind to the column under the selected conditions, the composition and/or the pH of the starting buffer should be changed. The buffer system can further be optimized by choosing different buffer salts since each buffer composition solvates the ion exchanger and the sample components uniquely.

In one example, any conventional buffer system with a salt concentration of about mM up to about 50 mM can be used for ion exchange chromatography. However, positively charged buffering ions are used for anion exchangers and negatively charged ones are used for cation exchangers. Phosphate buffers are generally used on both exchanger types. Typically, the highest salt concentration that permits binding of the peptide of interest is used as the starting condition. In one example, all buffers are prepared from MilliQ-water and filtered (0.45 or 0.22 μm filter).

Anion Exchange Chromatography

In an exemplary embodiment a sample containing the peptide conjugate of interest is loaded onto an anion exchanger in a loading buffer comprising a salt concentration below the concentration at which the peptide would elute from the column. The pH of the buffer is selected so that the purified peptide is retained on the anion exchange medium. Changing the pH of the buffer alters the charge of the peptide, and lowering the pH value shortens the retention time with anion exchangers. The isoelectric point (pI) of a protein is the pH at which the charge of a protein is zero. Typically, with anion exchangers the pH value of the buffer is kept 1.5 to 2 times higher than the pI value of the peptide of interest. Alternatively, the anion exchange conditions are selected to preferentially bind impurities, while the purified peptide is found in the flow-through.

The column may be washed with several column volumes (CV) of buffer to remove unbound substances and/or those substances that bind weakly to the resin. Fractions are then eluted from the column using, for example, a saline gradient according to conventional methods. The salt in the solution competes with the protein in binding to the column and the protein is released. Components with weak ionic interactions elute at a lower salt concentration than components with a strong ionic interaction. Sample fractions are collected from the column. Fractions containing high levels of the desired peptide and low levels of impurities are pooled or processed separately.

In one example, anion exchange used in the process of the current invention is employed to isolate the polypeptide conjugate from contaminants such as particulates, chemicals and proteins/peptides (e.g., enzymes used in a glycoPEGylation reaction).

Anion exchange media are known to those of skill in the art. Exemplary anion exchange media are described, e.g., in *Protein Purification Methods, A Practical Approach*, Ed. Harris E L V, Angal S, IRL Press Oxford, England (1989); *Protein Purification*, Ed. Janson J C, Ryden L, VCH-Verlag, Weinheim, Germany (1989); *Process Scale Bioseparations for the Biopharmaceutical Industry*, Ed. Shukla A A, Etzel M R, Gadam S, CRC Press Taylor & Francis Group (2007), pages 188-196; *Protein Purification Handbook*, GE Healthcare 2007 (18-1132-29) and *Protein Purification, Principles, High Resolution Methods and Applications* ($2^{nd}$ Edition 1998), Ed. Janson J-C and Ryden L, the disclosures of which are incorporated herein by reference in their entirety. An exemplary anion exchanger of the invention is selected from quaternary ammonium filters and DEAE resins. In one embodiment, the anion exchanger is a quaternary ammonium resin (e.g. Mustang Q ion exchange membrane, Pall Corporation). In one example, the anion exchanger is Sartobind Q. Other useful resins include QXL, Capto and BigBeads resins.

Exemplary anion exchange media are summarized below:
GE Healthcare:
Q-Sepharose FF
Q-Sepharose BB
Q-Sepharose XL
Q-Sepharose HP
Mini Q
Mono Q
Mono P
DEAE Sepharose FF
Source 15Q
Source 30Q
Capto Q
ANX Sepharose 4 FF (high sub)
Streamline DEAE
Streamline QXL
Applied Biosystems:
Poros HQ 10 and 20 um self pack
Poros HQ 20 and 50 um bulk media
Poros PI 20 and 50 um
Poros D 50 um
Tosohaas:
Toyopearl DEAE 650S, M and C
Super Q 650
QAE 550C
Pall Corporation:
DEAE Hyper D
Q Ceramic Hyper D
Mustang Q membrane absorber
Merck KG2A:
Fractogel DMAE
FractoPrep DEAE
Fractoprep TMAE
Fractogel EMD DEAE
Fractogel EMD TMAE
Sartorious:
Sartobind Q membrane absorber Cation Exchange Chromatography In one embodiment, the method of the invention includes at least one cation exchange step. In an exemplary embodiment a sample containing the peptide conjugate of interest is loaded onto a cation exchange resin in a loading buffer comprising a salt concentration below the concentration at which the peptide would elute from the column.

In one example, the pH of the loading buffer is selected so that the peptide conjugate of interest is retained on the cation exchange resin. Changing the pH of the buffer alters the charge of the peptide and increasing the pH of the buffer shortens the retention times with cation exchangers. Typically, cation exchanges are performed at 1.5 to 2 pH units below the peptide's pI. Alternatively, the cation exchange conditions are selected to preferentially bind impurities, while the purified peptide is found in the flow-through.

In one embodiment, the column is washed with several column volumes of buffer to remove unbound substances and those substances that bind weakly to the resin. Fractions are then eluted from the column using a salt gradient according to conventional methods. Sample fractions are collected from the column. One or more fraction containing high levels of the desired peptide and low levels of impurities are collected, and optionally pooled.

In an exemplary embodiment the cation exchangers used in the process of the current invention provide one of the primary purification steps of the purification process. In one embodiment, the cation exchanger removes undesired proteins from the mixture, which contains the peptide conjugate of interest. In another embodiment, the cation exchange step is useful to remove unwanted glycoforms of the purified polypeptide conjugate.

Cation exchange media are known to those of skill in the art. Exemplary cation exchange media are described, e.g., in *Protein Purification Methods, A Practical Approach*, Ed. Harris E L V, Angal S, IRL Press Oxford, England (1989); *Protein Purification*, Ed. Janson J C, Ryden L, VCH-Verlag, Weinheim, Germany (1989); *Process Scale Bioseparations for the Biopharmaceutical Industry*, Ed. Shukla A A, Etzel M R, Gadam S, CRC Press Taylor & Francis Group (2007), pages 188-196; *Protein Purification Handbook*, GE Healthcare 2007 (18-1132-29) and *Protein Purification, Principles, High Resolution Methods and Applications* ($2^{nd}$ Edition 1998), Ed. Janson J-C and Ryden L, the disclosures of which are incorporated herein by reference in their entirety. In an exemplary embodiment, cation exchange resins of use in the invention are selected from sulfonic acid (S) and carboxymethyl (CM) supports. In one embodiment, the cation exchanger is a sulfonic acid support (e.g. UNOsphereS, Bio-Rad Laboratories) or a sulphopropyl (SP) resin. In another embodiment, the cation exchange resin is selected from SPFF, SPHP sepharose, BigBeads SP, Capto S and the like. In one example, the cation exchanger is Source 15S.

Exemplary commercial cation exchange media are summarized below:
GE Healthcare:
SP-Sepharose FF
SP-Sepharose BB
SP-Sepharose XL
SP-Sepharose HP
Mini S
Mono S
CM Sepharose FF
Source 15S
Source 30S
Capto S
MacroCap SP
Streamline SP-XL
Streamline CST-1
Tosohaas Resins:

Toyopearl Mega Cap II SP-550 EC
Toyopearl Giga Cap S-650M
Toyopearl 650S, M and C
Toyopeal SP650S, M, and C
Toyopeal SP550C
JT Baker Resins:
Carboxy-Sulphon-5, 15 and 40 um
Sulfonic-5, 15, and 40 um
Applied Biosystems:
Poros HS 20 and 50 um
Poros S 10 and 20 um
Pall Corp:
S Ceramic Hyper D
CM Ceramic Hyper D
Merck KGgA Resins:
Fractogel EMD $SO_3$
Fractogel EMD COO—
Fractogel EMD SE Hicap
Fracto Prep So3
Biorad Resin:
Unosphere S
Sartorius Membrane:
Sartobind S membrane absorber The ion exchangers used in the methods of the invention are optionally membrane adsorbers rather than chromatographic resins or supports. In an exemplary embodiment, the membrane adsorber is a cation exchanger. In another exemplary embodiment the membrane adsorber is a sulfonic acid (S) cation exchanger (e.g. Sartobind S, Sartorius A G). The membrane adsorber is optionally disposable.

Mixed-Mode or Pseudo-Affinity Chromatography

In one embodiment, the peptide conjugate purification process of the invention includes mixed-mode or pseudo-affinity chromatography.

In one example, the process involves chromatography performed on ceramic or crystalline apatite media, such as hydroxyapatite (HA) chromatography and fluoroapatite (FA) chromatography. HA and FA chromatography are effective purification mechanisms, providing biomolecule selectivity, complementary to ion exchange and/or hydrophobic interaction techniques. Hydroxyapatite and fluoroapatite chromatography are known in the art. In one example, the apatite medium is Adhere MMC.

Hydroxyapatite

Exemplary hydroxyapatite sorbents of type I and type II are selected from ceramic and crystalline materials. Hydroxyapatite sorbents are available in different particle sizes (e.g. type 1, Bio-Rad Laboratories). In an exemplary embodiment, the particle size of the hydroxyapatite sorbent is between about 20 µm and about 180 µm, between about 20 µm and about 100 µm or between about 60 µm and about 100 µm. In a particular example, the particle size of the hydroxyapatite sorbent is about 80 µm.

In one embodiment, the hydroxyapatite sorbent is composed of cross-linked agarose beads with microcrystals of hydroxyapatite entrapped in the agarose mesh. Optionally, the agarose is chemically stabilized (e.g. with epichlorohydrin under strongly alkaline conditions). In one exemplary embodiment, the hydroxyapatite sorbent is HA Ultrogel (Pall Corporation).

Fluoroapatite

Exemplary type I and type II fluoroapatite sorbents are selected from ceramic (e.g., bead-like particles) and crystalline materials. Ceramic fluoroapatite sorbents are available in different particle sizes (e.g. type 1 and type 2, Bio-Rad Laboratories). In an exemplary embodiment the particle size of the ceramic fluoroapatite sorbent is from about 20 µm to about 180 µm, preferably about 20 to about 100 µm, more preferably about 20 µm to about 80 µm. In one example, the particle size of the ceramic fluoroapatite medium is about 40 µm (e.g., type 1 ceramic fluoroapatite). In another example, the fluoroapatite medium includes hydroxyapatite in addition to fluoroapatite. In a particular example, the fluoroapatite medium is Bio-Rad's CFT™ Ceramic Fluoroapatite.

The selection of the flow velocity used for loading the sample onto the hydroxyapatite or fluoroapatite column, as well as the elution flow velocity depends on the type of hydroxyapatite or fluoroapatite sorbent and on the column geometry. In one exemplary embodiment, at process scale, the loading flow velocity is selected from about 30 to about 900 cm/h, from about 150 to about 900 cm/h, preferably from about 500 to about 900 cm/h and, more preferably, from about 600 to about 900 cm/h.

In an exemplary embodiment, the pH of the elution buffer is selected from about pH 7 to about pH 9, and preferably from about pH 7.5 to about pH 8.0.

In one aspect the present invention provides a method of purifying a recombinant peptide by hydroxyapatite or fluoroapatite chromatography. The method includes the following steps: (a) desalting a mixture containing the peptide, forming a desalted mixture (e.g. by gel filtration) that has a salt conductivity, which is sufficiently low to increase the peptide-binding capacity of the hydroxyapatit or fluoroapatite resin; (b) applying the desalted mixture to a hydroxyapatite or fluoroapatite resin; (c) washing the hydroxyapatite or fluoroapatite resin, thereby eluting unwanted components from the resin; (d) eluting the peptide from the resin with an elution buffer that optionally contains an amino acid; and (e) collecting one or more eluate fraction containing the peptide.

Desalting

In one embodiment, the mixture containing the peptide of interest is desalted prior to subjecting the mixture to HA or fluoroapatite chromatography. The desalting step increases the capacity of the apatite column to bind the peptide of interest. In one embodiment, the apatite column capacity (amount of peptide per liter of resin), increases with decreasing salt conductivity of the load, which contains the peptide.

In an exemplary embodiment, in which the load is desalted, the mass loading of peptide per liter of HA resin is from about 1 to about 25 g/L, from about 1 to about 20 g/L, preferably from about 1 to about 15 g/L and more preferably from about 1 to about 10 g/L.

In another exemplary embodiment, the conductivity of the load can be decreased using a method selected from desalting and diluting.

In an exemplary embodiment, the conductivity of the loading buffer is lowered by desalting and preferred conductivities are from about 0.1 to about 4.0 mS/cm, preferably from about 0.1 to about 1.0 mS/cm, more preferably from about 0.1 to about 0.6 mS/cm and, still more preferably, from about 0.1 to about 0.4 mS/cm.

In one example, desalting of peptide conjugate solutions is achieved using membrane filters wherein the membrane filter has a MWCO smaller than the peptide/protein of interest. The peptide/protein is found in the retentate and is reconstituted in a buffer of choice. However, when purifying peptides of relatively low molecular weight (e.g. EPO), the MWCO of the membrane used for desalting must be relatively small in order to avoid leaking of the peptide through the membrane pores. However, filtering a large volume of liquid through a small MWCO membrane (e.g. with a pore size of about 5 kDa), typically requires large membrane areas and the filtering process is time consuming.

Therefore, in one embodiment, desalting of the HA or fluoroapatite chromatography load is accomplished using size-exclusion chromatography (e.g. gel filtration). The technique separates molecules on the basis of size. Typically, high molecular weight components can travel through the column more easily than smaller molecules, since their size prevents them from entering bead pores. Accordingly, low-molecular weight components take longer to pass through the column. Thus, low molecular weight materials, such as unwanted salts, can be separated from the peptide of interest.

In an exemplary embodiment, the column material is selected from dextran, agarose, and polyacrylamide gels, in which the gels are characterized by different particle sizes. In another exemplary embodiment, the material is selected from rigid, aqueous-compatible size exclusion materials. An exemplary gel filtration resin of the invention is Sepharose G-25 resin (GE Healthcare).

In an exemplary embodiment, desalting is performed subsequent to cation exchange chromatography (e.g. after Source 15S chromatography).

Addition of an Amino Acid to the Elution Buffer

In one embodiment, an amino acid is added to the elution buffer, which is used to elute the peptide of interest from the HA or fluoroapatite resin. In an exemplary embodiment the amino acid is added to the elution buffer at a final concentration of about 5 mM to about 50 mM, about 10 mM to about 40 mM, preferably about 15 mM to about 30 mM and, more preferably, about 20 mM.

In one embodiment, the addition of an amino acid (e.g. glycine) to the elution buffer increases the step recovery of peptide from HA chromatography when compared to the recovery obtained without the addition of an amino acid. In an exemplary embodiment, the recovery of peptide is increased by addition of the amino acid at least about 1% to about 20%, by at least about 1% to about 15%, by at least about 1% to about 10%, preferably by at least about 1% to about 7% and, more preferably, by about 5%.

In another exemplary embodiment, the addition of an amino acid (e.g. glycine) causes the elution peak of the purified peptide to be sharper. Thus, less peptide is recovered in the tail fractions of the peak and more peptide is recovered in the main peak. In another exemplary embodiment, the addition of an amino acid (e.g. glycine) does not decrease the purity of the product from HA chromatography.

In an exemplary embodiment, the amino acid is glycine. In a preferred embodiment, glycine is added to the elution buffer at a final concentration of 20 mM.

Hydrophobic Interaction Chromatography (HIC)

Hydrophobic interaction chromatography (HIC) is a liquid chromatography technique that separates biomolecules based on differences in their surface hydrophobicity. For example, hydrophobic amino acid side chains exposed on the surface of a polypeptide, can interact with hydrophobic moieties on the HIC matrix. The amount of exposed hydrophobic amino acids differs between polypeptides and so does the ability of polypeptides to interact with HIC gels. Hydrophobic interaction between a biomolecule and HIC matrix is typically enhanced by high ionic strength buffers, and HIC of biomolecules is most often performed at high salt concentrations. The elution of the peptide of interest from the column is then initiated by decreasing salt gradients.

In one embodiment, the HIC resin is selected for optimal resolution of different polypeptide glycoforms. Exemplary HIC resins useful in the methods of the invention are described, e.g., in *Protein Purification Methods, A Practical Approach*, Ed. Harris E L V, Angal S, IRL Press Oxford, England (1989) page 224, *Protein Purification*, Ed. Janson J C, Ryden L, VCH-Verlag, Weinheim, Germany (1989) pages 207-226, *Process Scale Bioseparations for the Biopharmaceutical Industry*, Ed. Shukla A A, Etzel M R, Gadam S, CRC Press Taylor & Francis Group (2007), pages 197-206, *Hydrophobic Interaction and Reversed Phase Chromatography, Principles and Methods*, GE Healthcare 2007 (11-0012-69), *Protein Purification Handbook*, GE Healthcare 2007 (18-1132-29) and *Protein Purification, Principles, High Resolution Methods and Applications* ($2^{nd}$ Edition 1998), Ed. Janson J-C and Ryden L, "Hydrophobic Interaction Chromatography, page 283, the disclosures of which are incorporated herein by reference in their entirety.

HIC media are distinguished by the hydrophobic moiety that they carry, by the particle size (e.g. bead size), the pore size and the density of the hydrophobic moieties on the HIC matrix (e.g. low substitution or high substitution). In an exemplary embodiment, the hydrophobic moieties of the column matrix are members selected from alkyl groups, aromatic groups and ethers. Exemplary hydrophobic alkyl groups include lower alkyl groups, such as n-propyl, isopropyl, n-butyl, iso-butyl, and n-octyl. Exemplary aromatic groups include substituted and unsubstituted phenyl.

In another exemplary embodiment the matrix of the HIC medium is a member selected from agarose, sepharose (GE Healthcare), polystyrene, divinylbenzene, and combinations thereof. Exemplary HIC resins include Butyl Fast Flow and Phenyl Fast Flow (e.g., GE Healthcare) in either low or high substituted versions. In a preferred embodiment, the HIC resin is a phenyl resin. In one particular example, the HIC resin is Phenyl 650S or Phenyl 650M (e.g., Tosohaas, Toyopearl).

In one example, the HIC medium is selected from the following commercial resins:
GE Healthcare HIC Resins:
Butyl Sepharose 4 FF
Butyl-S Sepharose FF
Octyl Sepharose 4 FF
Phenyl Sepharose BB
Phenyl Sepharose HP
Phenyl Sepharose 6 FF High Sub
Phenyl Sepharose 6 FF Low Sub
Source 15ETH
Source 15ISO
Source 15PHE
Capto Phenyl (prototype resin)
Capto Butyl (prototype resin)
Streamline Phenyl
Tosohaas HIC Resins:
TSK Ether 5PW (20 um and 30 um)
TSK Phenyl 5PW (20 um and 30 um)
Phenyl 650S, M, and C
Butyl 650S, M and C
Hexyl-650M and C
Ether-650S and M
Butyl-600M
Super Butyl-550C
PPG-600M
Waters HIC Resins:
YMC-Pack Octyl Columns-3, 5, 10P, 15 and 25 um with pore sizes 120, 200, 300A
YMC-Pack Phenyl Columns-3, 5, 10P, 15 and 25 um with pore sizes 120, 200 and 300 A
YMC-Pack Butyl Columns-3, 5, 10P, 15 and 25 um with pore sizes 120, 200 and 300 A
CHISSO Corporation HIC Resins:
Cellufine Butyl
Cellufine Octyl Cellufine Phenyl
JT Baker HIC Resin:
WP HI-Propyl (C3)
Biorad HIC Resins:
Macroprep t-Butyl
Macroprep methyl
Applied Biosystems HIC Resin:
High Density Phenyl—HP2 20 um In a further exemplary embodiment, the amount of polypeptide conjugate loaded onto the HIC medium is between about 0.05 and about 1.0 mg conjugate/mL resin. In one example, the loaded amount of polypeptide conjugate is selected between about 0.05 and 0.3 mg conjugate/mL resin. In another example, the HIC medium is loaded with between about 0.1 and about 0.2 mg conjugate/mL resin (e.g., 0.15-0.18 mg/mL). In another embodiment, the amount of polypeptide conjugate loaded onto the HIC column is optimized for recovery of peptide conjugate and resolution of glycoforms. In one embodiment, in which the polypeptide conjugate is EPO-PEG$_3$, the HIC loading conditions are selected to create an HIC eluate that includes less than about 8%, preferably less than about 7%, more preferably less than about 6%, even more preferably less than about 5% and most preferably less than about 4% of EPO-PEG$_2$.

In one embodiment, the loading buffer (the buffer in which the purified polypeptide conjugate is applied to the HIC column) is selected to bind the purified polypeptide conjugate to the HIC medium. Unbound impurities are then washed off the column using a HIC wash buffer. Consequently, polypeptide conjugates are eluted using an HIC elution buffer.

In an exemplary embodiment, the HIC loading buffer, the HIC wash buffer and the HIC elution buffer each contain one or more salts, such as sodium acetate (NaOAc), sodium chloride (NaCl), sodium sulfate (Na$_2$SO$_4$) and sodium phosphate. The concentration ranges for these and other salts are generally optimized for each type of HIC resin to affect optimal binding of the polypeptide conjugate being purified.

In one embodiment, the HIC loading buffer includes sodium sulfate (Na$_2$SO$_4$) or ammonium sulfate, (NH$_4$)$_2$SO$_4$. In an exemplary embodiment, the concentration of sodium- or ammonium sulfate in the loading buffer is about 100 mM to about 1200 mM. In another exemplary embodiment, the concentration of sodium sulfate in the HIC loading buffer is about 300 mM to about 1100 mM, about 300 mM to about 1000 mM, about 300 mM to about 900 mM, about 300 mM to about 800 mM, about 300 mM to about 700 mM, about 300 mM to about 600 mM or about 300 mM to about 500 mM. In yet another embodiment, the concentration of sodium sulfate in the HIC loading buffer is about 400 mM to about 800 mM. In a further exemplary embodiment, the concentration of sodium sulfate in the HIC loading buffer is about 500 mM to about 700 mM, and preferably about 600 mM.

In one embodiment, the HIC loading buffer, HIC wash buffer and HIC elution buffer include sodium phosphate. In one example, the concentration of sodium phosphate in any of these buffers is selected between about 5 mM and about 70 mM. In another example, the concentration of sodium phosphate in the HIC wash buffer is selected between about 10 mM and about 50 mM, between about 10 mM and about 30 mM or between about 20 mM and about 30 mM. In one particular example, the sodium phosphate concentration in the HIC wash buffer and elution buffer is about 25 mM.

In another exemplary embodiment, the HIC wash buffer has a pH of about 4.0 to about 8.0. In one example, the pH of the HIC wash buffer is selected from about 5.0 to about 8.0. In another example, the pH is selected from about 6 to about 8. In yet another example, the pH is selected from about 6.5 to about 8.0. In a further embodiment, the pH of the HIC wash buffer is selected from about 7.0 to about 8.0, from about 7.0 to about 7.9, from about 7.0 to about 7.8, from about 7.0 to about 7.7, from about 7.0 to about 7.6 or from about 7.0 to about 7.5. In one particular example, the pH of the HIC wash buffer is about 7.5.

In one embodiment, the purified polypeptide conjugate is eluted from the HIC resin using a gradient of decreasing sodium sulfate concentration. Optionally, the elution buffer does not contain any sodium sulfate.

In another embodiment, HIC is employed as a method to separate polypeptide glycoforms, each covalently linked to at least one poly(alkylene oxide) moiety. In one example, the elution gradient profile is selected to affect optimal resolution of different polypeptide glycoforms contained in the purified mixture. In one embodiment, the HIC elution buffer includes 25 mM sodium phosphate and a combination of gradient and hold periods spanning a range of about 600 mM sodium sulfate to no sodium sulfate in the phosphate buffer is employed to elute polypeptide conjugates from the HIC medium.

In an exemplary embodiment, HIC is performed subsequent to anion exchange chromatography. In one example, the flow-through from the anion exchanger, which contains the partially purified polypeptide conjugate is conditioned for hydrophobic interaction chromatography. In one example, the anion exchange flow-through may be diluted with a buffer suitable as a loading buffer for HIC. For example, the anion exchange flow-through can be diluted with a buffer containing sodium sulfate to adjust the sodium sulfate concentration in the HIC load (e.g., a sodium sulfate concentration suitable to bind the polypeptide conjugate to the HIC medium, e.g., about 600 mM). Optionally, the anion exchange flow-through is concentrated before dilution. In another example, the anion exchange flow-through is subjected to diafiltration/ultrafiltration for concentration and/or buffer exchange.

III.h) Description of an Exemplary Purification Process

In one embodiment of the invention, the polypeptide conjugate of interest is purified from a mixture (e.g., a reaction mixture, such as a glycoPEGylation reaction) using the exemplary purification process outlined in FIG. 1. In a first step, the product of the glycoPEGylation reaction is subjected to anion exchange chromatography/filtration (e.g., using a Sartobind Q resin). In one example, impurities are bound by the anion exchange medium, while the purified polypeptide conjugate is found in the flow-through. In one embodiment, this anion exchange step is useful to remove catalytic enzymes used in a glycan remodeling and/or glycomodification (e.g., glycoPEGylation) reaction performed prior to the anion exchange procedure. In one example, the anion exchange step is useful to isolate the polypeptide conjugate from at least one glycosyltransferase contained in the glycoPEGylation reaction mixture.

In a second step, the flow-through of the anion exchange step containing the partially purified polypeptide conjugate is conditioned and then loaded onto a hydrophobic interaction chromatography resin. In one example, the HIC medium is Phenyl 650S.

In one embodiment, the anion exchange flow-through is conditioned to generate a HIC loading sample that includes a sufficient salt concentration to affect binding of the polypeptide conjugate to the HIC medium. In one embodiment, the anion exchange flow-trough is diluted with a buffer containing sodium sulfate. In one embodiment, the dilution buffer contains sufficient sodium sulfate to generate a HIC loading sample having a sodium sulfate concentration between about 500 mM and about 700 mM. In one example, the anion exchange flow-through is diluted so that the HIC loading sample includes about 600 mM of sodium sulfate. After the sample is applied to the column, the HIC resin is washed with a wash buffer to elute unbound impurities. In one example the HIC wash buffer is a phosphate buffer. In another example, the HIC wash buffer contains about 25 mM sodium phosphate at a pH of about 7.5.

Subsequent to washing, the polypeptide conjugate is eluted from the HIC medium using an elution buffer. In one example, the polypeptide conjugate is eluted from the HIC medium using a phosphate buffer (e.g., 25 mM sodium phosphate at pH 7.5) and a gradient of decreasing sodium sulfate in the phosphate buffer. In one example, the conjugate is eluted using a gradient from about 600 mM to about 0 mM sodium sulfate. Eluate fractions are collected and optionally analyzed for product content. Product containing fractions are pooled and the resulting HIC pool is optionally conditioned for loading onto a cation exchange medium.

In one embodiment, the HIC pool is concentrated and the buffer is exchanged using diafiltration. In one example, the diafiltration membrane has a MWCO of 10 kDa. In another example, the volume of the HIC pool is reduced to between about 1/30 and about 1/10 of the original volume. In a particular example, the HIC pool volume is reduced to about 1/20 of the original volume. The buffer may then be exchanged, for example, by diluting the sample with the new buffer and subsequently re-concentrating the sample. The dilution and re-concentration steps may be repeated (e.g., 2-6 times) until the new buffer has the desired composition (e.g., the desired salt conductivity).

The partially purified polypeptide conjugate may be transferred into the desired buffer using a two step buffer exchange. In the first buffer exchange step, the buffer may be changed to a phosphate buffer that does not include sodium sulfate. The pH of the resulting conjugate solution may optionally be adjusted (e.g., using sodium acetate. In a second buffer exchange step, the buffer may be changed to a buffer system suitable for loading onto a cation exchanger. For example, the second buffer may include about 10 mM sodium acetate at a pH of about 5.4. In another example, the loading buffer for the cation exchange step has a salt conductivity between about 1.0 and about 3.0 mS/cm (e.g., about 1.5 mS/cm).

In a third step, the diafiltered HIC pool is subjected to cation exchange. In one embodiment, the cation exchanger is Source 15S. In one example, the cation exchange medium is useful to further reduce the content of unwanted glycoforms of the purified polypeptide conjugate.

In one example, the partially purified polypeptide conjugate is applied to the cation exchange medium and unbound impurities are eluted using a cation exchange wash buffer (e.g., 10 mM sodium acetate, pH 5.4). The bound polypeptide conjugate is then eluted using a cation exchange elution buffer. In one embodiment, the conjugate is eluted using increasing NaCl concentrations in the above wash buffer. For example, the conjugate is eluted using a gradient of 0-0.5 M NaCl. In one embodiment, the gradient elution profile, which may include a combination of gradient and hold periods, is selected for optimized glycoform resolution. Eluate fractions are collected and optionally analyzed (e.g., for product content and purity). Selected product containing fractions are pooled to form a cation exchange pool.

In one embodiment, the cation exchange pool is concentrated and diafiltered into a storage buffer. In one example, this diafiltration step also uses a 10 kDa MWCO membrane. In one embodiment, the volume of the cation exchange pool is reduced to about 1/100 to about 1/25 of its original volume (e.g., about 1/50 of the original volume). The concentrated cation exchange pool is then subjected to buffer exchange, for example, by diluting the sample with the new buffer and subsequently re-concentrating the sample. The dilution and re-concentration step may be repeated (e.g., 2-6 times) until the new buffer has the desired composition. The final retentate is reconstituted into a storage buffer. Exemplary storage buffers include those having a sodium chloride concentration that is in the physiological range. For example, the storage buffer may be a sodium acetate buffer including about 150 mM NaCl. The concentrated product pool is reconstituted in the storage buffer to reach a desired peptide concentration. In one embodiment, the final conjugate concentration is selected between about 0.5 and about 2 mg/mL. The final solution is optionally sterile filtered, for example through a cellulose acetate membrane.

The purification process outlined in FIG. 1, may optionally include an additional chromatography step. In one embodiment, the process includes a hydroxyapatite (HA) or fluoroapatite chromatography step. In one example, the apatite chromatography is performed after anion exchange chromatography. In another example, the apatite chromatography is performed after HIC. In yet another example, the apatite chromatography is performed after cation exchange chromatography. The partially purified polypeptide conjugate solution may be desalted, for example, using a size exclusion column (e.g. G25) to lower the salt conductivity of the conjugate solution in preparation for apatite chromatography.

In an exemplary embodiment, the polypeptide conjugate purified by the above described process is an EPO-conjugate.

II. Compositions

In another aspect the invention provides a composition made by a method of the invention. In one embodiment, the invention provides a composition including a first polypeptide conjugate, said first polypeptide conjugate having a first number of poly(alkylene oxide) moieties, each of the poly(alkylene oxide) moieties covalently linked to the first polypeptide via an intact glycosyl linking group. The composition is made by a method including: (a) contacting a mixture comprising the first polypeptide conjugate with a hydrophobic interaction chromatography (HIC) medium; and (b) eluting the first polypeptide conjugate from the hydrophobic interaction chromatography medium.

In another aspect, the invention provides an isolated first polypeptide conjugate made by a method comprising: separating the first polypeptide conjugate including a first number of poly(alkylene oxide) moieties covalently linked to a first polypeptide, from a second polypeptide conjugate comprising a second number of poly(alkylene oxide) moieties covalently linked to a second polypeptide. In one embodiment, the first number is selected from 1 to 20 and the second number is selected from 0-20. In another embodiment, the first number and the second number are different. The two polypeptide conjugates are separated by: (a) contacting a mixture comprising the first polypeptide conjugate and the second polypeptide conjugate with a hydrophobic interaction chromatography (HIC) medium; and (b) eluting the first polypeptide conjugate from the hydrophobic interaction chromatography medium.

In one example, according to any of the above embodiments, the first polypeptide is a member selected from erythropoietin (EPO), bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, granulocyte colony stimulating factor (G-CSF), granulocyte-macrophage colony stimulating factor (GM-CSF), interferon alpha, interferon beta, interferon gamma, $\alpha_1$-antitrypsin ($\alpha$-1 protease inhibitor), glucocerebrosidase, tissue-type plasminogen activator (TPA), interleukin-2 (IL-2), leptin, hirudin, urokinase, human DNase, insulin, hepatitis B surface protein (HbsAg), chimeric diphtheria toxin-IL-2, human growth hormone (hGH), human chorionic gonadotropin (hCG), thyroid peroxidase (TPO), alpha-galactosidase, alpha-L-iduronidase, beta-glucosidase, alpha-galactosidase A, acid $\alpha$-glucosidase (acid maltase), anti-thrombin III (AT III), follicle stimulating hormone (FSH), glucagon-like peptide-1 (GLP-1), glucagon-like peptide-2 (GLP-2), fibroblast growth factor 7 (FGF-7), fibroblast growth factor 21 (FGF-21), fibroblast growth factor 23 (FGF-23), Factor X, Factor XIII, prokinetisin, extendin-4, CD4, tumor necrosis factor receptor (TNF-R), $\alpha$-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-$\alpha$, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor. Mutant forms of any of the above polypeptides are also within the scope of the invention.

In yet another aspect, the invention provides a composition including a first erythropoietin (EPO) conjugate, the first EPO conjugate having a first number of poly(alkylene oxide) moieties covalently linked to an EPO polypeptide via a glycosyl linking group (e.g., an intact glycosyl linking group). The composition is made by a method including: (a) contacting a mixture including the first EPO conjugate with an anion exchange medium; (b) eluting the first EPO conjugate from the anion exchange medium, forming a first eluate comprising the first EPO conjugate; (c) contacting the first eluate with a hydrophobic interaction chromatography (HIC) medium; and (d) eluting the first EPO conjugate from the hydrophobic interaction chromatography medium.

In a further aspect, the invention provides a pharmaceutical formulation including a composition made by a method of the invention and a pharmaceutically acceptable carrier. In one embodiment, the pharmaceutical formulation includes an isolated polypeptide conjugate made by a method of the invention and a pharmaceutically acceptable carrier. In one example according to this embodiment, the isolated polypeptide conjugate is an EPO-conjugate.

III. Methods of Treatment

In another aspect, the invention provides methods of treatment utilizing a composition (e.g., an isolated polypeptide conjugate) made by a method of the invention. In one embodiment, the invention provides a method of treating a condition in a subject in need thereof, the condition characterized by compromised red blood cell production in the subject, the method comprising: administering to the subject an amount of a composition of the invention, effective to ameliorate the condition in the subject. In one example, the subject is a mammal, such as a human. In another example, the composition includes an EPO conjugate made by a method of the invention.

In another embodiment, the invention provides a method of treating a tissue injury in a subject in need thereof. In one example, the injury is caused by a member selected from ischemia, trauma, inflammation and contact with a toxic substance. The method includes: administering to a subject an amount of a composition made by a method of the invention (e.g., an isolated polypeptide conjugate) that is effective in ameliorating the damage associated with the tissue injury. In one example, the subject is a mammal, such as a human. In another example, the composition includes an EPO conjugate made by a method of the invention.

In another embodiment, the invention provides a method of enhancing red blood cell production in a mammal, said method comprising administering to said mammal a composition made by a method of the invention. In one example, the subject is a mammal, such as a human. In another example, the composition includes an EPO conjugate made by a method of the invention.

The following examples are provided to illustrate the methods of the present invention, but not to limit the claimed invention.

EXAMPLES

Analytical Methods

Protein Concentration Determination

The protein concentration was determined using either a UV method (280 nm) or was determined using BCA Protein Assay kit according to manufacture's instructions (Pierce).

Conductivity Measurement

The conductivity of process samples and buffers was measured using a conductivity probe (VWR 2052) according to the manufacturer's instructions.

EPO-PEG Purity and PEG State Assay (C3 RP-HPLC)

The ratio of each EPO-PEG form [EPO-(SA-PEG-10 kDa)$_{1-4}$] was determined using $C_3$ RIP HPLC chromatography (Zorbax 300SB-C3, 150×2.1 mm, 5 micron, 45° C.). The HPLC was performed using the following solutions: A, 0.1% TFA in water, and B, 0.09% TFA in ACN. The mobile phase was performed as a gradient from 42-55% B over 14 min, 55-95% B over 2 min, a 2 min wash at 95% B and then 95-42% B over 2 min. The total time conduct the chromatography was 30 min using a flow rate of 0.6 mL/min. Mixture 1 was used as a reference standard to test system suitability. The injection volume was varied to give a standard injection concentration of 5 to 10 µg of EPO-(SA-PEG-10 kDa)$_3$ based on protein. Protein absorbance was detected at 214 nm and the peak areas of the EPO species were used to determine the protein purity. All peaks were integrated using 32 karat software. The EPO-(SA-PEG-10 kDa)$_4$ peak could typically not be integrated accurately due to its small area.

Protein Purity and Aggregation by SEC HPLC.

The EPO-(SA-PEG-10 kDa)$_3$ isoform purity and aggregation were determined by SEC HPLC chromatography (TSK-gel G5000PWxL, 7.8×300 mm, 10 micron, 4° C.). The isocratic mobile phase (100 mM sodium phosphate, 150 mM sodium chloride, pH 7.0) was used to perform the method at a flow rate of 0.5 mL/min.

Example 1

Development of a Purification Process for the Purification of GlycoPEGylated EPO Using Hydrophobic Interaction Chromatography This example describes the development of an isolation process for the isolation of EPO conjugates from a glycoPEGylation reaction mixture. The resulting process is characterized by high overall EPO conjugate recovery and produces the desired EPO conjugate [EPO-(SA-PEG-10 kDa)$_3$] in high purity. The composition produced by the process is essentially free of other EPO-PEG glycoforms, such as mono-, di- and tetra-PEGylated EPO conjugates.

The desired EPO-PEG conjugate is a glycoPEGylated erythropoietin protein that contains three 10 kDa mPEG groups attached to each of the three monoantennary N-linked glycans. The EPO polypeptide is produced by expression of the protein from Sf9 cells using a Baculovirus infection protocol. The insect cell expression system produces EPO with three N-linked glycans, at $Asn^{24}$, Asn and $Asn^{83}$, each containing a trimannosyl core as the predominant species. A variety of other glycan structures are present in small amounts that vary with fermentation conditions. The other structures include trimannosyl core with an additional GlcNAc, higher mannose forms ($Man_4$, $Man_5$), missing glycans, and GlcNAc-(Fuc) stub arising as a result of an endoglycosidase-type (Endo-H) activity. A small percentage of the EPO molecules contain O-linked glycans at $Ser^{126}$. A very low level (<1%) of phosphorylcholine-linked glycans (PC-glycan) has also been identified in the insect cell-derived EPO. Upon GlycoPEGylation with MBP-GnT1, MBP-GalT1, and MBP-ST3Gal3 or ST3Gal3 with CMP-SA-PEG-10 kDa, the predominant product is EPO-(SA-PEG-10 kDa)$_3$ which contains three PEGylated mono-antennary N-linked glycans. EPO-(SA-PEG-10 kDa)$_{1,2}$ are also present in lesser amounts, arising from the EPO forms missing one or more glycans or containing one or more GlcNAc-stub glycans. EPO-(SA-PEG-10 kDa)$_4$ (and higher) are produced at very low levels. These higher PEGylated species are thought to result from the GlycoPEGylation of the EPO glycoforms which contain the tri-mannosyl core with an additional GlcNAc on the Man$\alpha$1,6 branch. Both branches of these glycans can be built out and PEGylated under the reaction conditions, resulting in biantennary PEGylated glycans on a tetra-PEG (or higher) EPO species. Exemplary EPO glycoforms are depicted in FIG. 3.

GlycoPEGylated EPO isolated using reversed-phase chromatography and cation exchange chromatography (e.g., on SP-Sepharose HP) provided a composition containing greater than or equal to about 85% EPO-(SA-PEG-10 kDa)$_3$, about 3-14% EPO-(SA-PEG-10 kDa)$_2$, about 1-8% EPO-(SA-PEG-10 kDa)$_{4-6}$ and less than or equal to about 1% EPO-(SA-PEG-10 kDa)$_1$. In the following, the above composition is referred to as Mixture 1.

Efforts were undertaken to replace the reverse phase chromatography step with another chromatography step, which does not employ organic solvents but is capable of resolving EPO glycoforms. Large amounts of organic solvents are associated with environmental concerns and may not be used in certain facilities processing biologic drug products. In addition, the stability of EPO-PEG conjugates, such as EPO-(SA-PEG-10 kDa)$_3$ in solutions with a high concentration of organic solvents (e.g., acetonitrile) is a concern. Hydrophobic Interaction Chromatography (HIC) was investigated as a potential replacement for the reverse phase chromatography step.

It was discovered that HIC was capable of separating different PEG states (glycoforms) contained in a mixture, which results from a glycoPEGylation process (e.g., fractionation of isoforms EPO-(SA-PEG-10 kDa)$_{1-4}$). The HIC purification method was optimized by evaluating a variety of HIC resins and process parameters. A process based on Phenyl 650S resin (e.g., Tosohaas, Toyopearl) was selected for incorporation into the new isolation process.

Also incorporated into the new process was an anion exchange step, which is useful to remove enzyme components of the glycoPEGylation reaction. Enzymes are bound by the anion exchange medium, while the EPO-PEG conjugates EPO-(SA-PEG-10 kDa)$_{1-6}$ are found in the flow through.

1.1. Methods

Hydrophobic Interaction Chromatography Conditions (Initial Resin Screen)

Initial HIC resin screening experiments were performed using Tricorn 5 columns packed to 5 cm bead heights. Selected hydrophobic interaction chromatography resins are summarized in Table 1, below.

TABLE 1

Summary of Evaluated HIC Resins and Elution Conditions

| | Resin | Buffer A | Buffer B |
|---|---|---|---|
| HIC Resins Set I: | | | |
| A | Ether-5PW | 30 mM Na phosphate, pH 6.5 | Buffer A + 1 M NaCl, pH 6.5 |
| B | Butyl-S-FF | 25 mM Na phosphate, pH 7.0 | Buffer A + 1 M $(NH_4)_2SO_4$, pH 7.0 |
| C | Butyl-FF | 25 mM Na phosphate, pH 7.0 | Buffer A + 1 M $(NH_4)_2SO_4$, pH 7.0 |
| D | Octyl-FF | 25 mM Na phosphate, pH 7.0 | Buffer A + 1 M $(NH_4)_2SO_4$, pH 7.0 |
| E | Phenyl-FF Low sub | 25 mM Na phosphate, pH 7.0 | Buffer A + 1 M $(NH_4)_2SO_4$, pH 7.0 |
| F | Phenyl-FF High sub | 25 mM Na phosphate, pH 7.0 | Buffer A + 1 M $(NH_4)_2SO_4$, pH 7.0 |
| HIC Resin Set II: | | | |
| G | Butyl 650M | 25 mM Na phosphate, pH 7.0 | Buffer A + 1 M $(NH_4)_2SO_4$, pH 7.0 |
| H | Phenyl 650M | 25 mM Na phosphate, pH 7.0 | Buffer A + 4 M NaCl, pH 7.0 |
| I | Phenyl 650M | 25 mM Na phosphate, pH 7.0 | Buffer A + 1 M $(NH_4)_2SO_4$, pH 7.0 |
| J | Phenyl-FF Low sub | 25 mM Na phosphate, pH 7.0 | Buffer A + 4 M NaCl, pH 7.0 |
| K | Phenyl-FF Low sub | 25 mM Na phosphate, pH 7.0 | Buffer A + 1 M $(NH_4)_2SO_4$, pH 7.0 |
| HIC Resin Set III: | | | |
| L | Phenyl 650M | 20 mM NaOAc, pH 5.0 | Buffer A + 1 M $Na_2SO_4$ + 0.5 M NaCl, pH 5.0 |
| M | Phenyl 650M | 20 mM NaOAc, pH 5.0 | Buffer A + 1 M $Na_2SO_4$, pH 5.0 |
| N | Phenyl 650M | 25 mM Na phosphate, pH 7.0 | Buffer A + 1 M $Na_2SO_4$, pH 7.0 |
| O | Phenyl 650M | 25 mM Na phosphate, 20% ethylene glycol, pH 7.0 | Buffer A + 4 M NaCl, pH 7.0 |
| P | Phenyl 650M | 25 mM Na phosphate, pH 7.0 | Buffer A + 4 M NaCl, pH 7.0 |
| Q | Phenyl 650M | 25 mM Na phosphate, pH 7.0 | Buffer A + 1 M $(NH_4)_2SO_4$, pH 7.0 |

A Tricorn 5 column packed with 1 mL (0.5 cm×5 cm) of the appropriate resin (Table 1) or a prepacked HiTrap column (1 mL, 0.7 cm×2.5 cm) was attached to an AKTA FPLC system (GE Healthcare). Product elution was monitored by absorbance at 280 nm. Each column was equilibrated with 5 column volumes (CV) of Buffer B (as indicated in Table 1). Mixture 1 (100 mcg, 250 mcL) was diluted to 1.25 mL with 1 mL of Buffer B and injected using a 2 mL sample loop. The unbound material was washed with 5 CV of Buffer B. The EPO-(SA-PEG-10 kDa)$_3$ was eluted with the following gradient elution using Buffer A (as indicated in Table 1): 100-0% Buffer B over 20 CV followed by 0% Buffer B for 5 CV. All steps were performed at 0.64 mL/min (196 cm/hr). The resulting chromatograms were compared and selected fractions were analysed by SDS-PAGE. Resins were selected for their capability to retain the EPO-PEG conjugates, their capability to resolve different glycoforms and peak shapes.

1.2. Results

The following Hydrophobic Interaction Chromatography (HIC) resins; Butyl-FF, Butyl-S-FF, Octyl-FF, Phenyl-FF High sub and Phenyl-FF Low sub were initially tested by injecting Mixture 1 in buffer B: 25 mM Na phosphate, 1 M ammonium Sulfate, pH 7.0. Under the conditions tested, the Phenyl-FF Low sub appeared to be the best resin for the binding and elution of Mixture 1. Mixture 1 was not bound by Butyl-S—FF. Butyl-FF, Octyl-FF, and Phenyl-FF High sub bound Mixture 1 fairly tightly and the elution peaks were extremely broad (15 CV).

In a second round of HIC investigation, Phenyl-FF Low sub was compared to Phenyl 650M and Butyl 650M using either 25 mM Na phosphate, 1 M ammonium Sulfate, pH 7.0 or 25 mM Na phosphate, 4 M ammonium Sulfate, pH 7.0 as binding buffer (loading buffer). Butyl 650M was only tested with ammonium sulfate and resulted in a very wide and tailing elution peak. Both Phenyl 650M and Phenyl-FF low sub had a more symmetric peak shape when using sodium sulfate. The use of sodium chloride resulted in extremely broad elution peaks.

A third round of HIC testing, compares the Phenyl 650M purification of Mixture 1 with different buffers. Buffer B: 1 M Na Sulfate+0.5 M NaCl+20 mM NaOAc, pH 5.0 was tested as this condition had worked for purification of the EPO intermediate prior to PEGylation. This condition resulted in a broad elution peak with multiply bumps, as did the same buffer without 0.5M NaCl (1 M Na Sulfate+20 mM NaOAc, pH 5.0). Phenyl 650M was tested using Mixture 1 bound to the column using 4 M NaCl+buffer A, pH 7.0 and the elution was performed with 25 mM Na phosphate, 20% ethylene glycol, pH 7.0. The addition of ethylene glycol did not significantly improve the broad elution profile resulting from NaCl in buffer B. Hence, conditions N and Q were found to be superior to other tested conditions. Sodium sulfate, which is preferred in manufacturing gave an elution profile as good or better that the ammonium sulfate.

Optimization of Chromatography Conditions (HIC)
Elution of Glycosyltransferases from Tosohaas Phenyl 650 M Resin A Tricorn 5 column packed with a 1 mL (0.5 cm×5 cm) Phenyl 650M resin was attached to an AKTA FPLC system continuously monitoring absorbance at A280. The column was equilibrated with 5 column volumes (CV) of Buffer B (1 M sodium sulfate, 25 mM sodium phosphate, pH 7.0). Product elution was monitored by absorbance at 280 nm.

Four separate sample injections of the following materials were applied to the column using a 2 mL sample loop: 1. Mixture 1 (100 mcg, 250 mcL) diluted to 1.25 mL with 1 mL of Buffer B. 2. MBP-SBD-ST3Gal3 (98 mcL, 98 mcg) diluted to 1.225 mL with 1.127 mL of Buffer B. 3. MBP-GnT1 (196 mcL, 57.4 mcg) diluted to 1.225 mL with 1.029 mL of Buffer B. 4. MBP-GalT1 (196 mcL, 186 mcg) diluted to 1.225 mL with 1.029 mL Buffer B.

After each sample was injected, any unbound material was washed from the column using 5 CV of Buffer B. Any bound material was eluted from the column using a gradient using Buffer A (25 mM sodium phosphate, pH 7.0): 100-0% Buffer B over 20 CV followed by 0% Buffer B for 5 CV (Table 1, Set III, N). Chromatography operations were performed at a flow rate of 0.64 mL/min. Elution profiles were compared and selected fractions were analysed by SDS-PAGE.

The glycoPEGylation enzymes were individually injected on Phenyl 650M to compare the elution profiles to Mixture 1 using the following condition: Buffer A: 25 mM Na phosphate, pH 7.0. Buffer B: 1 M Na Sulfate+buffer A, pH 7.0. Elution gradient: 100-0% B over 20 cv. The MBP-SBD-ST3Gal3, MBP-GnT1 and MBP-GalT1 all eluted in the same portion of the gradient. Mixture 1 elutes just prior to the enzymes. Although Mixture 1 and glycoPEGylation enzymes do not completely co-elute, Mixture 1 and the leading portion of the enzyme elution peaks seemed to overlap.

Optimization of the Sodium Sulfate Concentration Using Phenyl 650M Chromatography The concentration of sodium sulfate required to bind Mixture 1 bind Phenyl 650M was investigated. A Tricorn 5 column was packed with Phenyl 650M resin (1 mL, 0.5 cm×5 cm) as described above and attached to a Varian HPLC system. Each column was equilibrated with 5 column volumes (CV) of one of the buffers listed below. Product elution was monitored by absorbance at 280 nm.

Five separate injections of Mixture 1 (100 mcg, 250 mcL diluted to 1.25 mL with 1 mL Buffer B) were applied to the column using a 2 mL sample loop. Each chromatography used one of the following sodium sulfate concentrations in Buffer B: 1. 1.0 M sodium sulfate, 25 mM sodium phosphate, pH 7.5; 2. 0.8 M sodium sulfate, 25 mM sodium phosphate, pH 7.5; 3. 0.6 M sodium sulfate, 25 mM sodium phosphate, pH 7.5; 4. 0.4 M sodium sulfate, 25 mM sodium phosphate, pH 7.5; 5. 0.3 M sodium sulfate, 25 mM sodium phosphate, pH 7.5.

Any unbound material was washed from the column with 5 CV of Buffer B. EPO-(SA-PEG-10 kDa)$_3$ was eluted using a gradient of Buffer A (25 mM sodium phosphate, pH 7.0): 100-0% Buffer B over 20 CV (gradient change 5% Buffer B/CV), and then 0% Buffer B for 5 CV. Chromatography operations were performed at a flow rate of 0.64 mL/min (196 cm/hr). EPO-(SA-PEG-10 kDa)$_3$ peak fractions were stored at 4° C. until analysis by SDS-PAGE.

A minimum of 0.4 M sodium sulfate was required to bind Mixture 1 to the column. As expected the higher the sodium sulfate concentration the greater the retention time on the column. The same gradient slope (change in % B per minute) was maintained for all five purification runs. As the initial concentration of buffer B was reduced, the actual gradient (change in salt concentration/minute) became more shallow. This results in the increase in elution peak width seen as the buffer B start concentration decreases.

Optimization of the Sodium Sulfate Elution Gradient Using Phenyl 650S Chromatography A Tricorn 5 column was packed with Phenyl 650S resin (1 mL, 0.5 cm×5 cm) as described above and attached to an AKTA FPLC system. Product elution was monitored by absorbance at 280 nm. Three separate purifications were performed each using a different elution gradient. The columns from each experiment were equilibrated with 5 column volumes (CV) of Buffer B (25 mM sodium phosphate, 0.6 M sodium sulfate, pH 7.5).

Mixture 1 (100 mcg, 250 mcL) was diluted to 1.25 mL with 1 mL Buffer B and injected onto the column using a 2 mL sample loop. Any unbound material was washed from the column using 5 CV of Buffer B. The EPO-(SA-PEG-10 kDa)$_3$ product was eluted from the column using one of the following gradients using Buffer A (25 mM sodium phosphate, pH 7.5). Gradient 1: 100-0% Buffer B over 20 CV (gradient change 5% Buffer B/CV) followed by 0% Buffer B for 5 CV. Gradient 2: 100-0% Buffer B over 12 CV (gradient change 8.33% Buffer B/CV) followed by 0% Buffer B for 5 CV. Gradient 3: 100-60% Buffer B over 2 CV, hold for 1 CV, 60-20% Buffer B over 20 CV (gradient change 2% Buffer B/CV), 20-0% Buffer B over 2 CV and then 0% Buffer B for 5 CV. Chromatography operations were performed at a flow rate of 0.64 mL/min. Chromatography elution profiles were compared and selected fractions were analyzed by SDS PAGE. Out of the three gradient profiles tested, Gradient 3 provided the best separation of the EPO-PEG species.

Dynamic Range of the Process Parameters (Tosohaas Phenyl 650 S)
Effect of pH on the Separation of EPO-PEGs The effect of pH on the ability of the Phenyl 650S chromatography process to separate the PEG states of EPO-PEG was examined. A Tricorn 10 column was packed with 15.7 mL (1.0 cm id×20 cm) of Phenyl 650S. The column was equilibrated with 5 column volumes (CV) of buffer B (25 mM sodium phosphate, 0.6 M sodium sulfate, selected pH). In separate experiments, the process was repeated except the buffer pH was 6.5, 7.0, 7.5 or 8.0 in both Buffer A and B. The EPO-PEGX mixture (0.8 mg EPO protein conjugate; 1 mL) solution was adjusted to a sodium sulfate concentration of 0.6 M by addition of 0.4 mL of Buffer A (25 mM sodium phosphate, selected pH) and 0.6 mL of buffer (2 M sodium sulfate, 25 mM sodium phosphate, selected pH). This solution was then diluted with an equal volume of Buffer B and the entire sample (4 mL) was injected onto the column. The column was washed with 5 CV of Buffer B and the product eluted using a gradient using Buffer A. A gradient of 100-60% Buffer B over 2 CV, hold for 1 CV, 60-35% Buffer B over 13 CV, hold for 1 CV and then 0% Buffer B for 5 CV. The chromatography flow rate was 2.0 mL/min (150 cm/hr) and the column elution monitored by the absorbance at 280 nm. Fractions (1.6 mL) were collected in Nunc 96-well Microtiter plates. The chromatography elution profiles were compared and selected fractions were analyzed by SDS PAGE. Analysis of the product pool is summarized in Table 2, below:

Standard purification conditions (Buffer A: 25 mM sodium phosphate, pH 7.5. Buffer B: 25 mM sodium phosphate, 0.6 M sodium sulfate, pH 7.5 (with 0.05 mg EPO-(SA-PEG-10 kDa)$_{14}$/mL resin loaded) were compared to purification runs with buffer A and B prepared at pH 6.5, 7.0 and 8.0. The elution peaks (A280) are shifted slightly to the left and right of the standard elution condition. The X-axis of these A280 traces were shifted to overlay the peaks. Comparison of the X-axis shifted peaks shows similar peak traces with respect to the elution of EPO-(SA-PEG-10 kDa)$_2$, EPO-(SA-PEG-10 kDa)$_3$, and EPO-(SA-PEG-10 kDa)$_4$. This is especially true for pH 7.0, 7.5 and 8.0. The pH 6.5 run had a slightly lower peak max and a little less resolution was noted between the EPO-(SA-PEG-10 kDa)$_3$ and EPO-(SA-PEG-10 kDa)$_4$ peaks.

Table 2, above, compares EPO-(SA-PEG-10 kDa)$_3$ recovery, MBP-ELISA, RP-HPLC, and SEC analysis data. No significant difference was observed between the EPO-(SA-PEG-10 kDa)$_3$ purified within the 6.5 to 8.0 pH range. Recovery is between 60.3 and 66.7% (BCA analysis). MBP-ELISA indicates <0.077-0.085 mcg MBP/mg EPO-(SA-PEG-10 kDa)$_3$ remaining. RP-HPLC analysis show that the amount of EPO-(SA-PEG-10 kDa)$_2$ remaining in the EPO-(SA-PEG-10 kDa)$_3$ peak is between 2.5 and 4.9%. Integration of EPO-(SA-PEG-10 kDa)$_4$ is difficult at low levels but is detected by silver stain SDS-PAGE. No aggregation of EPO-(SA-PEG-10 kDa)$_3$ is detected by SEC analysis. SDS-PAGE analysis shows that the purity of each EPO-(SA-PEG-10 kDa)$_3$ pool is similar. However, the pH 6.5 purified material contained a higher amount of a approximate 50 kDa proteolyses band. A minor amount of this proteolysis product was also detected for the pH 7.0 purified material.

Effect of Sodium Phosphate Concentration on the Separation of EPO-PEGs

The effect of sodium phosphate concentration on the ability of the Phenyl 650S chromatography process to separate the PEG states of EPO-PEG was examined. A Tricorn 10 column was packed with 15.7 mL (1.0 cm id×20 cm) of Phenyl 650S. The column was equilibrated with 5 column volumes (CV) of buffer B (various concentrations of sodium phosphate, 0.6 M sodium sulfate, pH 7.5). In separate experiments, the process was repeated except the sodium phosphate concentration was 15, 25 or 50 mM in both Buffer A and B. The EPO-PEGX mixture (0.8 mg EPO protein; 1 mL) solution was adjusted to a sodium sulfate concentration of 0.6 M by addition of 0.4 mL of Buffer A (various concentrations of sodium phosphate, pH 7.5) and 0.6 mL of buffer (2 M sodium sulfate, various concentrations of sodium phosphate, pH 7.5). This solution was then diluted with an equal volume of Buffer

TABLE 2

Effect of pH on Separation and Recoveries of EPO-PEGs using Phenyl 650S[1]

| Buffer pH[2] | Step Yield[3] [%] | EPO-PEG$_3$[4] [%] | EPO-PEG$_2$[5] [%] | MBP[6] [mcg/mg EPO] | Aggregate[7] [%] |
|---|---|---|---|---|---|
| pH 6.5 | 60.3 | 95.1 | 4.9 | <0.085 | 0 |
| pH 7.0 | 66.7 | 96.3 | 3.7 | <0.077 | 0 |
| pH 7.5 | 61.6 | 97.5 | 2.5 | <0.083 | 0 |
| pH 8.0 | 65.4 | 96.6 | 3.4 | <0.078 | 0 |

[1]EPO-PEG (85.1% EPO-PEG$_3$ and 14.9% EPO-PEG$_2$ (Table 7).
[2]The pH of both, Buffer A and B.
[3]The step yield was calculated as the ratio of EPO-PEG protein recovered after HIC chromatography (combined fractions) versus the EPO-PEG injected onto the column
[4]The percent of EPO-(SA-PEG-10 kDa)$_3$ in the main product peak.
[5]The percent of EPO-(SA-PEG-10 kDa)$_2$ in the main product peak.
[6]The amount of MBP protein in the main product peak as determine by ELISA versus the amount of EPO-PEG protein.
[7]The amount of aggregate EPO-PEG in the product peak observed by SEC.

B and the entire sample (4 mL) was injected onto the column. The column was washed with 5 CV of Buffer B and the product eluted using a gradient using Buffer A. A gradient of 100-60% Buffer B over 2 CV, hold for 1 CV, 60-35% Buffer B over 13 CV, hold for 1 CV and then 0% Buffer B for 5 CV. The chromatography flow rate was 2.0 mL/min (150 cm/hr) and the column elution monitored by the absorbance at 280 nm. The chromatography elution profiles were compared and selected fractions were analyzed by SDS PAGE. The pooled fractions of the major product peak were analyzed. Results are summarized in Table 3, below:

low levels but is detected by silver stain SDS-PAGE. SDS-PAGE analysis showed that the purity of each EPO-(SA-PEG-10 kDa)$_3$ pool is comparable as determined by colloidal blue and silver stained gels. No notable differences in purity were detected by SDS-PAGE.

Effect of Sodium Sulfate Concentration on the Separation of EPO-PEGs

The robustness and the capability of the Phenyl 650S chromatography step to separate the PEG states of EPO-PEG was examined with respect to variations in the Na sulfate concentrations in buffer B. A Tricorn 10 column was packed with

TABLE 3

Effect of Sodium Phosphate Concentration on Separation and Recovery of EPO-PEGs using Phenyl 650S.[1]

| Sodium Phosphate Concentration[2] | Step Yield[3] [%] | EPO-PEG$_3$[4] [%] | EPO-PEG$_2$[5] [%] | MBP[6] [mcg/mg EPO] | Aggregate[7] [%] |
|---|---|---|---|---|---|
| 15 mM | 61.5 | 95.5 | 4.5 | <0.083 | 0 |
| 25 mM | 61.9 | 96.3 | 3.7 | <0.085 | 0.22 |
| 50 mM | 60.2 | 95.8 | 4.2 | <0.085 | 0.34 |

[1]EPO-PEG (85.1% EPO-PEG$_3$ and 14.9% EPO-PEG$_2$ (Table 7).
[2]The sodium phosphate concentration of both, Buffer A and B.
[3]The step yield was calculated as the ratio of EPO-PEG protein recovered after HIC chromatography (combined fractions) versus the amount EPO-PEG injected onto the column
[4]The percent of EPO-(SA-PEG-10 kDa)$_3$ in the main product peak.
[5]The percent of EPO-(SA-PEG-10 kDa)$_2$ in the main product peak.
[6]The amount of MBP protein in the main product peak as determine by ELISA assay versus the amount of EPO-PEG protein.
[7]The amount of aggregate EPO-PEG in the product peak observed by SEC.

Standard purification conditions (Buffer A: 25 mM sodium phosphate, pH 7.5. Buffer B: 25 mM sodium phosphate, 0.6M sodium sulfate, pH 7.5 (0.05 mg EPO-(SA-PEG-10 kDa)$_{14}$/mL resin loaded) were compared to purification runs with buffer A and B prepared with 15 and 50 mM sodium phosphate. Resulting A280 elution profiles were compared. The 15 mM Na phosphate eluted material elutes earliest, followed by the 25 mM Na phosphate and finally 50 mM Na phosphate. The shift in elution profile is due to the relative changes in buffer conductivity (see table 3). The X-axis of these A280 traces were shifted to overlay the peaks. Comparison of the X-axis shifted peaks shows similar peak traces with respect to the elution of EPO-(SA-PEG-10 kDa)$_2$, EPO-(SA-PEG-10 kDa)$_3$, and EPO-(SA-PEG-10 kDa)$_4$.

Table 3 compares EPO-(SA-PEG-10 kDa)$_3$ recovery, MBP-ELISA, RP-HPLC, and SEC analysis data. No significant difference was observed between the EPO-(SA-PEG-10 kDa)$_3$ purified within this 15 to 50 mM sodium phosphate concentration range. Recovery is between 60.2 and 61.9%. MBP-ELISA indicates <0.083-0.085 mcg MBP/mg EPO-(SA-PEG-10 kDa)$_3$ remaining. RP-HPLC analysis showed that the amount of EPO-(SA-PEG-10 kDa)$_2$ remaining in the EPO-(SA-PEG-10 kDa)$_3$ peak is between 3.7 and 4.5%. Integration of the EPO-(SA-PEG-10 kDa)$_4$ peak was difficult at 15.7 mL (1.0 cm id×20 cm) of Phenyl 650S. The column was equilibrated with 5 column volumes (CV) of buffer B (25 mM sodium phosphate, various concentrations of sodium sulfate, pH 7.5). In separate experiments, the process was repeated except the buffer sodium sulfate concentrations of 0.5, 0.6 and 0.7 M of Buffer B were varied. The EPO-PEGX mixture (0.8 mg EPO protein; 1 mL) solution was adjusted to a sodium sulfate concentration by the addition of 0.3-0.5 mL of Buffer A (25 mM sodium phosphate, pH 7.5) and 0.5-0.7 mL of buffer (2 M sodium sulfate, 25 mM sodium phosphate, pH 7.5) depending on the sodium sulfate concentration used in the experiment. This solution was then diluted with an equal volume of Buffer B and the entire sample (4 mL) was injected onto the column. The column was washed with 5 CV of Buffer B and the product eluted using a gradient using Buffer A. A gradient of 100-60% Buffer B over 2 CV, hold for 1 CV, 60-35% Buffer B over 13 CV, hold for 1 CV and then 0% Buffer B for 5 CV. The chromatography flow rate was 2.0 mL/min (150 cm/hr) and the column elution monitored by the absorbance at 280 nm. The chromatography elution profiles were compared and selected fraction were analyzed by SDS PAGE. Analysis of the pooled fractions corresponding to the main product peak is summarized in Table 4, below:

TABLE 4

Effect of Sodium Sulfate Concentration on Separation and Recovery of EPO-PEGs using Phenyl 650S.[1]

| Sodium Sulfate Concentration[2] | Step Yield[3] [%] | EPO-PEG$_3$[4] [%] | EPO-PEG$_2$[5] [%] | MBP[6] [mcg/mg EPO] | Aggregate[7] [%] |
|---|---|---|---|---|---|
| 0.5 M | 61.5 | 96.6 | 3.4 | <0.083 | 0 |
| 0.6 M | 64.0 | 95.4 | 4.6 | <0.04 | 0.22 |
| 0.7 M | 64.2 | 95.4 | 4.6 | <0.04 | 0.34 |

[1]EPO-PEG (85.1% EPO-PEG$_3$ and 14.9% EPO-PEG$_2$ (Table 7).
[2]The sodium sulfate concentration of Buffer B.

TABLE 4-continued

Effect of Sodium Sulfate Concentration on Separation and Recovery of EPO-PEGs using Phenyl 650S.[1]

| Sodium Sulfate Concentration[2] | Step Yield[3] [%] | EPO-PEG$_3$[4] [%] | EPO-PEG$_2$[5] [%] | MBP[6] [mcg/mg EPO] | Aggregate[7] [%] |
|---|---|---|---|---|---|

[3]The step yield was calculated as the ratio of EPO-PEG protein recovered after HIC chromatography (combined fractions) versus the amount of EPO-PEG injected onto the column.
[4]The percent of EPO-(SA-PEG-10 kDa)$_3$ in the main product peak.
[5]The percent of EPO-(SA-PEG-10 kDa)$_2$ in the main product peak.
[6]The amount of MBP protein in the main product peak as determine by the ELISA versus the amount of EPO-PEG protein.
[7]The amount of aggregate EPO-PEG in the product peak observed by SEC.

Standard purification conditions (Buffer A: 25 mM sodium phosphate, pH 7.5. Buffer B: 25 mM sodium phosphate, 0.6M sodium sulfate, pH 7.5. With 0.05 mg EPO-(SA-PEG-10 kDa)$_{1-4}$/mL resin loaded) were compared to purification runs with buffer B prepared with 0.5 and 0.7 M sodium sulfate. Elution profiles (A280) were compared. The run with buffer B containing 0.5 M Na sulfate elutes earliest, followed by the 0.6 M Na sulfate and finally 0.7 M Na sulfate run. The X-axis of these A280 traces were shifted to overlay the peaks. Comparison of the X-axis shifted peaks shows similar peak traces with respect to the elution of EPO-(SA-PEG-10 kDa)$_2$, EPO-(SA-PEG-10 kDa)$_3$, and EPO-(SA-PEG-10 kDa)$_4$. A slight difference in peak width was noticed when comparing the elution peak profiles. Buffer B containing 0.7 M Na sulfate shows the sharpest peak shape, followed by the 0.6 M Na sulfate run and then 0.5 M Na sulfate run. The gradient programmed on the chromatography system was kept constant for each run. However, the increase or decrease of sodium sulfate in buffer B will decrease or increase the actual slope of the elution gradient respectively.

Table 4 compares EPO-(SA-PEG-10 kDa)$_3$ recovery, MBP-ELISA, RP-HPLC, and SEC analysis data. No significant difference was noted between the EPO-(SA-PEG-10 kDa)$_3$ purified within the 0.5 to 0.7 M sodium sulfate concentration range. Recovery is between 61.5 and 64.2%. ELISA indicates <0.04-0.083 mcg MBP/mg EPO-(SA-PEG-10 kDa)$_3$ remaining. RP-HPLC analysis showed that the amount of EPO-(SA-PEG-10 kDa)$_2$ remaining in the EPO-(SA-PEG-10 kDa)$_3$ peak is between 3.4 and 4.6%. Integration of the EPO-(SA-PEG-10 kDa)$_4$ peak was difficult at low levels but the glycoform was detected by silver stain SDS-PAGE. SDS-PAGE analysis showed that the purity of each EPO-(SA-PEG-10 kDa)$_3$ pool is similar as determined by colloidal blue as well as silver stained gels.

Column Capacity (Phenyl 650S) for EPO-PEG.

The resin capacity for EPO-PEG and the ability of the Phenyl 650S chromatography process to separate the PEG states of EPO-PEG was examined. A Tricorn 10 column was packed with 15.7 mL (1.0 cm id×20 cm) of Phenyl 650S. The column was equilibrated with 5 column volumes (CV) of buffer B (25 mM sodium phosphate, 0.6 M sodium sulfate, pH 7.5). In separate experiments, the amount of EPO-PEG used in the process was varied (0.05, 0.1, 0.2, 0.5 mg EPO-(SA-PEG-10 kDa)$_{1-4}$ protein/mL resin). The EPO-PEG$_x$ mixture was adjusted to a sodium sulfate concentration of 0.6 M and a final volume of 4 mL. This solution was injected onto the column. The column was washed with 5 CV of Buffer B and the product eluted using a gradient using Buffer A. A gradient of 100-60% Buffer B over 2 CV, hold for 1 CV, 60-35% Buffer B over 13 CV, hold for 1 CV and then 0% Buffer B for 5 CV. The chromatography flow rate was 2.0 mL/min (150 cm/hr) and the column elution monitored by the absorbance at 280 nm. The chromatography elution profiles were compared. Fractions were pooled and analyzed by SDS-PAGE. Analysis of the main product peak is summarized in Table 5, below:

TABLE 5

Effect of Phenyl 650S Column Capacity on Separation and Recovery of EPO-PEGs.[1]

| Injected Amount of EPO-PEG[2] | Step Yield[3] [%] | EPO-PEG$_3$[4] [%] | EPO-PEG$_2$[5] [%] | MBP[6] [mcg/mg EPO] | Aggregate[7] [%] |
|---|---|---|---|---|---|
| 0.05 mg/mL resin | 61.9 | 96.3 | 3.7 | 0.085 | 0.22 |
| 0.1 mg/mL resin | 67.6 | 95.8 | 4.2 | <0.024 | 0 |
| 0.2 mg/mL resin | 70.2 | 94.9 | 5.1 | <0.024 | 0 |
| 0.5 mg/mL resin | 70.2 | 92.5 | 7.5 | <0.019 | 0 |

[1]EPO-PEG (85.1% EPO-PEG$_3$ and 14.9% EPO-PEG$_2$ (Table 7).
[2]The ratio of EPO-PEG protein injected per mL of HIC resin packed in the column (mg EPO/mL resin).
[3]The step yield was calculated as the ratio of total EPO-PEG conjugate recovered after HIC chromatography versus the amount of EPO-PEG injected onto the column.
[4]The percent of EPO-(SA-PEG-10 kDa)$_3$ in the main product peak.
[5]The percent of EPO-(SA-PEG-10 kDa)$_2$ in the main product peak.
[6]The amount of MBP-protein contained in the main product peak as determine by ELISA assay versus the amount of EPO-PEG protein.
[7]The amount of aggregate EPO-PEG in the product peak observed by SEC.

The robustness of the Phenyl 650S chromatography step was tested with respect to variations in the quantity of EPO-(SA-PEG-10 kDa)$_{1-4}$ loaded per mL Phenyl 650S resin. Standard purification conditions (Buffer A: 25 mM sodium phosphate, pH 7.5. Buffer B: 25 mM sodium phosphate, 0.6M sodium sulfate, pH 7.5 (0.05 mg EPO-(SA-PEG-10 kDa)$_{1-4}$/mL resin loaded) were compared to purification runs where the column was loaded with 0.1, 0.2 and 0.5 mg EPO-(SA-PEG-10 kDa)$_{1-4}$/mL resin. Comparison of the resulting elution profiles (A280) shows a decrease in resolution between the EPO-(SA-PEG-10 kDa)$_2$ and EPO-(SA-PEG-10 kDa)$_3$ peaks as the amount of protein loaded onto the column is increased. RP-HPLC analysis was used to compare the amount of EPO-(SA-PEG-10 kDa)$_2$ remaining in the EPO-(SA-PEG-10 kDa)$_3$ pooled peak. Table 5 compares EPO-(SA-PEG-10 kDa)$_3$ recovery, MBP-ELISA, RP-HPLC, and SEC analysis data. No significant difference was noted between the EPO-(SA-PEG-10 kDa)$_3$ purified within the investigated column loading range. Recovery was between 61.9 and 70.2% (BCA analysis). As the quantity of material loaded onto the column is increased the recovery increased. However, this increase is also correlated with an increase in the amount of EPO-(SA-PEG-10 kDa)$_2$ remaining. MBP-ELISA indicates <0.019-0.085 mcg MBP/mg EPO-(SA-PEG-10 kDa)$_3$ remaining. RP-HPLC analysis resulted in a % EPO-(SA-PEG-10 kDa)$_3$ to % EPO-(SA-PEG-10 kDa)$_2$ ratio of 96.3:3.7, 95.8:4.2, 94.9:5.1, 92.5:7.5 for the 0.05 mg, 0.1 mg, 0.2 mg and 0.5 mg EPO-(SA-PEG-10 kDa)$_{14}$/mL resin loads, respectively.

Increasing the quantity of the protein loaded onto the column increases the amount of EPO-(SA-PEG-10 kDa)$_2$ in the EPO-(SA-PEG-10 kDa)$_3$ peak since the peaks were pooled in the same manner. Integration of the EPO-(SA-PEG-10 kDa)$_4$ was difficult at low levels but the glycoform was detected by silver stain SDS-PAGE. No aggregation of EPO-(SA-PEG-10 kDa)$_3$ was detected by SEC analysis. Minor aggregation (0.22%) of EPO-(SA-PEG-10 kDa)$_3$ was detected by SEC analysis in the 0.05 mg EPO-(SA-PEG-10 kDa)$_{1-4}$/mL resin load (this is the same sample described in the sodium phosphate buffer concentration experiment). SDS-PAGE analysis showed that the purity of each EPO-(SA-PEG-10 kDa)$_3$ pool is similar when determined by colloidal blue and silver stained gels.

Comparison of Phenyl 650S and 650M Resins

The ability of Phenyl 650M and Phenyl 650S chromatography resins to separate the PEG states of EPO-PEG was examined. A Tricorn 10 column was packed with 15.7 mL (1.0 cm id×20 cm) of either Phenyl 650S or Phenyl 650M. Each column was equilibrated with 5 column volumes (CV) of buffer B (25 mM sodium phosphate, 0.6 M sodium sulfate, pH 7.5). The EPO-PEG$_x$ (0.8 mg EPO protein; 1 mL) solution was adjusted to a sodium sulfate concentration of 0.6 M by the addition of 0.4 mL of Buffer A (25 mM sodium phosphate, pH 7.5) and 0.6 mL of buffer (2 M sodium sulfate, 25 mM sodium phosphate, pH 7.5). This solution was then diluted with an equal volume of Buffer B and the entire sample (4 mL) was injected onto the column. The column was washed with 5 CV of Buffer B and the product eluted using a gradient using Buffer A. A gradient of 100-60% Buffer B over 2 CV, hold for 1 CV, 60-35% Buffer B over 13 CV, hold for 1 CV and then 0% Buffer B for 5 CV. The chromatography flow rate was 2.0 mL/min (150 cm/hr) and the column elution monitored by the absorbance at 280 nm. The chromatography elution profiles were compared and selected fractions were analyzed by SDS PAGE. Analysis of the main product peak is summarized in Table 6, below:

TABLE 6

Comparison of Phenyl 650S and 650M Resins and the Effect on Separation and Recovery of EPO-PEGs.[1]

| Resin[2] | Step Yield[3] [%] | EPO-PEG$_3$[4] [%] | EPO-PEG$_2$[5] [%] | MBP[6] [mcg/mg EPO] | Aggregate[7] [%] |
|---|---|---|---|---|---|
| Phenyl 650S | 61.6 | 97.5 | 2.5 | 0.083 | 0 |
| Phenyl 650M | 65.1 | 93.6 | 6.4 | | 0 |

[1]EPO-PEG (85.1% EPO-PEG$_3$ and 14.9% EPO-PEG$_2$ (Table 7).
[2]Tosohaas Phenyl chromatography resins.
[3]The step yield was calculated as the ratio of EPO-PEG protein recovered after HIC chromatography (combined fractions) versus the amount of EPO-PEG injected onto the column.
[4]The percent of EPO-(SA-PEG-10 kDa)$_3$ in the main product peak.
[5]The percent of EPO-(SA-PEG-10 kDa)$_2$ in the main product peak.
[6]The amount of MBP protein contained in the main product peak as determine by ELISA versus the amount of EPO-PEG protein.
[7]The amount of aggregate EPO-PEG in the product peak observed by SEC.

The Phenyl 650S (35 micron bead size) chromatography step was compared with Phenyl 650M (65 micron bead size) using standard purification conditions (Buffer A: 25 mM sodium phosphate, pH 7.5. Buffer B: 25 mM sodium phosphate, 0.6M sodium sulfate, pH 7.5 (0.05 mg EPO-(SA-PEG-10 kDa)$_{14}$/mL resin loaded). Comparison of the resulting elution profiles showed that Phenyl 650S has a better resolution between EPO-(SA-PEG-10 kDa)$_2$ and EPO-(SA-PEG-10 kDa)$_3$. Comparison of the respective EPO-(SA-PEG-10 kDa)$_3$ peak pools by SDS-PAGE showed similar purity except that the Phenyl 650S purified material appears to have less EPO-(SA-PEG-10 kDa)$_4$. Analysis by RP-HPLC showed a EPO-(SA-PEG-10 kDa)$_3$ to EPO-(SA-PEG-10 kDa)$_2$ ratio of 96.3:3.7 for Phenyl 650S and a ratio of 93.6:6.4 for the Phenyl 650M purification.

The total system and column pressure measurements show the average pressure throughout the Phenyl 650M purification was approximately 0.12 mPa, while the Phenyl 650S pressure was approximately 0.29 mPa.

Phenyl 650S vs Phenyl Sepharose HP Chromatography.

EPO-(SA-PEG-10 kDa)$_3$ purification using Phenyl Sepharose HP (34 micron beads size) was performed using standard purification conditions (Buffer A: 25 mM sodium phosphate, pH 7.5. Buffer B: 25 mM sodium phosphate, 0.6M sodium sulfate, pH 7.5, with 0.05 mg EPO-(SA-PEG-10 kDa)$_{1-4}$/mL resin loaded. The elution profile showed no actual resolution between EPO-(SA-PEG-10 kDa)$_1$, EPO-(SA-PEG-10 kDa)$_2$, EPO-(SA-PEG-10 kDa)$_3$ and EPO-(SA-PEG-10 kDa)$_4$ (chromatogram not shown). Since there was no resolution between the various PEG states no analysis was performed on the eluted material.

Example 2

Large-Scale Purification of GlycoPEGylated EPO Using Hydrophobic Interaction Chromatography In order to further purify glycoPEGylated EPO from a glycoPEGylation reaction mixture, and to separate the tri-functionalized EPO species [EPO-(SA-PEG-10 kDa)$_3$] from other PEGylated species (e.g., mono-, di- and tetra-PEGylated EPO species), the mixture (e.g., flowthrough from an anion chromatography medium) is subjected to hydrophobic interaction chromatography (HIC). An exemplary HIC procedure is outlined below: An XK26 column was packed with Phenyl 650S resin (106 mL, 2.6 cm×20 cm) and attached to an AKTA Explorer 100 system. Product elution was monitored by absorbance at 214, 254 and 280 nm. The column was equilibrated with 5 column volumes (CV) of Buffer B (25 mM sodium phosphate, 0.6 M sodium sulfate, pH 7.5)

The solution of Sartobind Q purified EPO-(SA-PEG-10 kDa)$_{1-4}$ (62 mL, pH 6.94, 2.59 mS/cm) was adjusted to 0.6 M sodium sulfate by dilution with 62 mL of 1.2 M of buffer (1.2 M sodium sulfate, 25 mM sodium phosphate, pH 7.5). This solution (124 mL) was injected on the column. The ratio of EPO-PEG to resin upon injection onto the column was 0.18 mg EPO protein per mL of resin in the column. Any unbound material was washed from the column using 5 CV of Buffer B (25 mM sodium phosphate, 0.6 M sodium sulfate, pH 7.5). The EPO-(SA-PEG-10 kDa)$_3$ was eluted from the column using the following gradient elution procedure using Buffer A (25 mM sodium phosphate, pH 7.5). Gradient: 100-60% Buffer B over 2 CV, hold for 1 CV, 60-35% Buffer B over 13 CV (gradient change 1.92% Buffer B/CV), hold 1 CV and then 0% Buffer B for 5 CV. The equilibration, load and wash steps were performed at a flow rate of 8 mL/min (90 cm/hr).

Figure 2A:
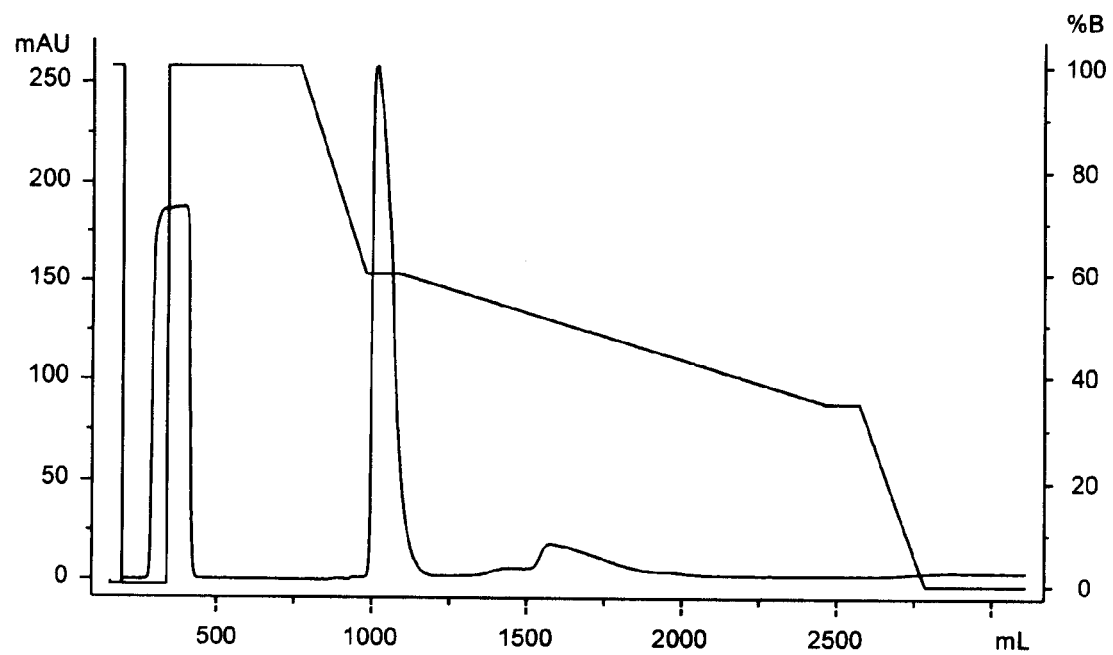
FIG. 2A is an exemplary chromatogram showing the resolution of tri-PEGylated EPO from mono-, di-, tri- and tetra-PEGylated EPO glycoforms using hydrophobic interaction chromatography with Phenyl 650S as the separation medium.
Figure 2B:
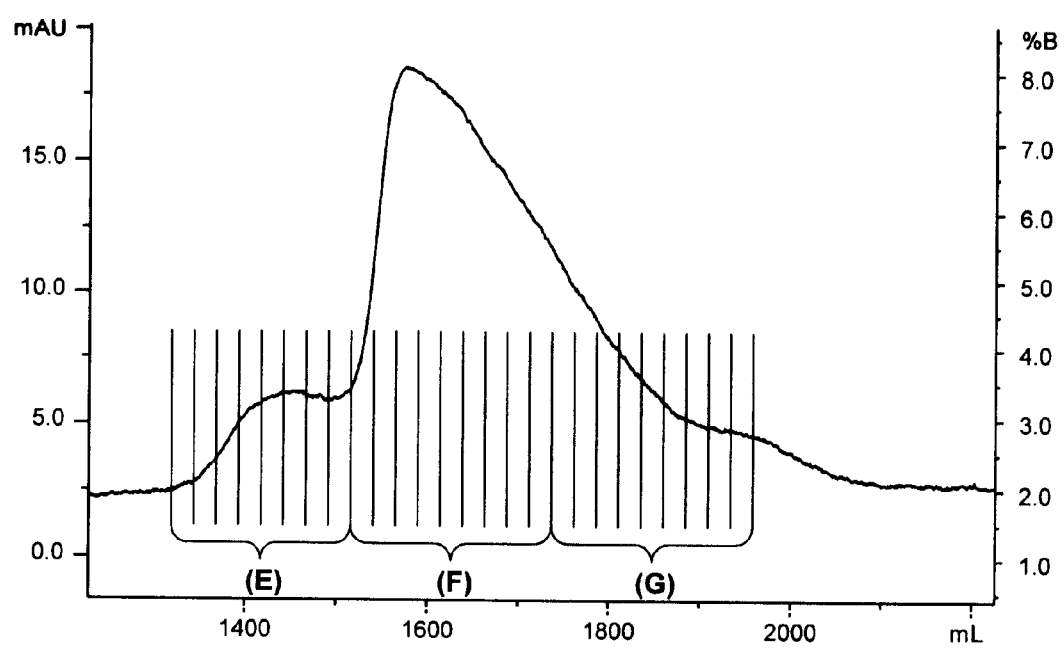
FIG. 2B is an expanded view of the EPO-(SA-PEG-10 kDa)$_2$, EPO-(SA-PEG-10 kDa)$_3$ and EPO-(SA-PEG-10 kDa)$_4$ elution peaks of the chromatogram in FIG. 2A. The letters (E), (F) and (G) indicate fractions that were pooled, wherein (F) indicates the elution of EPO-(SA-PEG-10 kDa)$_3$.

Flow through and wash fractions were collected in a 1 L Nalgene container and individual elution fractions (12 mL) were collected in 14 mL Falcon tubes. The elution profile and fraction indicators are shown in FIGS. 2A and 2B. Fractions were combined, the buffer was exchanged and the pool was concentrated using Pellicon-2 XL 50 cm². The pooled fractions containing the EPO-(SA-PEG-10 kDa)$_3$ (pool F) were analyzed for protein content (BCA, UV), identity (SDS-PAGE), glycosyltransferases (MBP-ELISA), purity and EPO-PEG forms (RP-HPLC), aggregation and purity (SEC) and endotoxin. Results are summarized in Table 7, below:

in the load material. Concentration and diafiltration into 10 mM sodium acetate, 150 mM NaCl, pH 5.4 using a Pellicon-2 XL 50 cm² yielded a 95% recovery.

Example 3

Preparation and Isolation of EPO-(SA-PEG-10 kDa)$_3$ from a GlycoPEGylation Reaction Mixture This example summarizes the results obtained with a 3 chromatography step (and two ultrafiltration/diafilatration (UF/DF) steps) purification process for the isolation of baculoviral derived, glycoPEGylated human erythropoietin EPO-(SA-PEG-10 kDa)$_3$ (see, description of EPO-PEG conjugates in Example 1, above) at a 20 mg scale. Overall process efficiency and product quality were assessed.

The purification process (see e.g., FIG. 1) began with a Sartobind Q membrane used in a negative binding mode which allowed the PEG-EPO conjugates to flow through while capturing glycoPEGylation enzymes, such as MBP-GnT1, MBP-GalT1, MBP-SBD-ST3Gal3 and other enzyme contaminants. The various PEG species generated in the glycoPEGylation reaction were then fractionated using HIC on a Phenyl 650S resin (also compare Example 1), which enriched the EPO-(SA-PEG-10 kDa)$_3$ to a concentration of >96% (step yield approximately 75%). Tangential flow filtration (TFF, ultrafiltration/diafiltration) employing regenerated cellulose (10 kDa MWCO) membranes, was used to concentrate and reduce the conductivity of the HIC elution pool. Cation exchange chromatography using Source 15S was then

TABLE 7

Results from the Large Scale Purification of EPO-PEG using Phenyl 650S Chromatography

| Process Step | Amount Injected[2] | Step Yield[3] [%[ | EPO-PEG$_3$[4] [%[ | EPO-PEG$_2$[5] [%[ | MBP[6] [mcg/mg EPO] |
|---|---|---|---|---|---|
| Sartobind Q FT[8] | NA[9] | 94.2 | 86.6 | 13.4 | 0.69 |
| EPO-PEG$_3$ Phenyl 650S Fraction[10] | 18 mg | 79.3 | 96.4 | 3.6 | <0.0196 |

[2]Amount of EPO protein determined by A280.

[3]The step yield was calculated as the ratio of EPO-PEG protein recovered after HIC chromatography (combined fractions) versus the EPO-PEG injected onto the column.

[4]The percent of EPO-(SA-PEG-10 kDa)$_3$ in the main product peak.

[5]The percent of EPO-(SA-PEG-10 kDa)$_2$ in the main product peak.

[6]The amount of MBP protein contained in the main product peak as determine by ELISA versus the amount of EPO-PEG protein.

[7]The amount of aggregate EPO-PEG in the product peak observed by SEC.

[8]EPO-PEG filtered through a Sartobind Q resin.

[9]Not available.

[10]Combined fractions of the main product peak after chromatography using optimized conditions on a Phenyl 650S resin.

Phenyl 650S Chromatography was scaled up from a 0.8 mg EPO-(SA-PEG-10 kDa)$_{1-4}$ load (15.7 mL column) to a 22.4 mg load (106 mL column). The standard conditions were used except the amount of material loaded on the column was increased from 0.05 to 0.2 mg EPO-(SA-PEG-10 kDa)$_{14}$/mL resin. The EPO-(SA-PEG-10 kDa)$_3$ peak was pooled as shown in FIG. 2B resulting in a 408 mL peak pool (3.85 CV). Prior to concentration 16.1 mg EPO-(SA-PEG-10 kDa)$_3$ was recovered (72%) with 5.7% EPO-(SA-PEG-10 kDa)$_2$ remaining from the original 14.9% EPO-(SA-PEG-10 kDa)$_2$ employed to remove remaining host cell proteins and to further enrich the EPO-(SA-PEG-10 kDa)$_3$ to a concentration of greater than 97% (80% step yield). Finally, TFF with regenerated cellulose, 10 kDa MWCO membranes was used to concentrate and change the buffer for storage of the bulk product. 6.7 mg of purified EPO-PEG conjugate was obtained, which corresponds to an overall yield of 56% for the purification process (after correction for sampling and small-scale side experiments). Process parameters are summarized in Table 8, below:

TABLE 8

Summary of Process Steps and Analytical Results

| Process Step | Total Protein Load | Total Protein Recovery | Step Recovery | RP-HPLC (% Tri/Di PEG) | mcg MBP/mg PEG-EPO |
|---|---|---|---|---|---|
| PEGylation Reaction Mixture | ~25 mg[1] | 21.7 mg[2] | 100% | 83/17 | 138.58 |
| Sartobind Q | 20.9 mg[2] | 19.7 mg[2] | 94% | 86.6/13.4[3] | 0.69 |
| Phenyl 650S | 15.25 mg[2] | 11.1 mg[4] | 73%[5] | — | — |
| TFF | 11.02 mg[4] | 12.1 mg[4] | 110% | 96.4/3.6 | <0.0196 |
| Source 15S | 10 mg[4] | 7.93 mg[3] | 79% | 97.1/2.9 | — |
| TFF | 7.89 mg[4] | 7.75 mg[4] | 98% | — | — |
| 0.2 um syringe Filtration[6] | 6.95 mg[4] | 6.69 mg[4] | 96% | — | <0.0196 |
| Total Process Recovery | | | 56% | | |

The overall process pool was reduced by sampling and/or for side experiments at each step.
[1]Protein concentration was determined by BCA relative to BSA standard prior to initial buffer exchange.
[2]Protein concentration determined by RP-HPLC.
[3]GlycoPEGylation reaction continued slightly after the original RP-HPLC analysis while the sample was awaiting purification of Sartoind Q (<1 hour)
[4]Protein concentration determined by A280 (extinction coefficient 1.24)
[5]Actual protein concentration is too low for accurate measurement by A280 (0.025 mg/mL). Two step recovery (Phenyl 650S + TFF) = 79%
[6]A small percentage (2.2%) of the final filtration volume was held up in the sterile filter.

At each chromatography step the PEG-EPO product pool was analyzed by SDS-PAGE, RP-HPLC for PEG-state and MBP ELISA to track the removal of enzyme related contaminants. The resulting EPO-(SA-PEG-10 kDa)$_3$ product was subjected to available drug product release tests. The purity was found to be greater than 99% by HPLC (combined glycoforms). The concentration of EPO-(SA-PEG-10 kDa)$_3$ in the final composition was 96.9%. The concentration of EPO-(SA-PEG-10 kDa)$_2$ was 2.5% and the concentration of EPO-(SA-PEG-10 kDa)$_4$ was 0.6%. Other EPO-PEG glycoforms were not detected in the final composition. There was less than 1% aggregate by SEC.

GlycoPEGylation Reaction

Human EPO intermediate protein (produced by Baculovirus fermentation and purified) was stored frozen in 20 mM HEPES, pH 7.5 at −20° C. at a concentration of 1.29 mg/mL as determined by BCA assay. MBP-GnTa1 was stored frozen in 50 mM Tris, pH 7.0, 138 mM NaCl at −20° C. The reported activity assay value of 0.5 U/mL was used. RP-HPLC analysis determined the protein concentration to be 0.3 mg/mL. MBP-GalT1 was stored frozen in 20 mM HEPES, pH 7.5, 200 mM NaCl at −20° C. The activity was reported to be 15 U/mL, with a protein concentration of 1.0 mg/mL as determined by RP-HPLC. MBP-SBD-ST3Gal3 was stored frozen in 20 mM HEPES, pH 7.0 at −20° C. The reported activity was 2.05 U/mL and the protein concentration was measured to be 1.06 mg/mL by BCA assay. UDP-GlcNAc and UDP-Gal were prepared as 60 mg/mL stock solutions in 100 mM HEPES, pH 7.0, 20 mM NaCl, 0.02% NaN$_3$ immediately prior to use. CMP-SA-PEG-10 kDa was prepared as a 200 mg/mL stock solution in 100 mM HEPES, pH 7.0, 20 mM NaCl, 0.02% NaN$_3$ immediately prior to use.

Preparation and Analysis of 25 mg EPO-(SA-PEG-10 kDa)$_3$ Reaction

Figure 4A:
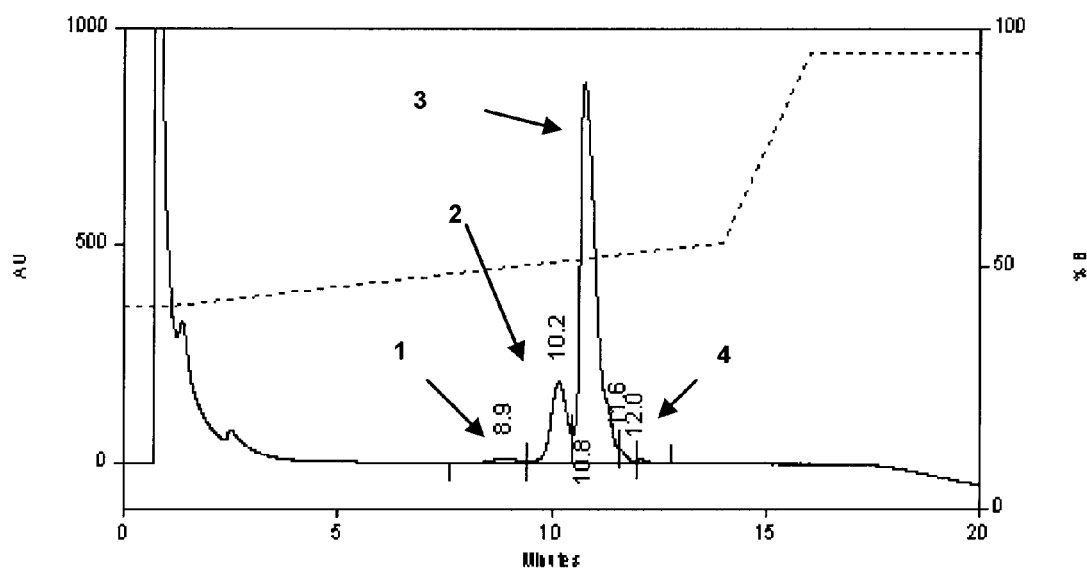
FIG. 4A is a reverse phase (RP)HPLC chromatogram of an exemplary glycoPEGylation reaction mixture containing EPO-(SA-PEG-10 kDa)$_{1-4}$ performed at a 25 mg scale. A Zorbax 300SB-C3 (150×2.1 mm, 5 micron) column was used in the analysis. The following eluants were used: 0.1% TFA in water (Buffer A) and 0.09% TFA in CAN (Buffer B). The gradient was 42-55% B in 14 min followed by 55-95% B in 2 min. The flow rate was 0.6 mL/min. Absorption was measured at 214 nm. The numbered peaks represent: (1) Mono-PEG-EPO=EPO-(SA-PEG-10 kDa)$_1$; (2) di-PEG-EPO=EPO-(SA-PEG-10 kDa)$_2$; (3) tri-PEG-EPO=EPO-(SA-PEG-10 kDa)$_3$ and (4) tetra-PEG-EPO=EPO-(SA-PEG-110 kDa)$_4$.
Figure 4B:
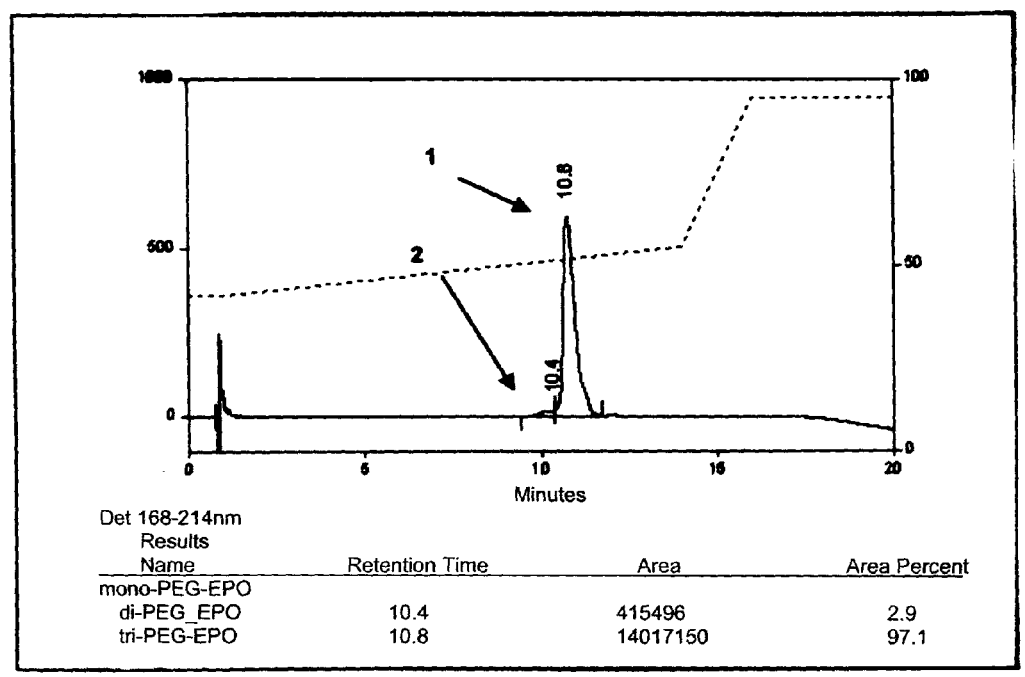
FIG. 4B is a reverse phase (RP)HPLC chromatogram of an exemplary composition of the invention containing purified EPO-(SA-PEG-10 kDa)$_3$ as the major component, the composition obtained using a method of the invention. The numbered peaks represent: (1) tri-PEG-EPO=EPO-(SA-PEG-10 kDa)$_3$ and (2) di-PEG-EPO-EPO-(SA-PEG-10 kDa)$_2$.

EPO intermediate protein (25 mg, 19.4 mL, 1.25 micromoles by BCA assay) was concentrated to a volume of 1.0 mL in a Centricon Plus-20 centrifugal filter (5 kDa MWCO) and then diluted with 15 mL of 100 mM HEPES, pH 7.0, 20 mM NaCl, 0.02% NaN$_3$. The EPO solution was concentrated to 0.94 mL (26.7 mg/mL). MBP-SBD-ST3Gal3 (3.05 mL, 6.25 U) was diluted with 13 mL of 100 mM HEPES, pH 7.0, 20 mM NaCl, 0.02% NaN$_3$ in another Centricon Plus-20 centrifugal filter (5 kDa MWCO) and was concentrated to 0.51 mL (12.3 U/mL). The UDP-GlcNAc (25 micromoles, 0.27 mL) and UDP-Gal (25 micromoles, 0.25 mL) stock solutions (both at 60 mg/mL in 100 mM HEPES, pH 7.0, 20 mM NaCl, 0.02% NaN$_3$), MBP-GnT1 (0.5 mL, 0.25 U), MBP-GalT1 (0.33 mL, 5 U), the concentrated MBP-SBD-ST3Gal3 (0.51 mL of 12.3 U/mL, 6.25 U, from above), CMP-SA-PEG-10 kDa (25 micromole, 1.25 mL of 200 mg/mL solution in 100 mM HEPES, pH 7.0, 20 mM NaCl, 0.02% NaN$_3$) and MnCl$_2$ (5 mM, 0.104 mL of 200 mM solution in water) were combined. Additional 100 mM HEPES, pH 7.0, 20 mM NaCl, 0.02% NaN$_3$ buffer was added (1.0 mL) to bring the total volume to 4.17 mL. The reaction was incubated at 32° C. for 2 hrs without shaking. The conversion yield of EPO-(SA-PEG-10 kDa)$_3$ was determined by SDS-PAGE and C3 RP-HPLC (compare FIG. 4A). The reaction mixture was immediately purified on a Sartobind Q cartridge as described below.

Sartobind Q Purification of PEG-EPO GlycoPEGylation Reaction Mixture

A Sartobind Q SingleSep Nano (1 mL) cartridge was attached to an AKTA Explorer 100 system continuously monitoring absorbance at 214, 254 and 280 nm. The cartridge was flushed with 20 mM HEPES, 1 M NaCl, pH 7.0 (approximately 100 mL), followed by 20 mM HEPES, 20 mM NaCl, pH 7.0 (approximately 100 mL) both at a flow rate of 15 mL/min. The PEG-EPO reaction mixture (approximately 25 mg, 6 mg/mL, 4.2 mL) was diluted with 20 mM HEPES, 20 mM NaCl, pH 7.0 (22.8 mL) to a final volume of 27 mL. A 1 mL aliquot was retained for analysis and the concentration was determined to be 0.804 mg/mL by RP-HPLC. The remaining diluted sample (26 mL, 20.9 mg by RP-HPLC) was loaded on to the capsule and washed with 20 mM HEPES, 20 mM NaCl, pH 7.0 (70 mL) at a flow rate of 15 mL/min.

Fractions were combined into a PEG-EPO product pool (80 mL). Samples of the pools and selected individual fractions across the flow through/wash product peak were analyzed by SDS-PAGE with iodine and nd silver stain. The conjugate recovery for this step (94%) was determined by RP-HPLC (Table 8).

The PEG-EPO pool was analyzed by MBP-ELISA for residual enzyme contaminants (Table 8) and then divided into two portions: The majority fraction (62 mL, 15.25 mg) was purified by HIC chromatography on Phenyl 650S resin as described below. A small sample (18 mL, 4.4 mg) was purified by an alternate process including Fluoroapatite chromatography.

Bound impurities were eluted from the column with 20 mM HEPES, 1 M NaCl, pH 7.0 (13 mL) at a flow rate of 15 mL/min.

Isolation of EPO-(SA-PEG-10 kDa)$_3$ from the Sartobind Q Flow Through/Wash Pool Using HIC (Phenyl 650S)

An XK26 column was packed with Phenyl 650S resin (106 mL, 2.6 cm×20 cm) as described herein above and was attached to an AKTA Explorer 100 system continuously monitoring absorbance at 214, 254 and 280 nm. The column was equilibrated with 5 column volumes (CV) 25 mM sodium phosphate, 0.6M sodium sulfate, pH 7.5 (212 mL). The Sartobind Q PEG-EPO product pool (62 mL, 18 mg, 0.17 mg PEG-EPO/mL resin, pH 6.94, 2.59 mS/cm) was diluted 1:1 with 1.2 M sodium sulfate, 25 mM sodium phosphate pH 7.5 (62 mL) to adjust the sodium sulfate concentration to 0.6 M. The conditioned sample (124 mL) was applied to the column. Unbound material was washed from the column using 5 CV of 25 mM sodium phosphate, 0.6M sodium sulfate, pH 7.5 (212 mL) at a flow rate of 8 mL/min (90 cm/hr). The PEG-EPO species were fractionated and eluted with the following gradient using Buffer A (25 mM sodium phosphate, pH 7.5) and Buffer B (25 mM sodium phosphate, 0.6M sodium sulfate, pH 7.5) at 8 mL/min (90 cm/hr): 100-60% B over 2 CV, isocratic hold at 60% B for 1 CV, 60-35% B over 13 CV (gradient change 1.92% B/CV), isocratic hold at 35% B for 1 CV, 35-0% B over 1 CV and 0% B for 5 CV. The flow through and wash fraction were collected in the bottle from a 1 L Nalgene filter unit and 12 mL elution fractions were collected in 14 mL Falcon tubes. Individual fractions were analyzed by SDS-PAGE. Fractions enriched in EPO-(SA-PEG-10 kDa)$_3$ were combined (after storage at 4° C. for about 36 hours). Fractions from other PEG-EPO species and elution peaks were also pooled. The fraction pools were analyzed by SDS-PAGE. The dilute EPO-(SA-PEG-10 kDa)$_3$ Pool (444 mL) was analyzed by A280 (0.025 mg/mL, 11.1 mg) and the step recovery was determined to be 73% (Table 1). This product pool was buffer exchanged and concentrated using Pellicon-2 XL regenerated cellulose membranes. The remaining 10 mg of material (19.44 mL) was held on ice prior to further purification by cation exchange chromatography on a Source 15S resin later the same day as described below.

Purification of the Concentrated and Diafiltered Phenyl 650S EPO-(SA-PEG-10 kDa)$_3$ Pool on Source 15S Chromatography A Tricorn 10 column was packed with Source 15S (15.7 mL, 1 cm×20 cm) and attached to an AKTA Explorer 100 system continuously monitoring absorbance at 214, 254 and 280 nm. The column was equilibrated with 5 column volumes (CV) 10 mM Na acetate, pH 5.4 (Buffer A). The concentrated and diafiltered Phenyl 650S EPO-(SA-PEG-10 kDa)$_3$ pool (10 mg PEG-EPO, 19.44 mL, pH 5.4, conductivity: 1.54 mS/cm) was divided into two equal portions which were purified on the prepared column in two separate but identical injections. Half of the diafiltered Phenyl 650S EPO-(SA-PEG-10 kDa)$_3$ product pool (5 mg PEG-EPO, 9.72 mL each, 0.32 mg PEG-EPO/mL resin) was applied to the column at a flow rate of 300 cm/h (1.96 mL/min). Unbound material was washed from the column using 5 CV of 10 mM Na acetate, pH 5.4 (Buffer A). The EPO-(SA-PEG-10 kDa)$_3$ was eluted with the following gradient with Buffer B (0.5 M NaCl, 10 mM Na acetate, pH 5.4): 0-30% B over 24 CV, isocratic hold at 30% B for 1 CV, step to 100% B for 5 CV. All steps were performed at 300 cm/h (1.96 mL/min). Fractions (1.6 mL) were collected in 96-deep well microtiter plates and stored at 4° C. Fractions from both injections were pooled. Protein content analysis (A280) of the EPO-(SA-PEG-10 kDa)$_3$ pool indicated that the step recovery over the Source 15S chromatography step was 79% (Table 8). RP-HPLC analysis of the product pool indicated that the EPO-(SA-PEG-10 kDa)$_2$ impurity had been reduced to 2.9% (Table 8). The product pool had an estimated sodium chloride concentration of approximately 70 mM and was concentrated and buffer exchanged. The Source 15S Flow Through/Wash pool was electroblotted onto PVDF membranes and subjected to Edman amino-terminal sequencing as described herein to determine the identity of the major band in the pool. The amino-terminal sequence obtained was determined to be EPO.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of making a composition comprising a first polypeptide conjugate, said first polypeptide conjugate comprising a first number of poly(alkylene oxide) moieties covalently linked to said first polypeptide, wherein at least one of said poly(alkylene oxide) moieties is covalently linked to said first polypeptide via a glycosyl linking group, wherein said glycosyl linking group is either covalently linked to an amino acid residue of said first polypeptide or is covalently linked to a glycosyl moiety of said first polypeptide, said method comprising:
   (a) contacting a mixture comprising said first polypeptide conjugate with an anion exchange medium;
   (b) eluting said first polypeptide conjugate from said anion exchange medium, forming a first eluate comprising said first polypeptide conjugate;
   (c) contacting said first eluate with a hydrophobic interaction chromatography (HIC) medium; and
   (d) eluting said first polypeptide conjugate from said hydrophobic interaction chromatography medium,
thereby making said composition comprising said first polypeptide conjugate.

2. The method of claim 1, wherein said mixture comprises a second polypeptide conjugate, wherein said second polypeptide conjugate comprises a second number of poly(alkylene oxide) moieties covalently linked to said second polypeptide, wherein said first number and said second number are different.

3. The method of claim 2, wherein said first polypeptide and said second polypeptide have the same amino acid sequence.

4. The method of claim 1, wherein said first polypeptide conjugate comprises a first glycosylation pattern, said first glycosylation pattern comprising at least one glycan residue covalently linked to said first polypeptide, each glycan residue optionally linked to at least one of said poly(alkylene oxide) moieties.

5. The method of claim 4, wherein said mixture comprises a second polypeptide conjugate, wherein said second polypeptide conjugate comprises a second number of poly(alkylene oxide) moieties covalently linked to said second polypeptide, wherein said first number and said second number are different.

6. The method of claim 5, wherein said second polypeptide conjugate comprises a second glycosylation pattern, wherein said second glycosylation pattern differs from said first glycosylation pattern of said first polypeptide conjugate by at least one glycosyl moiety of said at least one glycan residue.

7. The method of claim 5, wherein said mixture comprises a third polypeptide conjugate comprising a third number of poly(alkylene oxide) moieties covalently linked to said third polypeptide, wherein said third polypeptide conjugate comprises a second glycosylation pattern, wherein said second glycosylation pattern differs from said first glycosylation pattern of said first polypeptide conjugate by at least one glycosyl moiety of said at least one glycan residue.

8. The method of claim 4, wherein each of said poly(alkylene oxide) moieties is covalently linked to said first polypeptide via an O-linked or N-linked glycan residue.

9. The method of claim 4, wherein said glycosylation pattern of said first polypeptide conjugate is a substantially uniform insect-specific glycosylation pattern.

10. The method of claim 1, wherein said HIC medium is selected from a butyl and a phenyl resin.

11. The method of claim 1, wherein each of said poly(alkylene oxide) moieties is a member independently selected from a poly(ethylene glycol) moiety and a polypropylene glycol) moiety.

12. The method of claim 11, wherein each of said poly(alkylene oxide) moieties has a molecular weight between about 1 kDa and about 200 kDa.

13. The method of claim 1, wherein said first polypeptide is a therapeutic polypeptide.

14. The method of claim 1, wherein said first polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, granulocyte colony stimulating factor (G-CSF), granulocyte-macrophage colony stimulating factor (GM-CSF), interferon alpha, interferon beta, interferon gamma, α1-antitrypsin (α-1 protease inhibitor), glucocerebrosidase, tissue-type plasminogen activator (TPA), interleukin-2 (IL-2), leptin, hirudin, urokinase, human DNase, insulin, hepatitis B surface protein (HbsAg), chimeric diphtheria toxin-IL-2, human growth hormone (hGH), human chorionic gonadotropin (hCG), thyroid peroxidase (TPO), alpha-galactosidase, alpha-L-iduronidase, beta-glucosidase, alpha-galactosidase A, acid α-glucosidase (acid maltase), anti-thrombin III (AT III), follicle stimulating hormone (FSH), glucagon-like peptide-1 (GLP-1), glucagon-like peptide-2 (GLP-2), fibroblast growth factor 7 (FGF-7), fibroblast growth factor 21 (FGF-21), fibroblast growth factor 23 (FGF-23), Factor VII, Factor VIII, B-domain deleted Factor VIII, vWF-Factor VIII fusion protein having full-length Factor VIII, vWF-Factor VIII fusion protein having B-domain deleted Factor VIII, Factor IX, Factor X, Factor XIII, prokinetisin, extendin-4, CD4, tumor necrosis factor receptor (TNF-R), α-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-α, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

15. The method of claim 1, wherein said first polypeptide is erythropoietin (EPO).

16. The method of claim 15, wherein said EPO is covalently linked to three poly(ethylene glycol) moieties.

17. The method of claim 16, wherein at least two of said three poly(ethylene glycol) moieties are covalently linked to said EPO via an N-linked glycan.

18. The method of claim 15, wherein said EPO comprises the amino acid sequence according to SEQ ID NO: 1, said sequence optionally having at least one mutation selected from the group consisting of $Arg^{139}$ to $Ala^{139}$, $Arg^{143}$ to $Ala^{143}$ and $Lys^{154}$ to $Ala^{154}$.

19. The method of claim 1, wherein said glycosyl linking group is an intact glycosyl linking group.

20. The method of claim 19, wherein said intact glycosyl linking group is a member selected from a glucosaminyl (GlcNH) moiety, a N-acetylglucosaminyl (GlcNAc) moiety, and a sialic acid moiety.

21. The method of claim 1, further comprising:
(e) contacting said first polypeptide conjugate with a cation exchange chromatography medium and eluting said first polypeptide conjugate from the cation exchange chromatography medium.

22. The method of claim 21, wherein step (e) is performed after step (d).

23. The method of claim 1, further comprising: contacting said first polypeptide and a modified sugar nucleotide having a glycosyl moiety covalently linked to a poly(alkylene oxide) moiety, in the presence of a glycosyltransferase under conditions sufficient for said glycosyltransferase to form a covalent bond between said glycosyl moiety and said first polypeptide, thereby forming said first polypeptide conjugate.

24. The method of claim 23, wherein said glycosyl moiety is a sialic acid moiety and said glycosyltransferase is a sialyltransferase.

25. The method of claim 23, further comprising: recombinantly expressing said first polypeptide in an insect cell.

26. A method of isolating a first polypeptide conjugate comprising a first number of poly(alkylene oxide) moieties covalently linked to said first polypeptide, wherein at least one of said poly(alkylene oxide) moieties is attached to said first polypeptide via a glycosyl linking group, wherein said glycosyl linking group is covalently linked to an amino acid residue of said first polypeptide or is covalently linked to a glycosyl moiety of said first polypeptide, from a second polypeptide conjugate comprising a second number of poly (alkylene oxide) moieties covalently linked to said second polypeptide, wherein said first number is selected from 1 to 20 and said second number is selected from 0-20, said first number and said second number being different, said method comprising:
(a) contacting a mixture comprising said first polypeptide conjugate and said second polypeptide conjugate with an anion exchange medium;
(b) eluting said first polypeptide conjugate and said second polypeptide conjugate from said anion exchange medium, forming a first eluate comprising said first polypeptide conjugate and said second polypeptide conjugate;
(c) contacting said first eluate with a hydrophobic interaction chromatography (HIC) medium; and
(d) eluting said first polypeptide conjugate from said hydrophobic interaction chromatography medium,
thereby isolating said first polypeptide conjugate from said second polypeptide conjugate.

27. The method of claim 26, wherein each of said poly (alkylene oxide) moieties is a member independently selected from a poly(ethylene glycol) moiety and a polypropylene glycol) moiety.

28. The method of claim 27, wherein each of said poly (alkylene oxide) moieties has an independently selected molecular weight between about 1 kDa and about 200 kDa.

29. The method of claim 26, wherein said first polypeptide and said second polypeptide have the same amino acid sequence.

30. The method of claim 26, wherein said first polypeptide is a therapeutic polypeptide.

31. The method of claim 26, wherein said first polypeptide is a member selected from bone morphogenetic protein 2 (BMP-2), bone morphogenetic protein 7 (BMP-7), bone morphogenetic protein 15 (BMP-15), neurotrophin-3 (NT-3), von Willebrand factor (vWF) protease, granulocyte colony stimulating factor (G-CSF), granulocyte-macrophage colony stimulating factor (GM-CSF), interferon alpha, interferon beta, interferon gamma, α1-antitrypsin (α-1 protease inhibitor), glucocerebrosidase, tissue-type plasminogen activator (TPA), interleukin-2 (IL-2), leptin, hirudin, urokinase, human DNase, insulin, hepatitis B surface protein (HbsAg), chimeric diphtheria toxin-IL-2, human growth hormone (hGH), human chorionic gonadotropin (hCG), thyroid peroxidase (TPO), alpha-galactosidase, alpha-L-iduronidase, beta-glucosidase, alpha-galactosidase A, acid α-glucosidase (acid maltase), anti-thrombin III (AT III), follicle stimulating hormone (FSH), glucagon-like peptide-1 (GLP-1), glucagon-like peptide-2 (GLP-2), fibroblast growth factor 7 (FGF-7), fibroblast growth factor 21 (FGF-21), fibroblast growth factor 23 (FGF-23), Factor VII, Factor VIII, B-domain deleted Factor VIII, vWF-Factor VIII fusion protein having full-length Factor VIII, vWF-Factor VIII fusion protein having B-domain deleted Factor VIII, Factor IX, Factor X, Factor XIII, prokinetisin, extendin-4, CD4, tumor necrosis factor receptor (TNF-R), α-CD20, P-selectin glycoprotein ligand-1 (PSGL-1), complement, transferrin, glycosylation-dependent cell adhesion molecule (GlyCAM), neural-cell adhesion molecule (N-CAM), TNF receptor-IgG Fc region fusion protein, anti-HER2 monoclonal antibody, monoclonal antibody to respiratory syncytial virus, monoclonal antibody to protein F of respiratory syncytial virus, monoclonal antibody to TNF-α, monoclonal antibody to glycoprotein IIb/IIIa, monoclonal antibody to CD20, monoclonal antibody to VEGF-A, monoclonal antibody to PSGL-1, monoclonal antibody to CD4, monoclonal antibody to a-CD3, monoclonal antibody to EGF, monoclonal antibody to carcinoembryonic antigen (CEA) and monoclonal antibody to IL-2 receptor.

32. The method of claim 26, wherein said first polypeptide is erythropoietin (EPO).

33. The method of claim 32, wherein said EPO is covalently linked to three poly(ethylene glycol) moieties.

34. The method of claim 33, wherein at least two of said three poly(ethylene glycol) moieties are covalently linked to said EPO via a N-linked glycan.

35. The method of claim 32, wherein said EPO comprises the amino acid sequence according to SEQ ID NO: 1, said sequence optionally having at least one mutation selected from the group consisting of $Arg^{139}$ to $Ala^{139}$, $Arg^{143}$ to $Ala^{143}$ and $Lys^{154}$ to $Ala^{154}$.

36. The method of claim 26, wherein said HIC medium is a member selected from a butyl and a phenyl resin.

37. The method of claim 26, wherein said glycosyl linking group is an intact glycosyl linking group.

38. The method of claim 37, wherein said intact glycosyl linking group is a member selected from a glucosaminyl (GlcNH) moiety, a N-acetylglucosaminyl (GlcNAc) moiety, and a sialic acid moiety.

39. The method of claim 26, further comprising:
(e) contacting said first polypeptide conjugate with a cation exchange chromatography medium and eluting said first polypeptide conjugate from said cation exchange chromatography medium.

40. The method of claim 39, wherein step (e) is performed after step (d).

41. The method of claim 26, wherein said first polypeptide conjugate comprises a substantially uniform insect-specific glycosylation pattern.

42. The method of claim 26, further comprising: contacting said first polypeptide with a modified sugar nucleotide having a glycosyl moiety covalently linked to a poly(alkylene oxide) moiety, in the presence of a glycosyltransferase under conditions sufficient for said glycosyltransferase to form a covalent bond between said glycosyl moiety and said first polypeptide, thereby forming said first polypeptide conjugate.

43. The method of claim 42, wherein said glycosyl moiety is a sialic acid moiety and said glycosyltransferase is a sialyltransferase.

44. The method of claim 43, further comprising: recombinantly expressing said first polypeptide in an insect cell.

45. The method of claim 44, further comprising: contacting said first polypeptide and a nucleotide sugar in the presence of an enzyme for which the nucleotide sugar is a substrate under conditions sufficient for said enzyme to form a covalent bond between said sugar of said nucleotide sugar and said first polypeptide, wherein said first polypeptide is a member selected from glycosylated and non-glycosylated.

46. A method of forming a composition comprising a first erythropoietin (EPO) conjugate, said first EPO conjugate comprising a first number of poly(alkylene oxide) moieties covalently linked to said EPO, wherein said EPO conjugate comprises at least one poly(alkylene oxide) moiety that is covalently linked to said EPO via a glycosyl linking group, wherein said glycosyl linking group is covalently linked to an amino acid residue of said EPO or is covalently linked to a glycosyl moiety of said EPO, said method comprising:
(a) contacting a mixture comprising said first EPO conjugate with an anion exchange medium;
(b) eluting said first EPO conjugate from said anion exchange medium, forming a first eluate comprising said first EPO conjugate;
(c) contacting said first eluate with a hydrophobic interaction chromatography (HIC) medium; and
(d) eluting said first EPO conjugate from said hydrophobic interaction chromatography medium,
thereby forming a composition comprising said first EPO conjugate.

47. The method of claim 46, wherein said mixture of step (a) comprises a second EPO conjugate having a second number of poly(alkylene oxide) moieties covalently linked to said EPO, wherein said first number and said second number are different.

48. The method of claim 47, wherein said first number is 3 and said second number is a member selected from 0, 1, 2 and 4.

49. The method of claim 47, wherein said second EPO conjugate is present in said composition at a concentration that is less than about 10%.

50. The method of claim 46, wherein said HIC medium is a member selected from a butyl and a phenyl resin.

51. The method of claim 46, wherein each of said poly(alkylene oxide) moieties is a member independently selected from a poly(ethylene glycol) moiety and a polypropylene glycol) moiety.

52. The method of claim 51, wherein each of said poly(alkylene oxide) moieties has an independently selected molecular weight between about 1 kDa and about 200 kDa.

53. The method of claim 46, wherein said first EPO conjugate comprises three poly(ethylene glycol) moieties.

54. The method of claim 53, wherein at least two of said three poly(ethylene glycol) moieties are covalently attached to said EPO via an N-linked glycan.

55. The method of claim 46, wherein said EPO comprises the amino acid sequence according to SEQ ID NO: 1, said sequence optionally having at least one mutation selected from the group consisting of $Arg^{139}$ to $Ala^{139}$, $Arg^{143}$ to $Ala^{143}$ and $Lys^{154}$ to $Ala^{154}$.

56. The method of claim 46, wherein said glycosyl linking group is an intact glycosyl linking group.

57. The method of claim 56, wherein said intact glycosyl linking group is a member selected from a glucosaminyl (GlcNH) moiety, a N-acetylglucosaminyl (GlcNAc) moiety, and a sialic acid moiety.

58. The method of claim 46, further comprising:
(e) contacting said first EPO conjugate with a cation exchange medium and eluting said first EPO conjugate from the cation exchange chromatography medium.

59. The method of claim 58, wherein step (e) is performed after step (d).

60. The method of claim 46, wherein said EPO comprises a substantially uniform insect-specific glycosylation pattern.

61. The method of claim 46, further comprising: contacting said EPO and a modified sugar nucleotide having a glycosyl moiety covalently attached to a poly(alkylene oxide) moiety, in the presence of a glycosyltransferase under conditions sufficient for said glycosyltransferase to form a covalent bond between said glycosyl moiety and said EPO, thereby forming said first EPO conjugate.

62. The method of claim 61, wherein said glycosyl moiety is a sialic acid moiety and said glycosyltransferase is a sialyltransferase.

63. The method of claim 61, further comprising: recombinantly expressing said EPO in an insect cell, thereby forming an insect cell-culture liquid comprising said EPO.

64. The method of claim 63, further comprising: isolating said EPO from said insect cell-culture liquid.

65. The method of claim 61, further comprising: contacting in a single reaction vessel said EPO and a nucleotide-N- acetylglucosamine (GlcNAc) molecule and a nucleotide galactose (Gal) molecule in the presence of a N-acetylglucosamine transferase selected from GnT1 and GnT2, and a galactosyl transferase, under conditions sufficient for said N-acetylglucosamine transferase and said galactosyl transferase to form a terminal—GlcNAc-Gal moiety covalently linked to said EPO.

* * * * *

SEQUENCE LISTING

```
<160> NUMBER OF SEQ ID NOS: 1

<210> SEQ ID NO 1
<211> LENGTH: 165
<212> TYPE: PRT
<213> ORGANISM: homo sapiens
<220> FEATURE:
<221> NAME/KEY: VARIANT
<222> LOCATION: (1)...(165)
<223> OTHER INFORMATION: erythropoietin

<400> SEQUENCE: 1

Ala Pro Pro Arg Leu Ile Cys Asp Ser Arg Val Leu Glu Arg Tyr Leu
 1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45
```

```
Tyr Ala Trp Lys Arg Met Glu Val Gly Gln Gln Ala Val Glu Val Trp
    50              55                  60

Gln Gly Leu Ala Leu Leu Ser Glu Ala Val Leu Arg Gly Gln Ala Leu
65              70                  75                      80

Leu Val Asn Ser Ser Gln Pro Trp Glu Pro Leu Gln Leu His Val Asp
            85                  90                  95

Lys Ala Val Ser Gly Leu Arg Ser Leu Thr Thr Leu Leu Arg Ala Leu
            100             105                 110

Gly Ala Gln Lys Glu Ala Ile Ser Pro Pro Asp Ala Ala Ser Ala Ala
        115             120                 125

Pro Leu Arg Thr Ile Thr Ala Asp Thr Phe Arg Lys Leu Phe Arg Val
    130             135                 140

Tyr Ser Asn Phe Leu Arg Gly Lys Leu Lys Leu Tyr Thr Gly Glu Ala
145             150                 155                     160

Cys Arg Thr Gly Asp
            165
```